US006324249B1

(12) United States Patent
Fazzio

(10) Patent No.: US 6,324,249 B1
(45) Date of Patent: Nov. 27, 2001

(54) ELECTRONIC PLANAR LAMINOGRAPHY SYSTEM AND METHOD

(75) Inventor: R. Shane Fazzio, Loveland, CO (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/813,778

(22) Filed: Mar. 21, 2001

(51) Int. Cl.$^7$ ................................... G01N 23/00
(52) U.S. Cl. .................... 378/22; 378/58; 378/98.8
(58) Field of Search .................. 378/21, 22, 24, 378/25, 58, 98.8

(56) References Cited

U.S. PATENT DOCUMENTS

| Re. 36,047 | 1/1999 | Gilblom et al. ................ 348/91 |
| 4,132,896 | 1/1979 | Klotz et al. .................. 250/445 T |
| 4,179,100 | 12/1979 | Sashin et al. ................. 250/416 TV |
| 4,340,816 | 7/1982 | Schott ........................ 250/44 ST |
| 4,349,740 | 9/1982 | Grassmann et al. .............. 378/25 |
| 4,383,327 | 5/1983 | Kruger ........................... 378/19 |
| 4,411,012 | 10/1983 | Pfeiler et al. ................... 378/17 |
| 4,718,075 | 1/1988 | Horn ............................ 378/91 |
| 4,730,350 | 3/1988 | Albert ........................... 378/10 |
| 4,809,308 | 2/1989 | Adams et al. ................... 378/99 |
| 4,852,131 | 7/1989 | Armistead ....................... 378/4 |
| 4,906,850 | 3/1990 | Beerlage ..................... 250/370.09 |
| 4,926,452 | 5/1990 | Baker et al. .................... 378/22 |
| 5,012,498 | 4/1991 | Cuzin et al. .................... 378/22 |
| 5,081,656 | 1/1992 | Baker et al. .................... 378/21 |
| 5,097,492 | 3/1992 | Baker et al. .................... 378/22 |
| 5,199,054 | 3/1993 | Adams et al. ................... 378/21 |
| 5,259,012 | 11/1993 | Baker et al. ................... 378/21 |
| 5,291,535 | 3/1994 | Baker et al. ................... 378/22 |
| 5,428,392 | 6/1995 | Castro et al. .................. 348/295 |
| 5,500,886 | 3/1996 | Duff ........................... 378/207 |
| 5,561,696 | 10/1996 | Adams et al. ................... 378/58 |
| 5,583,904 | 12/1996 | Adams .......................... 378/22 |
| 5,594,770 | 1/1997 | Bowles et al. .................. 378/58 |
| 5,621,811 | 4/1997 | Roder et al. .................. 382/147 |
| 5,687,209 | 11/1997 | Adams .......................... 378/22 |
| 6,002,739 | 12/1999 | Heumann ........................ 378/8 |
| 6,049,584 | 4/2000 | Pfeiffer ........................ 378/39 |

FOREIGN PATENT DOCUMENTS 0 683 389    11/1995   (EP) .

OTHER PUBLICATIONS

Hasenkamp, "Radiographic Laminography," *Materials Evaluation*, Aug. 1974, pp. 169–180.

(List continued on next page.)

Primary Examiner—David P. Porta
Assistant Examiner—Jurie Yun

(57) ABSTRACT

An improved linear scan geometry laminography system that allows for generation of high speed and high resolution X-ray laminographs using an electronic detector operating in a time-domain integration mode coupled with a moving source of X-rays. In one embodiment, the improved scanning laminography system does not require any mechanical motion of the object being inspected, the X-ray source or detectors. Higher speed is achieved over conventional laminography systems due to the electronic nature of the scan. The same architecture also allows for both two-dimensional radiography and digital reconstruction techniques. Usage of the technique provides for higher throughput, higher resolution, and simpler designs than do currently available systems. An analysis of different system design parameters for the basic X-ray imaging architecture utilizing time-domain integration to generate cross-sectional images is included to facilitate specific design configurations. The relationships between resolution, speed, and cost are considered.

49 Claims, 18 Drawing Sheets

OTHER PUBLICATIONS

Deane et al., IRT Corp., "Using X–Ray Vision to Verify SMD–Based Quality," *Electronics Test,* Feb. 1987, pp. 32–35.

Soron, IRT Corp., X–Ray Inspection Meets Increased PWB Throughout, Density Challenge— Part 1, *Electronics,* Oct. 1987, pp. 36–37.

Pound, "Image Processing Boosts the Power of Non–destructive Testing," *Electronic Packaging and Production,* Jun. 1985.

Casey, "X–Ray Inspection," *Manufacturing Systems,* Jul. 1987, p. 18ff.

Corey, IRT Corp., "Artificial Perception Gives Super Vision," *Research and Development,* Oct. 1984.

Wittenberg, "IRT Improves SMT X–Ray Inspection System," *Electronic Engineering Times,* Oct. 5, 1987, p. 53.

Phelps, Christi, "Four Pi Captures Contact, capital; Unveils Product," *San Diego Business Journal,* Week of Oct. 10–16, 1888.

Four Pi Systems product brochure for "3DX Series 2000" Automated Inspection System, Copyright 1988.

Juha, Mike, "Automated Inspection of Surface Mounted Device Solder Connections", Proceedings of Soldering Technology Seminar—Feb. 19–20, 1985, Naval Weapons Center, China Lake, CA, Publication NWC TS 85–25, pp. 73–90.

Smith, Charles R. and Erker, Joseph W., "Low cost, high resolution x–ray detector system for digital radiography and computed tomography", *SPIE vol. 2009 X–Ray Detector Physics and Applications II,* 1993 pp. 31–35.

Kieffer, Jean, "Analysis of Laminagraphic Motions and Their Values", *Radiology,* vol. 33, Nov. 1939, pp. 560–585.

Liu, Hong; Karellas, Andrew; Harris, Lisa J.; and D'Orsi, Carl J., "Methods to calculate the lens efficiency in optically coupled CCD x–ray imaging systems", *Med. Phys.,* 21(7), Jul. 1994, pgs.

Fazzio, R. Shane, "Radiation exposure in a modern, circularly scanned–beam laminographic X–ray inspection system", *Journal of X–Ray Science and Technology,* 8, 1998, pp. 117–133.-

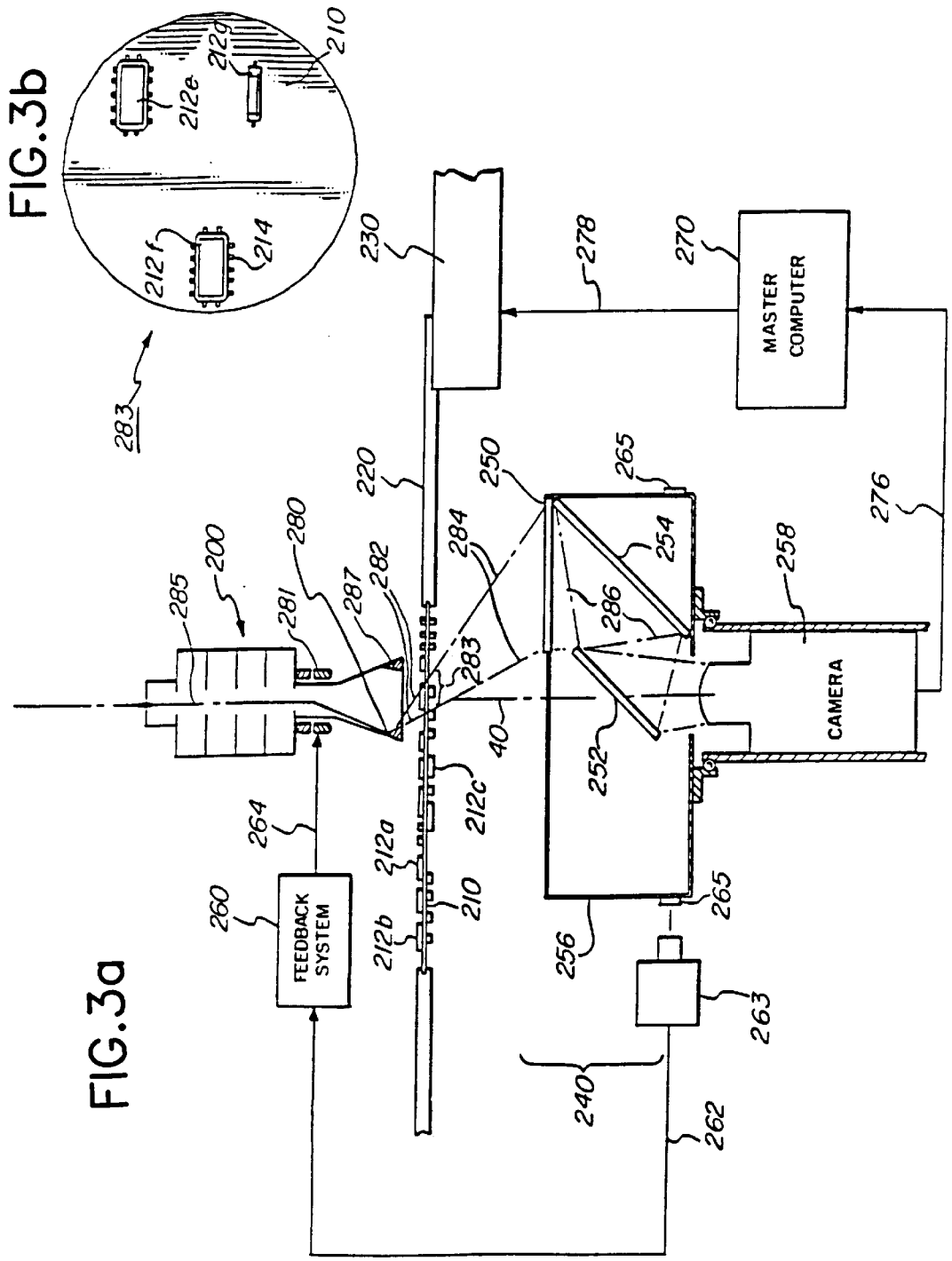

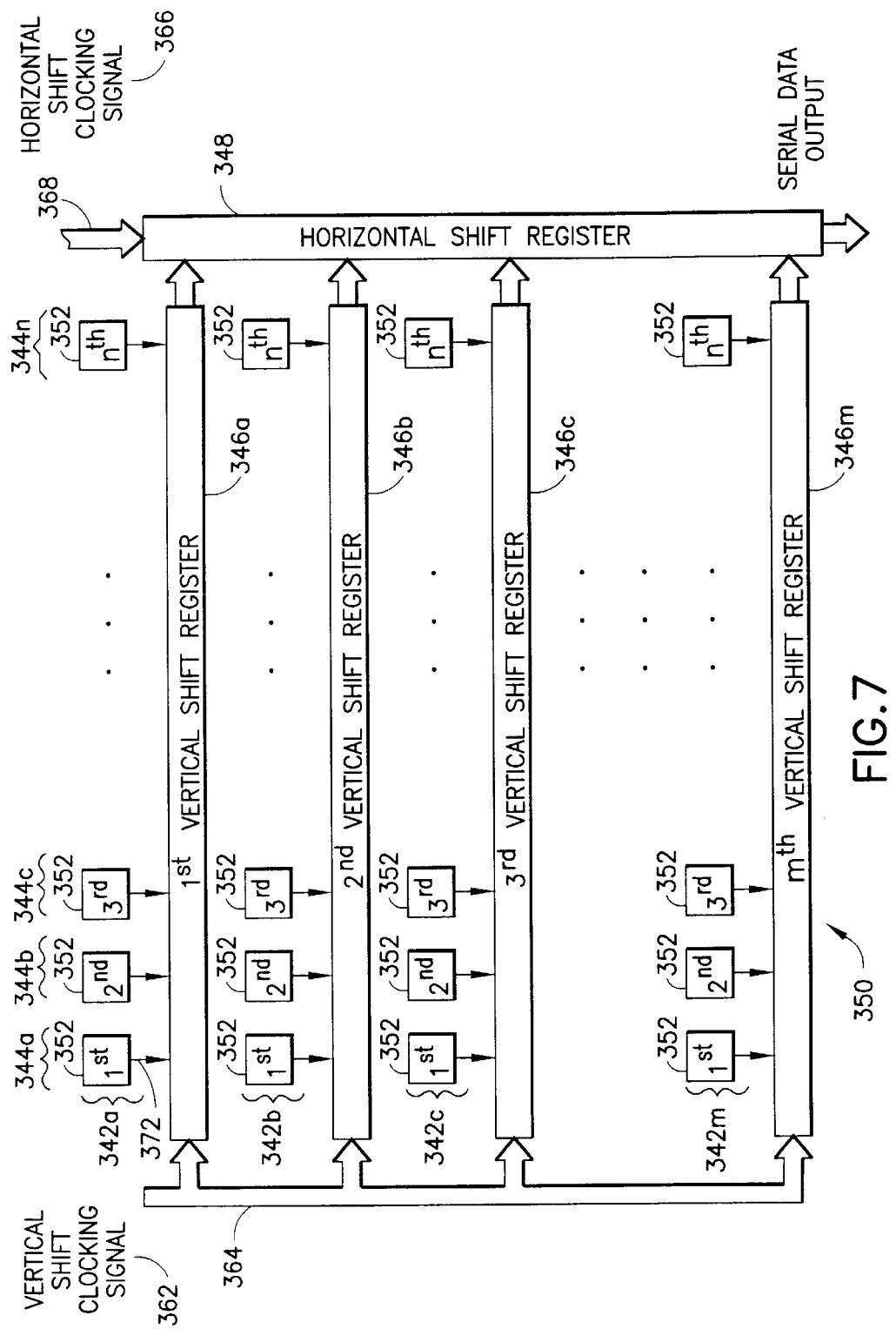

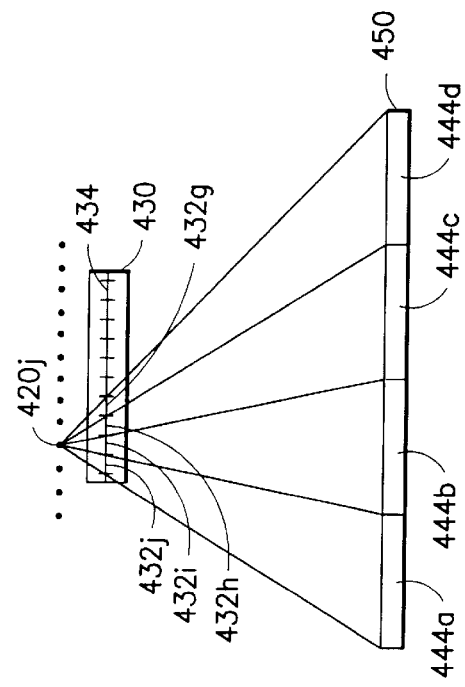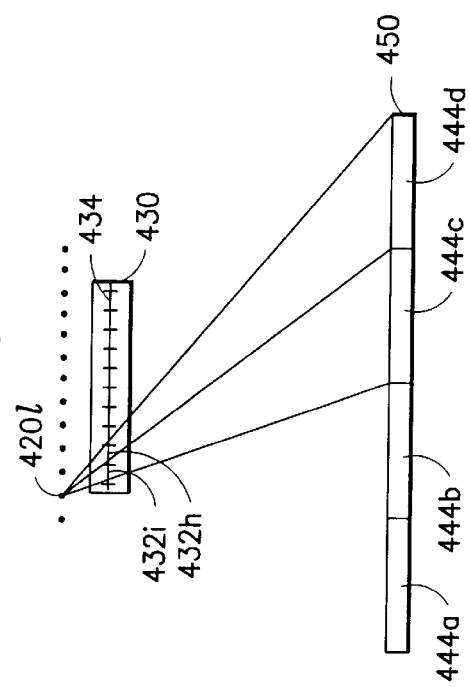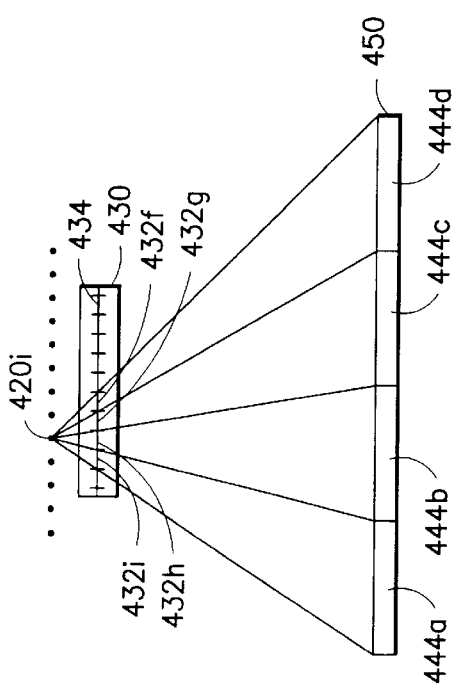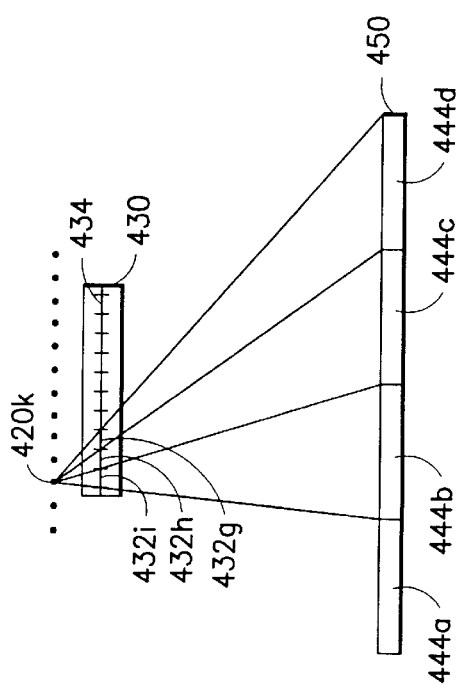

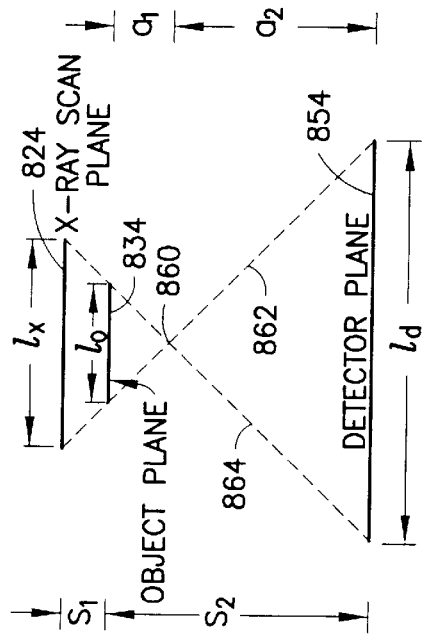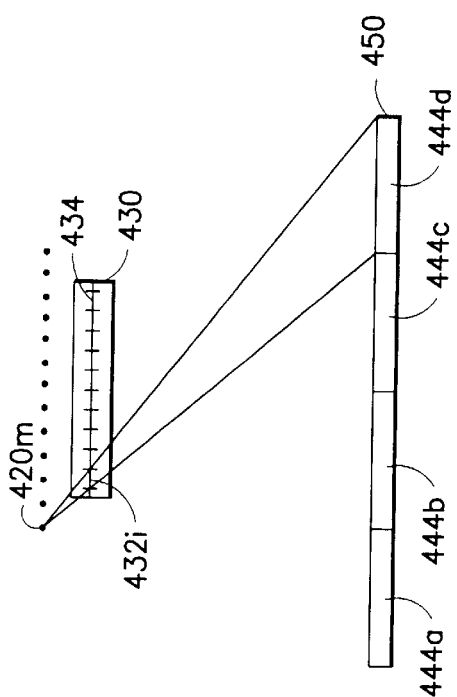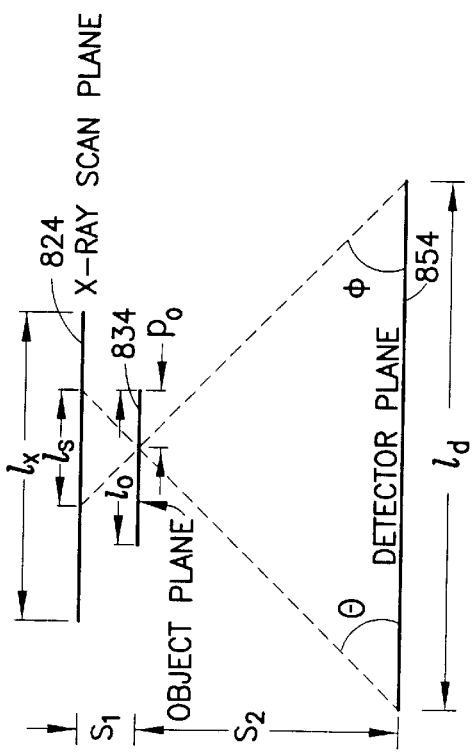

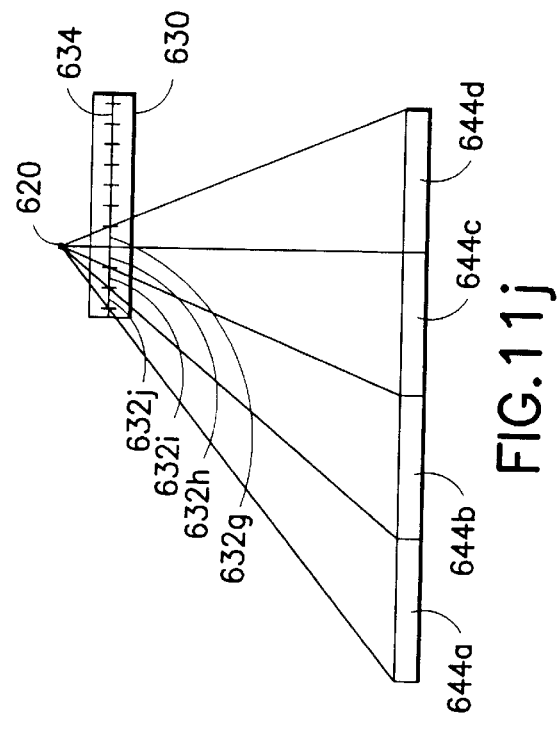
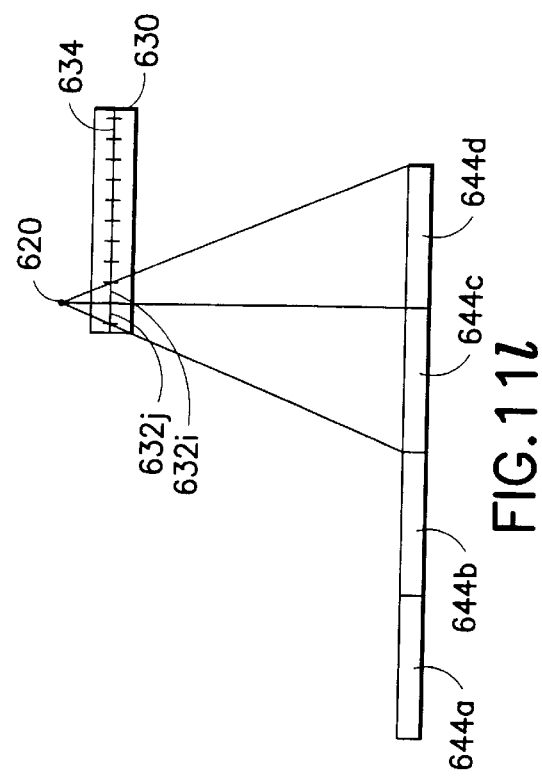
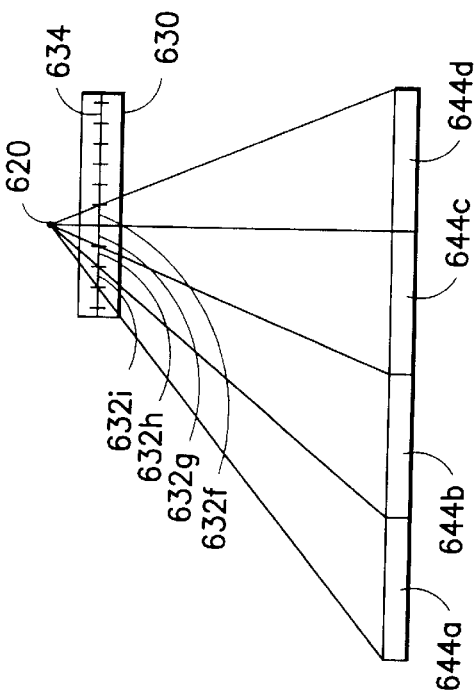
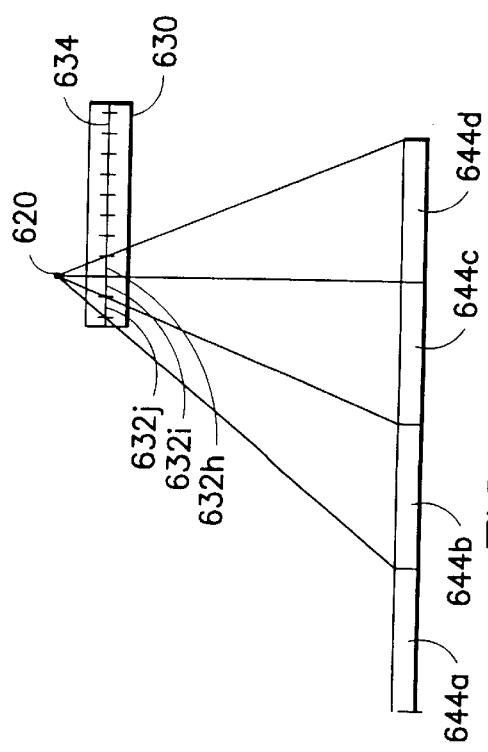

ELECTRONIC PLANAR LAMINOGRAPHY SYSTEM AND METHOD

FIELD OF THE INVENTION

The invention relates generally to laminography, and more specifically to systems which use an electronic linear scan method for high speed, high resolution generation of laminographic images.

BACKGROUND OF THE INVENTION

Rapid and precise quality control inspections of the soldering and assembly of electronic devices have become priority items in the electronics manufacturing industry. The reduced size of components and solder connections, the resulting increased density of components on circuit boards and the advent of surface mount technology (SMT), which places solder connections underneath device packages where they are hidden from view, have made rapid and precise inspections of electronic devices and the electrical connections between devices very difficult to perform in a manufacturing environment.

Many existing inspection systems for electronic devices and connections make use of penetrating radiation to form images which exhibit features representative of the internal structure of the devices and connections. These systems often utilize conventional radiographic techniques wherein the penetrating radiation comprises X-rays. Medical X-ray pictures of various parts of the human body, e.g., the chest, arms, legs, spine, etc., are perhaps the most familiar examples of conventional radiographic images. The images or pictures formed represent the X-ray shadow cast by an object being inspected when it is illuminated by a beam of X-rays. The X-ray shadow is detected and recorded by an X-ray sensitive material such as film or other suitable means.

The appearance of the X-ray shadow or radiograph is determined not only by the internal structural characteristics of the object, but also by the direction from which the incident X-rays strike the object. Therefore, a complete interpretation and analysis of X-ray shadow images, whether performed visually by a person or numerically by a computer, often requires that certain assumptions be made regarding the characteristics of the object and its orientation with respect to the X-ray beam. For example, it is often necessary to make specific assumptions regarding the shape, internal structure, etc. of the object and the direction of the incident X-rays upon the object. Based on these assumptions, features of the X-ray image may be analyzed to determine the location, size, shape, etc., of the corresponding structural characteristic of the object, e.g., a defect in a solder connection, which produced the image feature. These assumptions often create ambiguities which degrade the reliability of the interpretation of the images and the decisions based upon the analysis of the X-ray shadow images. One of the primary ambiguities resulting from the use of such assumptions in the analysis of conventional radiographs is that small variations of a structural characteristic within an object, such as the shape, density and size of a defect within a solder connection, are often masked by the overshadowing mass of the solder connection itself as well as by neighboring solder connections, electronic devices, circuit boards and other objects. Since the overshadowing mass and neighboring objects are usually different for each solder joint, it is extremely cumbersome and often nearly impossible to make enough assumptions to precisely determine shapes, sizes and locations of solder defects within individual solder joints.

In an attempt to compensate for these shortcomings, some systems incorporate the capability of viewing the object from a plurality of angles. One such system is described in U.S. Pat. No. 4,809,308 entitled "METHOD & APPARATUS FOR PERFORMING AUTOMATED CIRCUIT BOARD SOLDER QUALITY INSPECTIONS", issued to Adams et al. The additional views enable these systems to partially resolve the ambiguities present in the X-ray shadow projection images. However, utilization of multiple viewing angles necessitates a complicated mechanical handling system, often requiring as many as five independent, non-orthogonal axes of motion. This degree of mechanical complication leads to increased expense, increased size and weight, longer inspection times, reduced throughput, impaired positioning precision due to the mechanical complications, and calibration and computer control complications due to the non-orthogonality of the axes of motion.

Another approach for acquiring shadowgraph X-ray images uses a slit scan geometry with an electronic detector to reduce scattering and interference from adjacent regions of the object being inspected. For example, U.S. Pat. No. 4,383,327 entitled "RADIOGRAPHIC SYSTEMS EMPLOYING MULTI-LINEAR ARRAYS OF ELECTRONIC RADIATION DETECTORS", issued to Kruger describes a scanning radiographic system which uses a multi-linear array operating in a time delay and integration (TDI) mode to generate a slit-scan shadowgraph image of a moving object. Kruger discloses the use of a beam of electronic radiation (e.g., X-rays) generated by a suitable source of electronic radiation. The beam of electronic radiation is directed towards, and aligned with, an array of electronic radiation detectors. Each of the detectors on the array is adapted to generate a signal having a magnitude proportional to the amount of radiation it senses. The array also includes, as an integral part thereof, signal processing capabilities whereby the signals generated by each of the detectors may be stored in respective storage elements. These stored signals, at controlled time intervals, are all shifted to the storage elements of other, adjacent, detectors. Once the signals have been shifted, the signals are augmented by new signals, if any, generated by the respective detectors of the storage elements in which the signals are stored. After having been shifted through several storage elements, these augmented signals may exit from the array to be further processed and conditioned so as to enable an image to be created through a suitable visual system. In connection with the above shifting and processing of radiation signals, the opaque specimen is passed between the source of electronic radiation and the array at a controlled speed and in a known pattern. This controlled speed is synchronized with the controlled time intervals at which the signals are shifted from storage element to storage element. Furthermore, the shifting pattern—that is the sequence that the signals follow as they are shifted from storage element to storage element within the array—is designed to be the same as the movement pattern of the opaque specimen through the beam of electronic radiation. When the shifting pattern of the detector signals is the same as the movement pattern of the opaque specimen, a non-blurred image may be generated. That is, each pixel, or small area, of the image is generated from radiation that passes through a corresponding small area of the specimen. At any instant of time, this radiation falls upon a given detector and generates a signal for that pixel. As the specimen moves, causing the radiation passing through the same small area thereof to likewise move and fall upon an adjacent detector, the pixel signal generated prior to the movement is shifted to the storage element associated with the detector receiving the radiation after the movement. At each storage element, the resolution of the pixel signal is augmented by having it updated to reflect the amount of radiation passing through the corresponding area of the specimen at that particular time. In this fashion, each pixel in the accumulated image results from an integration process. This process is commonly referred to as a time delay and integration (TDI) mode. As shown in Kruger, the angular relationship between the X-ray source, the specific row of image points of the body being examined and the image-recording elements is substantially the same during the production of the X-ray image, i.e., the procedure results in a traditional slit scan transmission X-ray showgraph or radiograph of the object. This TDI (Time Delay and Integration) method of scanning is found to be of particularly good applicability in the examination of bodies by means of X-ray radiation, it being possible for a usable image to be formed despite the fact that each image-recording element, per se, generates only a very small amount of charge in response to the radiation received. A comprehensive discussion of the TDI principle is included in U.S. Pat. No. 4,383,327, the entirety of which is hereby incorporated herein by reference.

The TDI (Time Delay and Integration) mode for operating a CCD camera may also be found in other applications for CCD cameras. For example, U.S. Pat. No. Re. 36,047 entitled "MULTI-MODE TDI/RASTER-SCAN TELEVISION CAMERA SYSTEM", issued to Gilblom et al. describes an optical web inspection system where a CCD operating in a time-delay-and-integration (TDI) mode generates an image of a moving object. U.S. Pat. No. 6,049,584 entitled "X-RAY DIAGNOSTIC APPARATUS FOR PRODUCING PANORAMA SLICE EXPOSURE OF BODY PARTS OF A PATIENT", issued to Pfeiffer describes an apparatus wherein an X-ray source and a CCD detector (having multiple narrow TDI zones) rotate about a patient to produce and sharply image several arbitrarily selectable slices, using a single mechanically executed orthopantomogram. U.S. Patent No. 5,428,392 entitled "STROBING TIME-DELAYED AND INTEGRATION VIDEO CAMERA SYSTEM", issued to Castro et al. describes a TDI camera assembly mounted to view a rotating or other cyclically moving object. The entirety of each of the above referenced patents is hereby incorporated herein by reference.

Many of the problems associated with the conventional radiography techniques discussed above may be alleviated by producing cross-sectional images of the object being inspected. Tomographic techniques such as laminography and computed tomography (CT) have been used in medical applications to produce cross-sectional or body section images. In medical applications, these techniques have met with widespread success, largely because relatively low resolution on the order of one or two millimeters (0.04 to 0.08 inches) is satisfactory and because speed and throughput requirements are not as severe as the corresponding industrial requirements.

In the case of electronics inspection, and more particularly, for inspection of electrical connections such as solder joints, image resolution on the order of several micrometers (for example, a minimum resolved feature size of approximately 20 micrometers (0.0008 inches)) is preferred for current electronic designs. However, better resolution and higher inspection speeds are desirable for inspecting current electronic designs and are rapidly becoming necessary for the inspection of future electronic designs. Furthermore, an industrial solder joint inspection system must generate multiple images per second in order to be practical for use on an industrial production line. Laminography systems which are capable of achieving the speed and accuracy requirements currently necessary for electronics inspection are described in the following patents: 1) U.S. Pat. No. 4,926,452 entitled "AUTOMATED LAMINOGRAPHY SYSTEM FOR INSPECTION OF ELECTRONICS", issued to Baker et al.; 2) U.S. Pat. No. 5,097,492 entitled "AUTOMATED LAMINOGRAPHY SYSTEM FOR INSPECTION OF ELECTRONICS", issued to Baker et al.; 3) U.S. Pat. No. 5,081,656 entitled "AUTOMATED LAMINOGRAPHY SYSTEM FOR INSPECTION OF ELECTRONICS", issued to Baker et al.; 4) U.S. Pat. No. 5,291,535 entitled "METHOD AND APPARATUS FOR DETECTING EXCESS/INSUFFICIENT SOLDER DEFECTS", issued to Baker et al.; 5) U.S. Pat. No. 5,621,811 entitled "LEARNING METHOD AND APPARATUS FOR DETECTING AND CONTROLLING SOLDER DEFECTS", issued to Roder et al.; 6) U.S. Pat. No. 5,561,696 "METHOD & APPARATUS FOR INSPECTING ELECTRICAL CONNECTIONS", issued to Adams et al.; 7) U.S. Pat. No. 5,199,054 entitled "METHOD AND APPARATUS FOR HIGH RESOLUTION INSPECTION OF ELECTRONIC ITEMS", issued to Adams et al.; 8) U.S. Pat. No. 5,259,012 entitled "LAMINOGRAPHY SYSTEM AND METHOD WITH ELECTROMAGNETICALLY DIRECTED MULTIPATH RADIATION SOURCE", issued to Baker et al.; 9) U.S. Pat. No. 5,583,904 entitled "CONTINUOUS LINEAR SCAN LAMINOGRAPHY SYSTEM AND METHOD", issued to Adams; and 10) U.S. Pat. No. 5,687,209 entitled "AUTOMATIC WARP COMPENSATION FOR LAMINOGRAPHIC CIRCUIT BOARD INSPECTION", issued to Adams. The entirety of each of the above referenced patents is hereby incorporated herein by reference.

Laminography techniques are widely used to produce cross sectional images of selected planes within objects. Conventional laminography requires a coordinated motion of any two of three main components comprising a laminography system, that is, a radiation source, an object being inspected, and a detector. The coordinated motion of the two components can be in any of a variety of patterns including but not limited to: linear, circular, elliptical or random patterns. Regardless of which pattern of coordinated motion is selected, the configuration of the source, object, and detector is such that any point in the object plane is always projected to the same point in the image plane and any point outside the object plane is projected to a plurality of points in the image plane during a cycle of the pattern motion. In this manner, a cross sectional image of the desired plane within the object is formed on the detector. The images of other planes within the object experience movement with respect to the detector thus creating a blur background on the detector upon which is superimposed the sharp cross sectional image of the desired focal plane within the object.

An example of a laminography system using a circular scan is described in U.S. Pat. No. 4,926,452 entitled "AUTOMATED LAMINOGRAPHY SYSTEM FOR INSPECTION OF ELECTRONICS", issued to Baker et al. This patent describes a continuous circular scan laminography system wherein the object remains stationary while the X-ray source and detector move in a coordinated circular pattern. The moving X-ray source comprises a microfocus X-ray tube wherein an electron beam is deflected in a circular scan pattern onto an anode target. The resulting motion of the X-ray source is synchronized with a rotating X-ray detector that converts the X-ray shadowgraph into an optical image so as to be viewed and integrated in a stationary video camera, thus forming a cross sectional image of the object. A computer system controls an automated positioning system that supports the item under inspection and moves successive areas of interest into view. In order to maintain high image quality, a computer system also controls the synchronization of the electron beam deflection and rotating optical system, making adjustments for inaccuracies of the mechanics of the system.

An example of a laminography system using a linear scan is described in U.S. Pat. No. 5,583,904 entitled "CONTINUOUS LINEAR SCAN LAMINOGRAPHY SYSTEM AND METHOD", issued to Adams. This patent describes an improved laminography system that allows generation of high speed and high resolution X-ray laminographs by using a continuous scan method with two or more linear detectors and one or more collimated X-ray sources. Discrete shadowgraph X-ray images, with different viewing angles, are generated by each detector. The discrete X-ray images are then combined by a computer to generate laminographic images of different planes in the object under test, or analyzed in such a manner as to derive useful data about the object under test.

In one embodiment, the linear scanning laminography system does not require any motion of the source or detectors, but simply a coordinated linear motion of the object under test. Higher speed is achieved over conventional laminography systems due to the continuous linear nature of the scan and the ability to generate any plane of data in the object under test without having to rescan the object.

In some configurations, cross sectional images for any plane in the object under test may be formed from the data acquired in a single scan. This may be accomplished by combining, e.g., within the data memory of a computer, two or more individual shadowgraph images that were formed during a single scan having coordinated positioning of two of the three main components comprising the inspection system, that is, a source, an object, and a detector. The individual shadowgraph images are combined within the computer memory such that any point in the object focal plane in one individual image is always combined with the same point in the object focal plane of another individual image, this other individual image consisting of a different angular view of the same object. Thus, mathematically shifting the pixel combinations of the multiple individual images has the result of changing the location of the focal plane in the object. For example, the multiple discrete shadowgraph images produced during a single linear scan (as described in U.S. Pat. No. 5,583,904, discussed above) or multiple discrete shadowgraph images produced during a single circular scan by a system such as that described in U.S. Pat. No. 4,926,452 above, may be combined to form a cross sectional image for any selected plane within the test object. Thus, this method of generating a cross sectional image of an object has the advantage over moving and blurring methods in that from one set of shadowgraph images, multiple cross sectional images of different focal planes may be formed. This technique has been called digital tomosynthesis, synthetic laminography, or computerized synthetic cross sectional imaging.

The cross sectional imaging techniques described above are currently used in a wide range of applications including medical and industrial X-ray imaging. Laminography is particularly well suited for inspecting objects which comprise several layers having distinguishable features within each layer. However, some previous laminography systems which produce such cross sectional images typically experience shortcomings in resolution and/or speed of inspection. For example, consider inspection of solder joints for electronic assemblies in a production environment. There are many solder joints to be inspected, and the required inspection time is short. Ideally, the inspection process is in real time, as part of a feedback control system for the manufacturing process. In many manufacturing environments there is a need to verify the integrity of thousands of solder joints within one minute or less. As electronic circuits become more complex and smaller, the size of the solder connections become smaller and the number of solder connections per unit area on the circuit boards increases. In order to keep pace with these changes, solder joint inspection systems must achieve higher resolutions at increased inspection speeds, i.e., decreased time per individual connection.

In general, the above discussed radiographic and laminographic techniques for inspecting solder connections involve various trade-offs such as image quality (approximations, noise, blurring, and artifacts) versus computation time and difficulty of obtaining the required views. Thus, there is an ongoing need for economical systems with improved computation speed while providing suitable image quality.

Accordingly, several objects and advantages of the present invention are directed to improved means for achieving high speed and high resolution cross sectional imaging for the inspection of various objects, including electrical connections.

SUMMARY OF THE INVENTION

One configuration of the present invention comprises a greatly improved computerized laminography system based on a linear scan geometry which uses an electronically scanned detector for high speed, high resolution inspection. It is expected that the electronic linear scan laminography system of the present invention, also referred to herein as an "electronic planar laminography" (EPL) system, will meet or exceed the requirements for circuit board inspections for the next five to ten years. This includes the inspection requirements for surface mount technology (SMT) based solder joints on loaded printed circuit boards (PCBs). In some configurations, the system does not require mechanical motion of the X-ray detector, the X-ray source or the object being inspected, i.e., the object remains stationary during a coordinated electronic scan of the X-ray detector and the X-ray source. In other configurations, the system does not require mechanical motion of the X-ray detector or the X-ray source. i.e., the source of X-rays remains stationary while the object moves in coordination with an electronic scan of the X-ray detector. In some configurations which use a scanning X-ray source, the X-ray source may be scanned either electronically or mechanically, however, in either case, X-ray source movement is coordinated with an electronically scanned X-ray detector. The present invention provides better resolution and is faster than previous laminography systems for the inspection of electrical connections on a circuit board.

The improved speed and resolution provided by the present invention will be required to meet the future inspection needs of the electronic industry. For example, based upon current process trends, it is expected that future developments in surface mount manufacturing technology will require inspection systems having up to 7x resolution increase and 10x speed improvement over inspection systems currently available. These improvements will be necessary in order to meet the beat rates of high-volume manufacturing lines and to accommodate inspection of new flip-chip technologies (see "National Electronics Manufacturing Technology Roadmaps", December 1998, National Electronics Manufacturing Initiative (NEMI), Inc., 2214 Rock Hill Road, Suite 110, Herndon, Va., 20170-4214.). Currently available circular scan laminography machines are capable of approximately 8 lp/mm to 30 lp/mm resolution (at about 10% modulation). Inspection rates vary depending upon the application, but in general range from about 30 seconds to a few minutes per panel, i.e. circuit board. Therefore, a 7x resolution and 10x speed improvement suggests that future architectures should be capable of 60 lp/mm to 200 lp/mm resolution and total inspection times on the order of a few to tens of seconds.

Using currently available components, i.e., detectors, X-ray sources, computers, etc, cost effective configurations of the electronic planar laminography (i.e., electronic linear scan laminography) system described herein achieve a resolution of approximately 80 lp/mm. While this is short of the 200 lp/mm long term goal, it is still sufficient for a large number of inspection tasks. Additionally, the basic architecture of the electronic planar laminography system of the present invention may be used to construct a system capable of achieving the 200 lp/mm long term goal, however, the costs of the components for such a system is presently not cost effective for most applications. However, as the technologies improve, the performance of components (i.e., detectors, X-ray sources, computers, etc) typically improve and the costs decrease, thus improving the cost effectiveness of a 200 lp/mm electronic planar laminography system according to the present invention. Other configurations of the electronic planar laminography system described herein have performance parameters similar to the currently available circular scan laminography machines and are capable of inspecting the majority of presently existing components. The analysis of the various configurations of the electronic planar laminography invention presented herein show that resolution, speed, and cost are orthogonal parameters that must be appropriately balanced to address the particular needs of any given application. In other words, there is most likely no "one-size-fits-all" solution.

In summary, the present invention improves both throughput and resolution over currently available linear and circular scan designs, while additionally eliminating mechanical motion of many system components, e.g, the scintillator. In place of a rotating scintillator, the present invention uses an X-ray detector array operating in a time-domain integration (TDI) mode, e.g. a phosphor-coupled-to-CCD array or equivalent gas or solid-state detectors capable of detecting X-rays in a time-domain integration (TDI) mode. While linear scan laminography has existed for many years, the notion of using time-domain integration to implement the detector motion electronically is a new idea. This new technique is referred to herein as "electronic planar laminography".

The time-domain integration (TDI) mode for operation of the X-ray detector as utilized in the present invention for an electronic planar laminography system is distinguished from the previously discussed similar techniques used in more traditional applications of CCDs and referred to as "time-delay-and-integration" (also abbreviated TDI). None of the previously discussed references which utilize the "time-delay-and-integration" (TDI) mode of CCD operation disclose or suggest a unique feature of the present invention wherein the electronic scan of an X-ray detector in a "time-domain integration" mode is coordinated with the motion of a scanning X-ray source in a manner which results in the production of a laminographic cross sectional image of a cutting plane of an object by the X-ray detector.

Included herein in the description of the present invention are: 1) a summary of benefits of electronic planar laminography, including: a) a completely electronic detector; b) system throughput enhancement; and c) image acquisition flexibiltiy; 2) a general discussion of the scan geometry; 3) an estimation of the signal-to-noise ratio (SNR) for this type of architecture; and 4) examples of several specific system designs which outline performance gains in both throughput and resolution.

COMPLETELY ELECTRONIC DETECTOR

Usage of an electronic X-ray detector with a time domain integration readout synchronized to an X-ray source scan to produce laminographic images is a new idea. The detector technology is completely electronic as opposed to many current systems which utilize a mechanically rotating scintillator. With an electronic detector, many of the requirements for mechanical components in the imaging chain are removed. This results in a higher level of reliability and reduced maintenance requirements.

SYSTEM THROUGHPUT ENHANCEMENT

The geometries of the present invention described herein result in much higher system throughputs than it is currently possible to obtain. Furthermore, this throughput is attained with a higher resolution than that available with many current systems. This higher throughput and resolution can be achieved with a lower frame rate, which means that motion control requirements for the system may also be relaxed, thus resulting in lower cost designs.

IMAGE ACQUISITION FLEXIBILITY

Since the present invention is directed to a time-domain integration (TDI) X-ray imaging architecture useful for acquiring cross-sectional X-ray images, the approaches described herein predominantly use laminographic imaging techniques. However, the architecture is flexible enough to accommodate additional modes including two-dimensional radiography and cross-sectional imaging with digital reconstruction techniques. Thus, the same detector and geometry used in the present invention for planar laminography may also be controlled via software to deliver not only laminographic images, but also direct radiography, tomosynthesis, and tomographic images. Although limited tomosynthesis and tomography capabilities could be incorporated into the currently available circular scan design machines (e.g., the machine described in U.S. Pat. No. 4,926,452), image projections would be required to lie along the circular path traversed by the detector. In the present invention, random projection patterns are easily made with the electronic detector system. Additionally, direct radiography is not possible with many of the presently available circular scan machines, but is easily implemented with the electronic detector of the present invention. Finally, other forms of laminography, including circular laminography, may be achieved with the electronic detector design of the present invention. The image acquisition flexibility of the present invention allows for tailoring of the imaging mode to best fit a particular application. For example, direct radiography for single sided circuit boards, laminography for general components on double sided circuit boards, and tomography for flip chips may all be used interchangeably.

In a first aspect, the present invention includes an apparatus for producing a laminographic cross sectional image of a cutting plane of an object comprising: a scanning X-ray source; an X-ray detector positioned to receive X-rays from the scanning X-ray source which have passed through the object, the X-ray detector comprising: a plurality of X-ray sensitive elements forming an array wherein each X-ray sensitive element is adapted to sense and generate an X-ray intensity signal value corresponding to the intensity of X-rays received thereon such that the X-ray intensity signal value on any specific X-ray sensitive element is indicative of the total intensity of X-rays received by that specific X-ray sensitive element; and connections between the X-ray sensitive elements adapted to allow the X-ray intensity signal values to be shifted from X-ray sensitive element to X-ray sensitive element of the array in response to shift signals corresponding to a first timing pattern such that the X-ray intensity signal values of individual X-ray sensitive elements represent an integration of X-ray intensities received at a plurality of X-ray sensitive element locations as the X-ray intensity signal values shift from X-ray sensitive element to X-ray sensitive element in response to the first timing pattern; and a control system which coordinates positioning of the scanning X-ray source with the shifting of the X-ray sensitive element X-ray intensity signal values in accordance with the first timing pattern thereby accumulating data which is representative of a laminographic cross sectional image of a first cutting plane of the object. In some configurations, the X-ray detector further responds to a second timing pattern such that the X-ray intensity signal values of individual X-ray sensitive elements represent an integration of X-ray intensities received at the plurality of X-ray sensitive element locations as the X-ray intensity signal values shift from X-ray sensitive element to X-ray sensitive element in response to the second timing pattern; and the control system coordinates positioning of the scanning X-ray source with the shifting of the X-ray sensitive element X-ray intensity signal values in accordance with the second timing pattern thereby accumulating data which is representative of a laminographic cross sectional image of a second cutting plane of the object. In some configurations, the first timing pattern comprises a first X-ray source scan rate and a first X-ray detector scan rate; and the second timing pattern comprises a second X-ray source scan rate and a second X-ray detector scan rate. In some configurations, the first X-ray source scan rate and the second X-ray source scan rate are substantially equal. In some configurations, the first X-ray detector scan rate and the second X-ray detector scan rate are substantially equal. In some configurations, the X-ray detector further responds to a radiographic timing pattern which causes the X-ray intensity signal values of individual X-ray sensitive elements to remain stationary with respect to the array; and the control system positions the scanning X-ray source at a stationary location such that the X-ray detector accumulates data which is representative of a conventional X-ray shadowgraph image of the object in accordance with the radiographic timing pattern. In some configurations, the X-ray detector further responds to a tomographic timing pattern such that the X-ray intensity signal values of individual X-ray sensitive elements are collected in accordance with a tomographic pattern; and the control system coordinates positioning of the scanning X-ray source with the shifting of the X-ray sensitive element X-ray intensity signal values in accordance with the tomographic timing pattern thereby accumulating data from which a digital reconstruction of a tomographic cross sectional image of the object may be reconstructed. In some configurations, the X-ray detector further responds to a tomosynthesis timing pattern such that the X-ray intensity signal values of individual X-ray sensitive elements are collected in accordance with a tomosynthesis pattern; and the control system coordinates positioning of the scanning X-ray source with the shifting of the X-ray sensitive element X-ray intensity signal values in accordance with the tomosynthesis timing pattern thereby accumulating data from which a digital reconstruction of a tomosynthesis cross sectional image of the object may be reconstructed. In some configurations, the scanning X-ray source follows a linear scan direction. In some configurations, the scanning X-ray source follows a circular scan direction. In some configurations, the scanning X-ray source follows a scan direction determined by a grid. In some configurations, the X-ray detector further comprises an X-ray scintillator which converts X-rays to light and a charged coupled device (CCD) which receives and detects the light produced by the X-ray scintillator. In some configurations, the X-ray detector further comprises a solid state X-ray detector array which receives X-rays and produces electrical signals in response to receiving X-rays. In some configurations, the X-ray detector further comprises a gas detector which receives X-rays and produces electrical signals in response to receiving X-rays.

A second aspect of the present invention includes an apparatus for producing a laminographic cross sectional image of a cutting plane of a stationary object comprising: a scanning X-ray source; an X-ray detector positioned to receive X-rays from the scanning X-ray source which have passed through the stationary object, the X-ray detector comprising: a plurality of X-ray sensitive regions forming an array wherein each X-ray sensitive region is adapted to sense X-rays and generate X-ray intensity signal values corresponding to the intensity of X-rays received thereon; and connections between the X-ray sensitive regions adapted to allow the X-ray intensity signal values to be shifted from X-ray sensitive region to X-ray sensitive region of the array in response to shift signals corresponding to a first timing pattern such that the X-ray intensity signal values of individual X-ray sensitive regions represent an integration of X-ray intensities received at a plurality of X-ray sensitive region locations as the X-ray intensity signal values shift from X-ray sensitive region to X-ray sensitive region in response to the first timing pattern; and a control system which coordinates positioning of the scanning X-ray source with the plurality of the X-ray sensitive regions of the X-ray detector such that: first X-ray image data of the stationary object is collected by a first X-ray sensitive region of the X-ray detector when the X-ray source is located at a first position wherein a first angular relationship is formed between the X-ray source at the first position and the first X-ray sensitive region of the X-ray detector during collection of the first X-ray image data; second X-ray image data of the stationary object is formed on a second X-ray sensitive region of the X-ray detector when the X-ray source is located at a second position wherein a second angular relationship is formed between the X-ray source at the second position and the second X-ray sensitive region of the X-ray detector during collection of the second X-ray image data;

and the first X-ray image data of the stationary object at the first angular configuration and the second X-ray image data of the stationary object at the second angular configuration are combined thereby creating data representative of a laminographic cross sectional image of a first cutting plane of the stationary object. In some configurations, the X-ray detector further responds to a second timing pattern such that the X-ray intensity signal values of individual X-ray sensitive regions represent an integration of X-ray intensities received at the plurality of X-ray sensitive region locations as the X-ray intensity signal values shift from X-ray sensitive region to X-ray sensitive region in response to the second timing pattern; and the control system coordinates positioning of the scanning X-ray source with the plurality of the X-ray sensitive regions of the X-ray detector in accordance with the second timing pattern such that: third X-ray image data of the stationary object is formed on the second X-ray sensitive region of the X-ray detector when the X-ray source is located at a third position wherein a third angular relationship is formed between the X-ray source at the third position and the second X-ray sensitive region of the X-ray detector during collection of the third X-ray image data; and the first X-ray image data of the stationary object at the first angular configuration and the third X-ray image data of the stationary object at the third angular configuration are combined thereby creating data which is representative of a laminographic cross sectional image of a second cutting plane of the stationary object. In some configurations, the first timing pattern comprises a first X-ray source scan rate and a first X-ray detector scan rate; and the second timing pattern comprises a second X-ray source scan rate and a second X-ray detector scan rate. In some configurations, the X-ray detector further responds to a tomographic timing pattern such that the X-ray intensity signal values of individual X-ray sensitive regions are collected in accordance with a tomographic pattern; and the control system coordinates positioning of the scanning X-ray source with the shifting of the X-ray sensitive region X-ray intensity signal values in accordance with the tomographic pattern thereby accumulating data from which a digital reconstruction of a tomographic cross sectional image of the object may be reconstructed. In some configurations, the scanning X-ray source follows a linear scan direction; the X-ray detector further comprises a detector array wherein individual X-ray sensitive elements comprising the detector array are arranged in a plurality of linear rows and linear columns, the linear rows being substantially perpendicular to the X-ray source linear scan direction and the linear columns being substantially parallel to the X-ray source linear scan direction; and regions of the stationary object being imaged are linear regions which are substantially perpendicular to the X-ray source linear scan direction and substantially parallel to the linear rows of the detector array. In some configurations, the X-ray detector array further comprises an X-ray scintillator which converts X-rays to light and a charged coupled device (CCD) which receives and detects the light produced by the X-ray scintillator.

A third aspect of the present invention includes an apparatus for producing a laminographic cross sectional image of a cutting plane of a stationary object comprising: a scanning X-ray source which scans along a first linear path; an X-ray detector array positioned to receive X-rays from the scanning X-ray source which have passed through the object, the X-ray detector array comprising: a plurality of adjacent X-ray sensitive rows which are substantially perpendicular to the X-ray source first linear path wherein each X-ray sensitive row is adapted to sense X-rays and generate X-ray intensity signal values corresponding to the intensity of X-rays received thereon; and connections between the adjacent X-ray sensitive rows adapted to allow the X-ray intensity signal values to be shifted from X-ray sensitive row to X-ray sensitive row of the X-ray detector array in response to shift signals corresponding to a first timing pattern such that the X-ray intensity signal values of individual X-ray sensitive rows represent multiple angle integrations of X-ray intensities received at a plurality of X-ray sensitive row locations at a plurality of angular orientations of the scanning X-ray source locations and the X-ray detector X-ray sensitive row locations as the X-ray intensity signal values shift from X-ray sensitive row to X-ray sensitive row in response to the first timing pattern; and a control system which coordinates positioning of the scanning X-ray source with the shifting of the X-ray intensity signal values of the X-ray detector in accordance with the first timing pattern thereby creating data representative of a laminographic cross sectional image of a first cutting plane of the stationary object. In some configurations, the X-ray detector further responds to a second timing pattern such that the X-ray intensity signal values of individual X-ray sensitive rows represent an integration of X-ray intensities received at the plurality of X-ray sensitive row locations as the X-ray intensity signal values shift from X-ray sensitive row to X-ray sensitive row in response to the second timing pattern; and the control system coordinates positioning of the scanning X-ray source with the shifting of the X-ray intensity signal values in accordance with the second timing pattern thereby accumulating data which is representative of a laminographic cross sectional image of a second cutting plane of the object. In some configurations, the first timing pattern comprises a first X-ray source scan rate and a first X-ray detector scan rate; and the second timing pattern comprises a second X-ray source scan rate and a second X-ray detector scan rate. In some configurations, the X-ray detector further responds to a tomographic timing pattern such that the X-ray intensity signal values are collected in accordance with a tomographic pattern; and the control system coordinates positioning of the scanning X-ray source with the shifting of the X-ray intensity signal values in accordance with the tomographic pattern thereby accumulating data from which a digital reconstruction of a tomographic cross sectional image of the object may be reconstructed. In some configurations, the X-ray detector array further comprises an X-ray scintillator which converts X-rays to light and a charged coupled device (CCD) which receives and detects the light produced by the X-ray scintillator.

A fourth aspect of the present invention includes an apparatus for producing a laminographic cross sectional image of a first cutting plane of an object comprising: a scanning X-ray source; a scanning X-ray detector array positioned to receive X-rays from the scanning X-ray source which have passed through the object, the scanning X-ray detector comprising: a plurality of X-ray sensitive elements adapted to sense and generate X-ray intensity signal values corresponding to the intensity of X-rays received thereon, the X-ray intensity signal values thereby representing an X-ray image of a portion of the object; and connections between the X-ray sensitive elements adapted to allow the X-ray intensity signal values representing X-ray images to be shifted from X-ray sensitive element to X-ray sensitive element of the scanning X-ray detector array in response to shift signals corresponding to a first timing pattern such that the X-ray intensity signal values of individual X-ray sensitive elements correspond to an integration of X-ray intensities received at a plurality of X-ray sensitive element locations and a plurality of angular orientations of the X-ray source and the scanning X-ray detector X-ray sensitive element locations as the X-ray intensity signal values representing X-ray images shift from X-ray sensitive element to X-ray sensitive element in response to the first timing pattern; and a control system which coordinates positioning of the scanning X-ray source with the shifting of the X-ray sensitive element X-ray intensity signal values in accordance with the first timing pattern such that multiple angular image projections of the first cutting plane of the object are accumulated by the scanning X-ray detector array wherein any point in the first cutting plane of the object is projected to approximately the same shifted point of the scanning X-ray detector array X-ray sensitive elements and any point outside the first cutting plane is projected to a plurality of shifted points of the scanning X-ray detector array X-ray sensitive elements during a cycle of the first timing pattern thereby accumulating data which is representative of a laminographic cross sectional image of the first cutting plane of the object. In some configurations, the scanning X-ray detector array further responds to a second timing pattern such that the X-ray intensity signal values of individual X-ray sensitive elements represent an integration of X-ray intensities received at the plurality of X-ray sensitive element locations and the plurality of angular orientations of the X-ray source and the scanning X-ray detector array X-ray sensitive element locations as the X-ray intensity signal values representing X-ray images shift from X-ray sensitive element to X-ray sensitive element in response to the second timing pattern; and the control system coordinates positioning of the scanning X-ray source with the shifting of the X-ray sensitive element X-ray intensity signal values in accordance with the second timing pattern such that multiple angular image projections of a second cutting plane of the object are accumulated by the scanning X-ray detector array wherein any point in the second cutting plane of the object is projected to approximately the same shifted point of the scanning X-ray detector array X-ray sensitive elements and any point outside the second cutting plane is projected to a plurality of shifted points of the scanning X-ray detector array X-ray sensitive elements during a cycle of the second timing pattern thereby accumulating data which is representative of a laminographic cross sectional image of a second cutting plane of the object. In some configurations, the first timing pattern comprises a first X-ray source scan rate and a first X-ray detector scan rate; and the second timing pattern comprises a second X-ray source scan rate and a second X-ray detector scan rate. In some configurations, the scanning X-ray detector array further responds to a tomographic timing pattern such that the X-ray intensity signal values of individual X-ray sensitive elements are collected in accordance with a tomographic pattern; and the control system coordinates positioning of the scanning X-ray source with the shifting of the X-ray sensitive element X-ray intensity signal values in accordance with the tomographic pattern thereby accumulating data from which a digital reconstruction of a tomographic cross sectional image of the object may be reconstructed. In some configurations, the scanning X-ray source follows a linear scan direction. In some configurations, the scanning X-ray detector array further comprises an X-ray scintillator which converts X-rays to light and a charged coupled device (CCD) which receives and detects the light produced by the X-ray scintillator.

A fifth aspect of the present invention includes an apparatus for producing a laminographic cross sectional image of a cutting plane of an object comprising: a stationary X-ray source; a moving support for the object; an X-ray detector positioned to receive X-rays from the stationary X-ray source which have passed through the object, the X-ray detector comprising: a plurality of X-ray sensitive elements forming an array wherein each X-ray sensitive element is adapted to sense and generate an X-ray intensity signal value corresponding to the intensity of X-rays received thereon such that the X-ray intensity signal value on any specific X-ray sensitive element is indicative of the total intensity of X-rays received by that specific X-ray sensitive element; and connections between the X-ray sensitive elements adapted to allow the X-ray intensity signal values to be shifted from X-ray sensitive element to X-ray sensitive element of the array in response to shift signals corresponding to a first timing pattern such that the X-ray intensity signal values of individual X-ray sensitive elements represent an integration of X-ray intensities received at a plurality of X-ray sensitive element locations as the X-ray intensity signal values shift from X-ray sensitive element to X-ray sensitive element in response to the first timing pattern; and a control system which coordinates positioning of the moving support with the shifting of the X-ray sensitive element X-ray intensity signal values in accordance with the first timing pattern thereby accumulating data which is representative of a laminographic cross sectional image of a first cutting plane of the object. In some configurations, the X-ray detector further responds to a second timing pattern such that the X-ray intensity signal values of individual X-ray sensitive elements represent an integration of X-ray intensities received at the plurality of X-ray sensitive element locations as the X-ray intensity signal values shift from X-ray sensitive element to X-ray sensitive element in response to the second timing pattern; and the control system coordinates positioning of the moving support with the shifting of the X-ray sensitive element X-ray intensity signal values in accordance with the second timing pattern thereby accumulating data which is representative of a laminographic cross sectional image of a second cutting plane of the object. In some configurations, the first timing pattern comprises a first moving support scan rate and a first X-ray detector scan rate; and the second timing pattern comprises a second moving support scan rate and a second X-ray detector scan rate. In some configurations, the X-ray detector further responds to a tomographic timing pattern such that the X-ray intensity signal values of individual X-ray sensitive elements are collected in accordance with a tomographic pattern; and the control system coordinates positioning of the moving support with the shifting of the X-ray sensitive element X-ray intensity signal values in accordance with the tomographic timing pattern thereby accumulating data from which a digital reconstruction of a tomographic cross sectional image of the object may be reconstructed. In some configurations, the moving support follows a linear scan direction. In some configurations, the X-ray detector further comprises an X-ray scintillator which converts X-rays to light and a charged coupled device (CCD) which receives and detects the light produced by the X-ray scintillator.

A sixth aspect of the present invention includes a method for producing a laminographic cross sectional image of a cutting plane of an object comprising the steps of: scanning the object with a scanning X-ray source; detecting X-rays from the scanning X-ray source which have passed through the object with an X-ray detector, the X-ray detector comprising: a plurality of X-ray sensitive elements forming an array wherein each X-ray sensitive element is adapted to sense and generate an X-ray intensity signal value corresponding to the intensity of X-rays received thereon such that the X-ray intensity signal value on any specific X-ray sensitive element is indicative of the total intensity of X-rays received by that specific X-ray sensitive element; and connections between the X-ray sensitive elements adapted to allow the X-ray intensity signal values to be shifted from X-ray sensitive element to X-ray sensitive element of the array in response to shift signals corresponding to a first timing pattern such that the X-ray intensity signal values of individual X-ray sensitive elements represent an integration of X-ray intensities received at a plurality of X-ray sensitive element locations as the X-ray intensity signal values shift from X-ray sensitive element to X-ray sensitive element in response to the first timing pattern; and coordinating the position of the scanning X-ray source with the shifting of the X-ray sensitive element X-ray intensity signal values with a control system in accordance with the first timing pattern thereby accumulating data which is representative of a laminographic cross sectional image of a first cutting plane of the object. In some implementations of the method, the X-ray detector further responds to a second timing pattern such that the X-ray intensity signal values of individual X-ray sensitive elements represent an integration of X-ray intensities received at the plurality of X-ray sensitive element locations as the X-ray intensity signal values shift from X-ray sensitive element to X-ray sensitive element in response to the second timing pattern; and the control system coordinates positioning of the scanning X-ray source with the shifting of the X-ray sensitive element X-ray intensity signal values in accordance with the second timing pattern thereby accumulating data which is representative of a laminographic cross sectional image of a second cutting plane of the object. In some implementations of the method, the first timing pattern comprises a first X-ray source scan rate and a first X-ray detector scan rate; and the second timing pattern comprises a second X-ray source scan rate and a second X-ray detector scan rate. In some implementations of the method, the X-ray detector further responds to a tomographic timing pattern such that the X-ray intensity signal values of individual X-ray sensitive elements are collected in accordance with a tomographic pattern; and the control system coordinates positioning of the scanning X-ray source with the shifting of the X-ray sensitive element X-ray intensity signal values in accordance with the tomographic timing pattern thereby accumulating data from which a digital reconstruction of a tomographic cross sectional image of the object may be reconstructed. In some implementations of the method, the scanning X-ray source follows a linear scan direction. In some implementations of the method, the X-ray detector further comprises an X-ray scintillator which converts X-rays to light and a charged coupled device (CCD) which receives and detects the light produced by the X-ray scintillator.

A seventh aspect of the present invention includes a method for producing a laminographic cross sectional image of a cutting plane of an object comprising: providing a stationary X-ray source; providing a moving support for the object; positioning an X-ray detector to receive X-rays from the stationary X-ray source which have passed through the object, the X-ray detector comprising: a plurality of X-ray sensitive elements forming an array wherein each X-ray sensitive element is adapted to sense and generate an X-ray intensity signal value corresponding to the intensity of X-rays received thereon such that the X-ray intensity signal value on any specific X-ray sensitive element is indicative of the total intensity of X-rays received by that specific X-ray sensitive element; and connections between the X-ray sensitive elements adapted to allow the X-ray intensity signal values to be shifted from X-ray sensitive element to X-ray sensitive element of the array in response to shift signals corresponding to a first timing pattern such that the X-ray intensity signal values of individual X-ray sensitive elements represent an integration of X-ray intensities received at a plurality of X-ray sensitive element locations as the X-ray intensity signal values shift from X-ray sensitive element to X-ray sensitive element in response to the first timing pattern; and providing a control system which coordinates positioning of the moving support with the shifting of the X-ray sensitive element X-ray intensity signal values in accordance with the first timing pattern thereby accumulating data which is representative of a laminographic cross sectional image of a first cutting plane of the object. In some implementations of the method, the X-ray detector further responds to a second timing pattern such that the X-ray intensity signal values of individual X-ray sensitive elements represent an integration of X-ray intensities received at the plurality of X-ray sensitive element locations as the X-ray intensity signal values shift from X-ray sensitive element to X-ray sensitive element in response to the second timing pattern; and the control system coordinates positioning of the moving support with the shifting of the X-ray sensitive element X-ray intensity signal values in accordance with the second timing pattern thereby accumulating data which is representative of a laminographic cross sectional image of a second cutting plane of the object. In some implementations of the method, the first timing pattern comprises a first moving support scan rate and a first X-ray detector scan rate; and the second timing pattern comprises a second moving support scan rate and a second X-ray detector scan rate. In some implementations of the method, the X-ray detector further responds to a tomographic timing pattern such that the X-ray intensity signal values of individual X-ray sensitive elements are collected in accordance with a tomographic pattern; and the control system coordinates positioning of the moving support with the shifting of the X-ray sensitive element X-ray intensity signal values in accordance with the tomographic timing pattern thereby accumulating data from which a digital reconstruction of a tomographic cross sectional image of the object may be reconstructed. In some implementations of the method, the moving support follows a linear scan direction. In some implementations of the method, the X-ray detector further comprises an X-ray scintillator which converts X-rays to light and a charged coupled device (CCD) which receives and detects the light produced by the X-ray scintillator.

These and other characteristics of the present invention will become apparent through reference to the following detailed description of the preferred embodiments and accompanying drawings.

BRIEF DESCRIPTION OF THE DRAWINGS

FIG. 2e shows a conventional, two-dimensional X-ray projection image of the object in FIG. 2a.

FIG. 3a is a diagrammatic cross-sectional view of a base-line circular scan laminography system for circuit board inspection showing how the laminographic image is formed and viewed by a camera.

FIG. 3b shows a top view enlargement of an inspection region shown in FIG. 3a.

FIG. 3c is a perspective view of the base-line circular scan laminography system for circuit board inspection shown in FIG. 3a.

FIG. 7 is a block diagram of an m x n multi-linear array adaptable for use as an X-ray detector.

FIGS. 8a–8m illustrate the manner in which an electronic linear scan laminographic system having a synchronously scanned X-ray source and X-ray detector produces a cross sectional laminographic image of a cutting plane of an object.

FIGS. 11a–11m illustrate the manner in which an electronic linear scan laminographic system having an X-ray detector which is scanned synchronously with the motion of a test object produces a cross sectional laminographic image of a cutting plane of the test object.

FIG. 13 shows a linear scan geometry for a moving source configuration of the present invention which produces a cross-sectional image of an object placed in the object plane obtained by clocking the detector array in one direction while moving the X-ray beam in the opposite direction.

FIG. 14 shows the geometry for computation of per pixel sweep angle with a moving source.

FIG. 15 shows the parameters used to find the X-ray flux on a detector pixel.

DETAILED DESCRIPTION OF THE INVENTION

CROSS-SECTIONAL IMAGE FORMATION IN A CIRCULAR SCAN LAMINOGRAPHY SYSTEM

Figure 1:
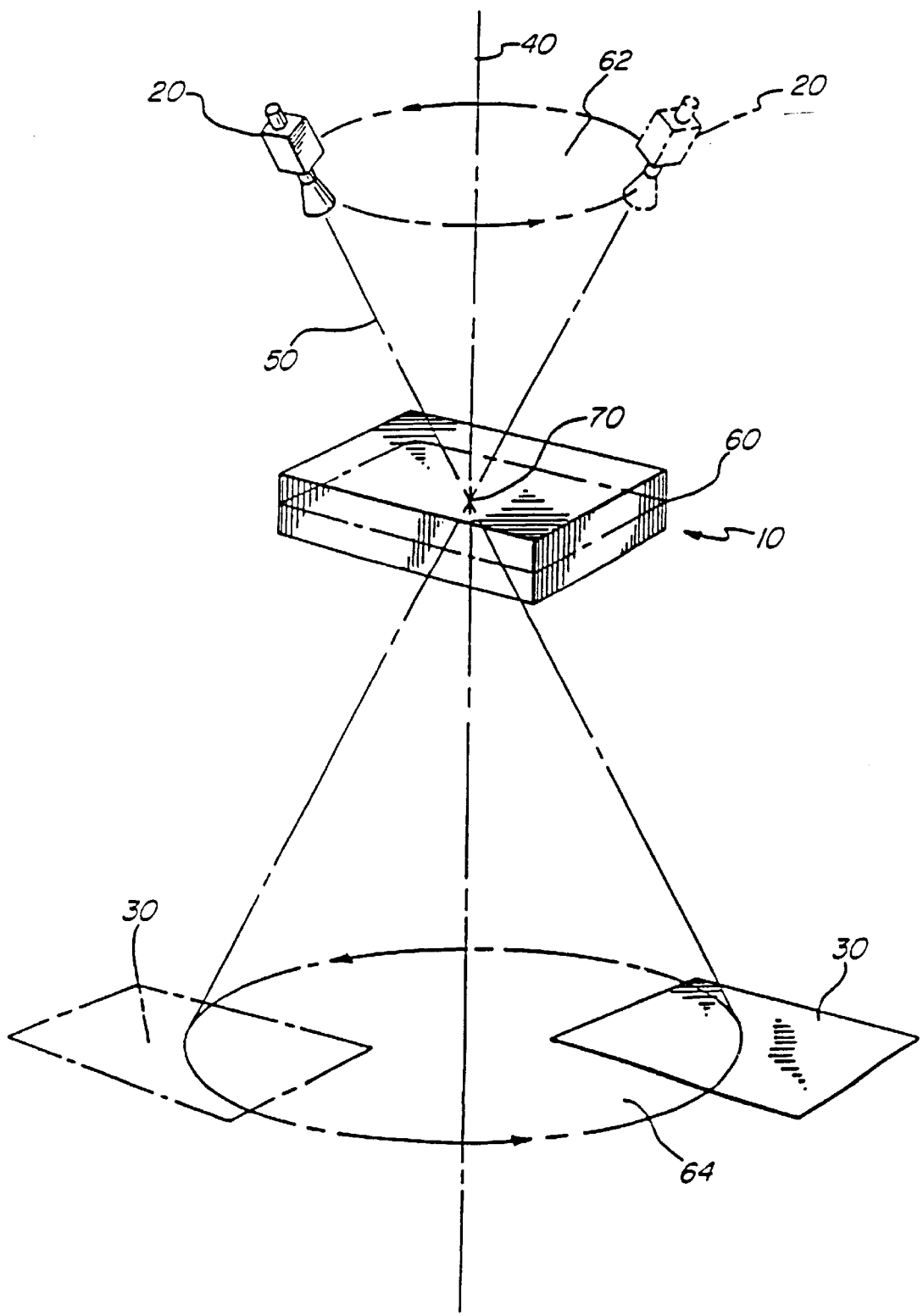
FIG. 1 is a schematic representation of a circular scan laminography system illustrating the principles of laminography.

FIG. 1 shows a schematic representation of a typical circular scan laminographic geometry commonly used for circuit board inspection. An object 10 under examination, for example, a circuit board, is held in a stationary position with respect to a source of X-rays 20 and an X-ray detector 30. Synchronous rotation of the X-ray source 20 and detector 30 about a common 30 axis 40 causes an X-ray image of the plane 60 with respect to the object 10 to be formed on the detector 30. The image plane 60 is substantially parallel to planes 62 and 64 defined by the rotation of the source 20 and detector 30, respectively. The image plane 60 is located at an intersection 70 of a central ray 50 from the X-ray source 20 and the common axis of rotation 40. This point of intersection 70 acts as a fulcrum for the central ray 50, thus causing an in-focus cross-sectional X-ray image of the object 10 at the plane 60 to be formed on detector 30 as the source and detector synchronously rotate about the intersection point 70. Structure with respect to the object 10 which lies outside of plane 60 forms a blurred X-ray image on detector 30.

In the laminographic geometry shown in FIG. 1, the axis of rotation of the radiation source 20 and the axis of rotation of the detector 30 are coaxial. However, it is not necessary that these axes of rotation of the radiation source 20 and the detector 30 be coaxial. The conditions of laminography are satisfied and a cross-sectional image of the layer 60 will be produced as long as the planes of rotation 62 and 64 are mutually parallel, and the axes of rotation of the source and the detector are mutually parallel and fixed in relationship to each other. Coaxial alignment reduces the number of constraints upon the mechanical alignment of the apparatus.

FIGS. 2a–2e show laminographs produced by the above described circular scan laminographic technique. The object 10 shown in FIG. 2a has test patterns in the shape of an arrow 81, a circle 82 and a cross 83 embedded within the object 10 in three different planes 60a, 60b and 60c, respectively.

Figure 2A:
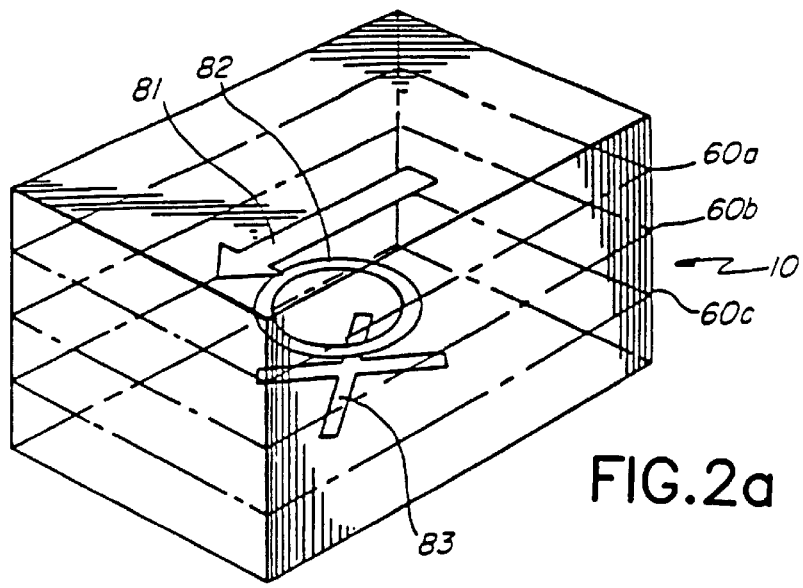
FIG. 2a shows an object having an arrow, a circle and a cross embedded in the object at three different planar locations.
Figure 2B:
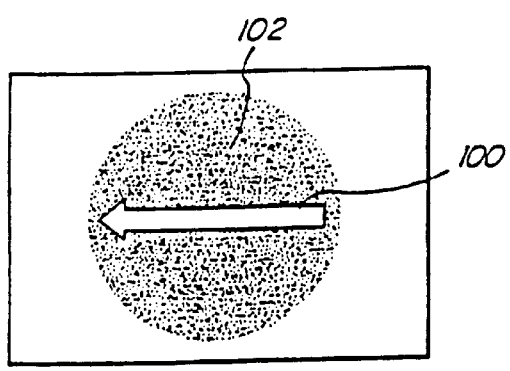
FIG. 2b shows a laminograph of the object in FIG. 2a focused on the plane containing the arrow.

FIG. 2b shows a typical laminograph of object 10 formed on detector 30 when the point of intersection 70 lies in plane 60a of FIG. 2a. An image 100 of the arrow 81 is in sharp focus, while the images of other features within the object 10, such as the circle 82 and cross 83 form a blurred region 102 which does not greatly obscure the arrow image 100.

Figure 2D:
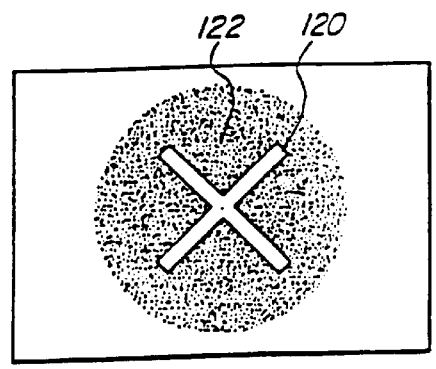
FIG. 2d shows a laminograph of the object in FIG. 2a focused on the plane containing the cross.
Figure 2C:
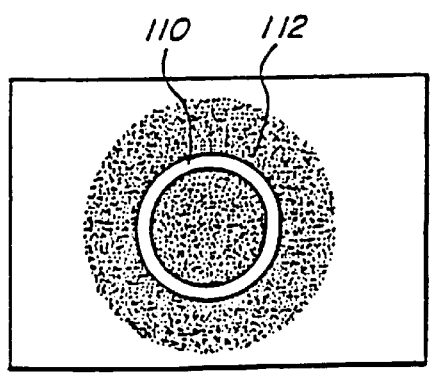
FIG. 2c shows a laminograph of the object in FIG. 2a focused on the plane containing the circle.

Similarly, when the point of intersection 70 lies in plane 60b, an image 110 of the circle 82 is in sharp focus as seen in FIG. 2c. The arrow 81 and cross 83 form a blurred region 112.

FIG. 2d shows a sharp image 120 formed of the cross 83 when the point of intersection 70 lies in plane 60c. The arrow 81 and circle 82 form a blurred region 122.

Figure 2E:
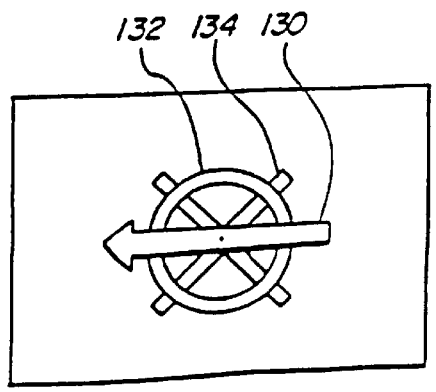

For comparison, FIG. 2e shows an X-ray shadow image of object 10 formed by conventional projection radiography techniques. This technique produces sharp images 130, 132 and 134 of the arrow 81, circle 82 and cross 83, respectively, which overlap one another. FIG. 2e vividly illustrates how multiple characteristics contained within the object 10 may create multiple overshadowing features in the X-ray image which obscure individual features of the image.

BASELINE CIRCULAR SCAN LAMINOGRAPHY SYSTEM

FIG. 3a illustrates a schematic diagram of a typical laminographic apparatus presently used for solder joint inspection. The performance of this system will be used herein as a baseline for comparison with several configurations of the present invention. As shown in FIG. 3a, an object under inspection is a printed circuit board 210 having multiple electronic components 212 mounted on the board 210 and electrically interconnected via electrical connections 214 (See FIG. 3b). Typically, the electrical connections 214 are formed of solder. However, various other techniques for making the electrical connections 214 are well know in the art and even though the invention will be described in terms of solder joints, it will be understood that other types of electrical connections 214 including, but not limited to, conductive epoxy, mechanical, and eutectic bonds may be inspected utilizing laminographic techniques. FIG. 3b, which is a top view enlargement of a region 283 of the circuit board 210, more clearly shows the components 212 and solder joints 214.

The laminographic apparatus acquires cross-sectional images of the solder joints 214 using the previously described laminographic method or other methods capable of producing equivalent cross-sectional images. The cross-sectional images of the solder joints 214 are automatically evaluated to determine their quality. Based on the evaluation, a report of the solder joint quality is presented to the user.

The laminographic apparatus, as shown in FIG. 3a, comprises an X-ray tube 200 which is positioned adjacent printed circuit board 210. The circuit board 210 is supported by a fixture 220. The fixture 220 is attached to a positioning table 230 which is capable of moving the fixture 220 and board 210 along three mutually perpendicular axes, X, Y and Z. A rotating X-ray detector 240 comprising a scintillating screen 250, a first mirror 252, a second mirror 254 and a turntable 256 is positioned adjacent the circuit board 210 on the side opposite the X-ray tube 200. A camera 258 is positioned opposite mirror 252 for viewing images reflected into the mirrors 252, 254 from scintillating screen 250. A feedback system 260 has an input connection 262 from a sensor 263 which detects the angular position of the turntable 256 and an output connection 264 to X and Y deflection coils 281 on X-ray tube 200. A position encoder 265 is attached to turntable 256. The position sensor 263 is mounted adjacent encoder 265 in a fixed position relative to the axis of rotation 40. The camera 258 is connected to a computer 270 via an input line 276. The computer 270 includes the capability to perform high speed image analysis. An output line 278 from the computer 270 connects the computer to positioning table 230.

Figure 3C:
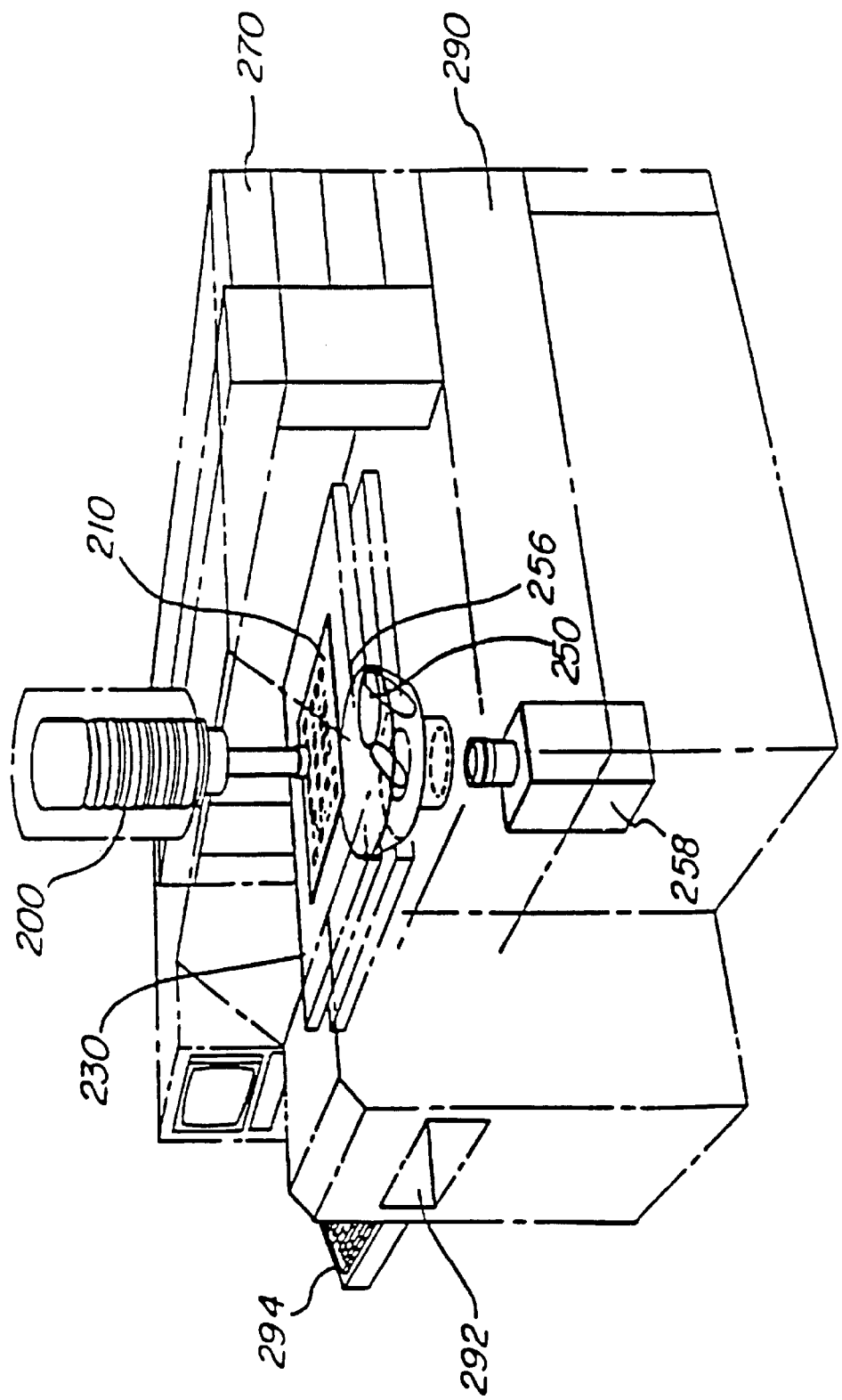

A perspective view of the laminographic apparatus is shown in FIG. 3c. In addition to the X-ray tube 200, circuit board 210, scintillating screen 250, turntable 256, camera 258, positioning table 230 and computer 270 shown in FIG. 3a, a granite support table 290, a load/unload port 292 and an operator station 294 are shown. The granite table 290 provides a rigid, vibration free platform for structurally integrating the major functional elements of the laminographic apparatus, including but not limited to the X-ray tube 200, positioning table 230 and turntable 256. The load/unload port 292 provides a means for inserting and removing circuit boards 210 from the machine. The operator station 294 provides an input/output capability for controlling the functions of the laminographic apparatus as well as for communication of inspection data to an operator.

In operation of the laminographic apparatus as shown in FIGS. 3a and 3c, high resolution, cross-sectional X-ray images of the solder joints 214 connecting components 212 on circuit board 210 are acquired using the X-ray laminographic method previously described in reference to FIGS. 1 and 2. Specifically, X-ray tube 200, as shown in FIG. 3a, comprises a rotating electron beam spot 285 which produces a rotating source 280 of X-rays 282. The X-ray beam 282 illuminates a region 283 of circuit board 210 including the solder joints 21 4 located within region 283. X-rays 284 which penetrate the solder joints 214, components 212 and board 210 are intercepted by the rotating scintillating screen 250.

Dynamic alignment of the position of the X-ray source 280 with the position of rotating X-ray detector 240 is precisely controlled by feedback system 260. The feedback system correlates the position of the rotating turntable 256 with calibrated X and Y deflection values stored in a look-up table (LUT). Drive signals proportional to the calibrated X and Y deflection values are transmitted to the steering coils 281 on the X-ray tube 200. In response to these drive signals, steering coils 281 deflect electron beam 285 to locations on an annular shaped target anode 287 such that the position of the X-ray source spot 280 rotates in synchronization with the rotation of detector 240 in the manner previously discussed in connection with FIG. 1.

X-rays 284 which penetrate the board 210 and strike scintillating screen 250 are converted to visible light 286, thus creating a visible image of a single plane within the region 283 of the circuit board 210. The visible light 286 is reflected by mirrors 252 and 254 into camera 258. Camera 258 typically comprises a low light level fast scanning CCD based camera which transmits electronic video signals corresponding to the X-ray and visible images to the computer 270 via line 276. The image analysis feature of computer 270 analyzes and interprets the image to determine the quality of the solder joints 214. Computer 270 also controls the movement of positioning table 230 and thus circuit board 210 so that different regions of circuit board 210 may be automatically positioned within inspection region 283.

The baseline circular scan laminographic apparatus shown and described with reference to FIGS. 1—3 is typical of that which is currently used to inspect solder connections. A typical apparatus of this type includes a 0.8 inch×0.8 inch field-of-view (FOV), also referred to herein as the "800 FOV". System resolution at the 800 FOV is about 8 lp/mm. Although circuit board warpage may become an issue with larger fields-of-view, there are no optical constraints preventing a machine design using larger FOVs. However, other specifications of the current design may also present FOV limitations. Additional system parameters for this baseline circular scan laminography apparatus may be found in R. Shane Fazzio, "RADIATION EXPOSURE IN A MODERN, CIRCULARLY SCANNED-BEAM LAMINOGRAPHIC X-RAY INSPECTION SYSTEM," *Journal of X-ray Science and Technology*, Vol. 8, 1998, pp. 117–133. This reference also outlines the physics of the rotating mirror imaging subsystem.

The characteristics and performance parameters of this circular scan laminographic system are used herein as a baseline for comparison with the characteristics and performance parameters of several configurations of the electronic planar laminography (i.e., electronic linear scan laminography) systems of the present invention. In general, the electronic linear scan laminography configurations of the electronic planar laminography system of the present invention achieve higher resolution and faster inspection speeds than the baseline circular scan laminographic system.

ELECTRONIC LINEAR SCAN LAMINOGRAPHY WITH A SCANNING X-RAY SOURCE AND A FIXED TEST OBJECT

Figure 4:
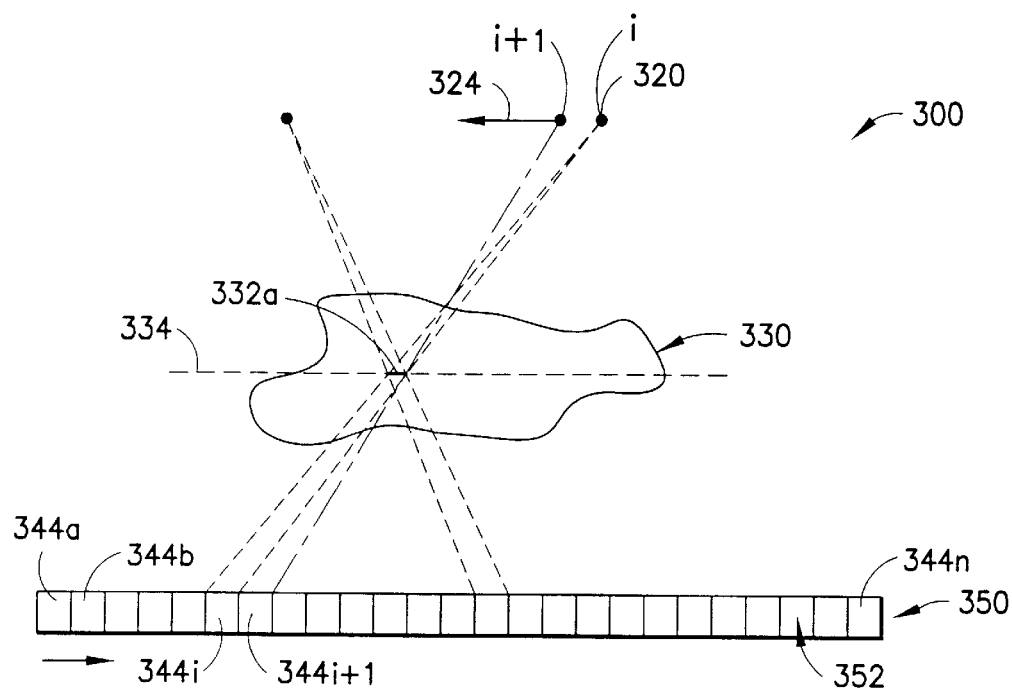
FIG. 4 is a side view illustration of an electronic planar laminography system in a configuration having a synchronously scanned X-ray source and X-ray detector in accordance with the present invention. In this configuration, the test object is stationary during the scan.
Figure 5:
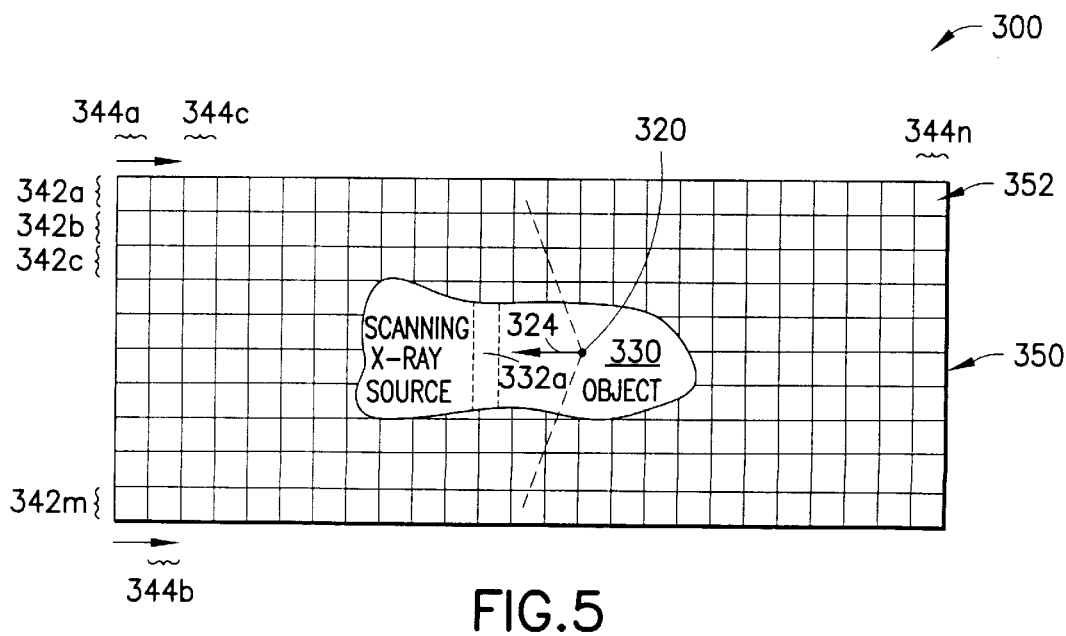
FIG. 5 is a top view illustration of the electronic planar laminography system shown in FIG. 4.
Figure 6:
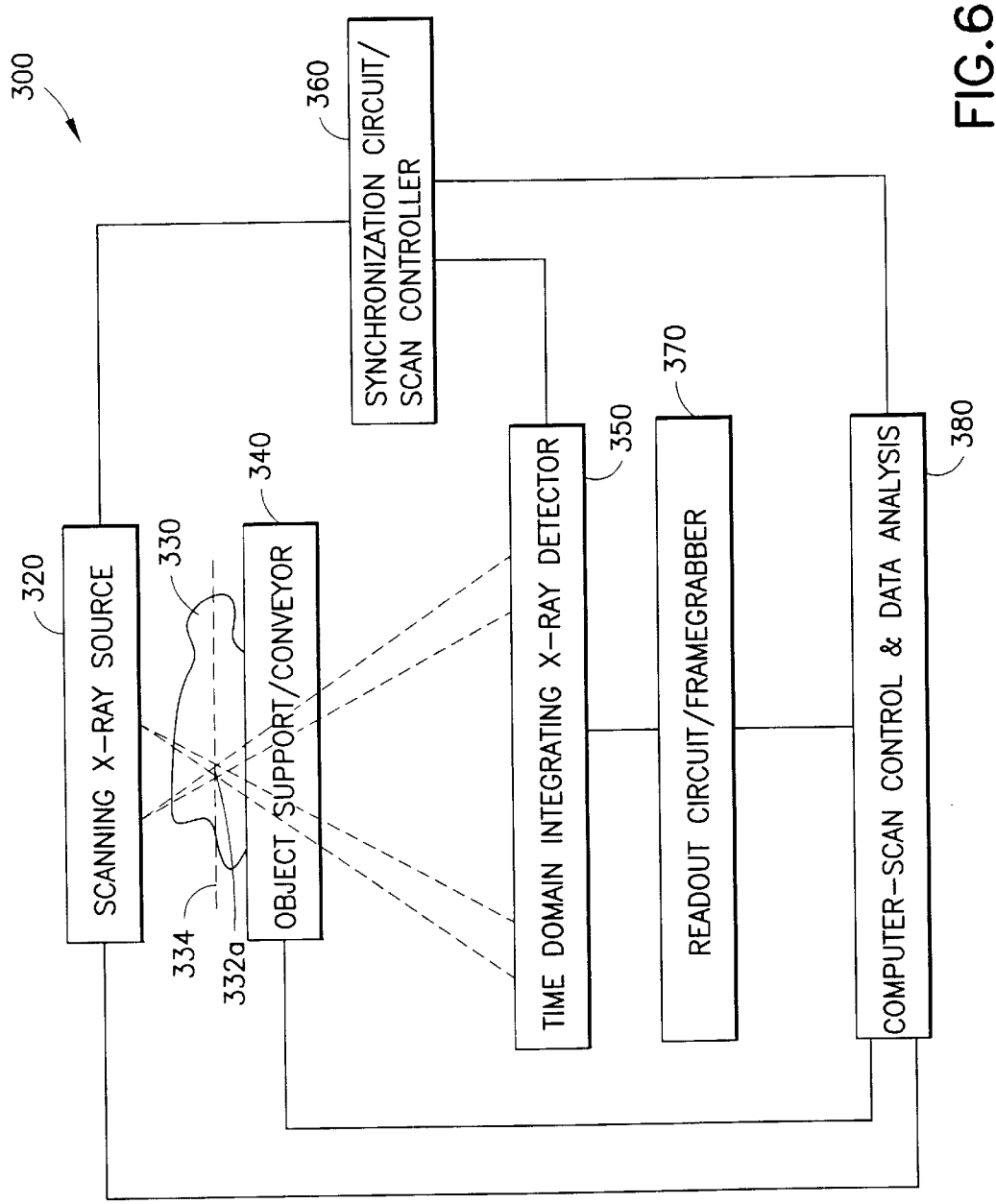
FIG. 6 is a block diagram of the electronic planar laminography system shown in FIGS. 4 and 5.

A configuration 300 of the present invention for an electronic planar laminography system using a linear scan geometry and a scanning X-ray source 320 is shown in FIGS. 4, 5 and 6. FIG. 4 shows a side view illustration of the electronic planar laminography system 300 in a configuration having a scanning X-ray source 320. FIG. 5 is a top view illustration of the electronic planar laminography system 300 shown in FIG. 4; and FIG. 6 is a block diagram of the electronic planar laminography system 300 shown in FIGS. 4 and 5. The scanning X-ray source 320 is positioned adjacent a test object 330 being inspected and moves along a linear path 324. In most applications, the linear motion of the scanning X-ray source 320 is accomplished electrically, however it may also be accomplished mechanically. The test object 330 may be supported by a positioning table 340 which is capable of moving the test object 330 to a specified position. For example, the positioning table 340 may be capable of motion along a single axis X, two mutually perpendicular axes, X and Y, three mutually perpendicular axes, X, Y and Z. angular motion or a combination of angular and linear motions, depending upon the requirements of a specific inspection. However, in the following discussion, the test object 330 is held in a stationary position and the positioning table 340 need not be present. A multi-linear array X-ray detector 350 is positioned adjacent the test object 330 on a side opposite the linear scan X-ray source 320. A synchronization circuit/scan controller 360 controls and coordinates the scanning of the linear scan X-ray source 320 and the multi-linear array X-ray detector 350. A readout circuit/framegrabber 370 controls the reading of data and image acquisition from the multi-linear array X-ray detector 350. A computer or dedicated controller 380 oversees and controls the operation of the entire system including: 1) the linear scan X-ray source 320; 2) the multi-linear array X-ray detector 350; 3) the synchronization circuit/scan controller 360; 4) the readout circuit/framegrabber 370; and, where appropriate, 5) the positioning table 340. Computer or dedicated controller 380 also has the capability to perform high speed image analysis.

OPERATION OF MULTI-LINEAR ARRAY X-RAY DETECTOR

In order to fully appreciate and understand the invention herein disclosed, it will be helpful to understand the operation of the multi-linear array X-ray detector 350. Referring to FIGS. 5 and 7, the multi-linear array X-ray detector 350 comprises a plurality of image sensing elements 352 arranged in a particular pattern. In FIGS. 5 and 7, for example, these image sensing elements 352 are arranged in a plurality of columns, 342a, 342b, 342c, . . . 342m where m is a finite integer. The first image sensing elements 352 of the columns 342a, 342b, 342c . . . 342m are mutually aligned so as to form a row of image sensing elements 344a. Subsequent rows of image sensing elements 344b, 344c, . . . 344n are similarly formed by the second, third, . . . and nth image sensing elements 352 of each column 342, where n is also a finite integer. Thus configured, it is seen that the image sensing elements 352 comprise an m by n array of image sensing elements 352.

As shown in FIG. 7, each of the image sensing elements 352 arranged in the first column of sensors 342a are tied to a first vertical shift register 346a. Similarly, the image sensing elements 352 of the column 342b are coupled to a second vertical shift register 346b and the image sensing elements 352 of the column 342c are coupled to a third vertical shift register 346c. The image sensing elements 352 of each succeeding column 342, up through 342m, are likewise connected to respective vertical shift registers 346. A horizontal shift register 348 is coupled to each of the vertical shift registers 346a, 346b, 346c, . . . 346m, so as to allow the contents of the vertical shift registers 346 to be loaded in parallel into the horizontal shift register 348.

The vertical shift registers 346a, 346b, 346c, . . . , 346m are controlled via a vertical shift clocking signal 362 directed to each vertical shift register 346 over a signal bus 364. Similarly, a horizontal shift clocking signal 366 is directed to the horizontal shift register 348 over a separate signal bus 368. As depicted in FIG. 7, the vertical shift registers 346a, 346b, 346c, . . . 346m, as well as the h/horizontal shift register 348, are parallel-in, serial-out registers. Each of the vertical shift registers 346 receives parallel input data from the image sensing elements 352 connected thereto. The horizontal shift register 348, on the other hand, receives parallel input data from each of the vertical shift registers 346.

Each of the image sensing elements 352 is adapted to generate a signal as a function of the intensity of the radiation falling thereupon. Thus, for example, the first image sensing element 352 of column 342a generates a signal that is directed to the first vertical shift register 346a over a signal line 372. This signal is stored in a respective storage element of the first vertical shift register 346a. Similar storage elements are present in the first vertical shift register 346a for each of the image sensing elements 352 connected thereto. For convenience, these storage elements will be referred to as the first, second, third, . . . nth storage elements of their respective shift registers 346. When the appropriate vertical shift clocking signal 362 is present on the signal bus 364, the signal stored in the first storage element of a given vertical shift register 346 is shifted to the second storage element of the same register. Simultaneously, the signal stored in the second storage element is shifted to that of the third storage element, and so on, with the signal stored in the nth storage element being shifted out of the vertical shift register into the horizontal shift register 348. As a given signal is thus shifted up through one of the vertical shift registers 346a, 346b, 346c, . . . , or 346m, it passes through the storage elements corresponding to each of the image sensing elements 352 of the respective column 342a, 342b, 342c, . . . , or 342m attached to that particular shift register. While the signal is present in each of these storage elements, it may be augmented by additional signals received from the respective image sensing element 352. This augmentation is explained more fully below.

To illustrate the above process, consider a signal $X_1$ that is generated by the first image sensing element 352 of the first column 342a. This signal is stored in the first storage element of the first vertical shift register 346a. In response to the vertical shift clocking signals 362, this signal $X_1$ will be shifted to the second storage element of the first vertical shift register 346a. While there, it will be augmented with an additional signal, $X_2$, generated by the second image sensing element 352 of the column 342a. Thus, the signal present in the second storage element of the first vertical shift register 346a is now $X_1+X_2$. In response to the next vertical shift clocking signal 362, this signal, $X_1+X_2$, will be shifted to the third storage element of the first vertical shift register 346a. While there, it will be augmented with a signal $X_3$ generated by the third image sensing element 352 of the column 342a. In a like manner, the signal is augmented at each of the storage elements of the first vertical shift register 346a as it is shifted therealong. Thus, the signal that ultimately is shifted out of the first vertical shift register 346a into the horizontal shift register 348 is a signal, $X_T$ that may be expressed as:

$$X_T = \sum_{i=1}^{n} X_i$$

where $X_i$ represents the signal generated by the $i^{th}$ image sensing element 352 at the $i^{th}$ time interval as defined by the vertical shift clocking signal 362.

For linearly scanning systems as described above, an example of a presently available detector technology which meets the requirements of the multi-linear array X-ray detector 350 described above includes a phosphor-coupled-to-CCD array or equivalent gas or solid-state detector capable of detecting X-rays in a time-domain integration (TDI) mode. One type of detector suitable for use in the present invention includes a conventional X-ray to light scintillator, either lens or fiber coupled to a charge-coupled device (CCD) array. Other types of detectors which may be considered for use in the present invention include various types of gas or solid-state detectors (e.g., a-Si:H or a-Se, etc.) configured for detecting X-rays in a time-domain integration (TDI) mode.

CROSS SECTIONAL IMAGE FORMATION WITH A SCANNING X-RAY SOURCE AND A FIXED TEST OBJECT

Laminographic cross sectional image formation using a fixed object with a synchronously scanned X-ray source and detector configuration as shown in FIGS. 4, 5 and 6 may be accomplished by the following procedure. In general, as the X-ray source 320 scans along the linear path 324, the X-ray detector 350 clocks synchronously in the opposite direction such that the projection of a series of adjacent detector image sensing elements 352 to an object plane 334 of the object 330 remains stationery in the object plane 334 as the X-ray scan progresses. For example, during a scan, the detector 350 collects X-ray image data corresponding to a specific region 332a (e.g., a row of object pixels) in the object plane 334 of the object 330 as the region 332a is exposed to X-rays from multiple angles, thus providing the basis for laminographic imaging. This is illustrated in FIG. 4 where a specific row $344_i$ of image sensing elements 352 form an X-ray image of the row of object pixels 332a created by X-rays emitted through the row of object pixels 332a of object 330 from the X-ray source 320 while the X-ray source 320 is located at a first position i. Thus, a first angular configuration is formed by the X-ray source 320 (at location i), the location 332a corresponding to a specific row of object pixels in the object plane 334 within the test object 330, and the row 344i of image sensing elements 352 of the multi-linear array X-ray detector 350. While in this first angular configuration, charge is produced during a first exposure period of time in row 344i of image sensing elements 352 as a result of the radiation received by the image sensing elements 352 during the first exposure period of time. The charge in each image sensing element 352 is placed in a respective storage element of an associated vertical shift register of the X-ray detector 350 and is subsequently shifted up to the next adjacent storage element of the respective vertical shift register during a shift period. During the first shift period, an electronic reconfiguration of the relative positions of the X-ray source 320, the location 332a of the row of object pixels and the multi-linear array X-ray detector 350 is effected such that the X-ray source is positioned at a second position i+1, and the same row of object pixels 332a in the object plane 334 within the test object 330 is imaged on the next row of image sensing elements 352, i.e. row $344_{i+1}$ of detector 350. Similarly, multiple rows of pixels 332 in the object plane 334 within the test object 330 are simultaneously imaged to corresponding rows 344 of multi-linear array X-ray detector 350 during each exposure and shift period. This process is continued through a complete scan(s) of the X-ray source 320 and detector 350 thus forming a laminographic image of the cutting plane 334 of the test object 330. While the above description is in terms of the X-ray source having multiple discrete locations along the scan, it may also be implemented with a continuously scanning X-ray source 320. It is also noted that the detector 350 may execute partial and/or multiple scans during a single scan of the X-ray source 320.

A simplified example further illustrating how the synchronized scan of the X-ray source 320 and the detector 350 forms a cross sectional laminographic image of a cutting plane of an object is shown in the sequence of FIGS. 8a–8m. In this simplified example, a detector 450 having four rows 444 of image sensing elements detects X-rays which pass through a test object 430 which is divided into 10 rows 432 of pixels which are located in a plane 434 of the object 430. The sequence of FIGS. 8a–8m illustrate the manner in which an electronically synchronized scan of the X-ray source 420 and detector 450 forms a cross sectional laminographic image of cutting plane 434 of object 430.

Figure 8A:
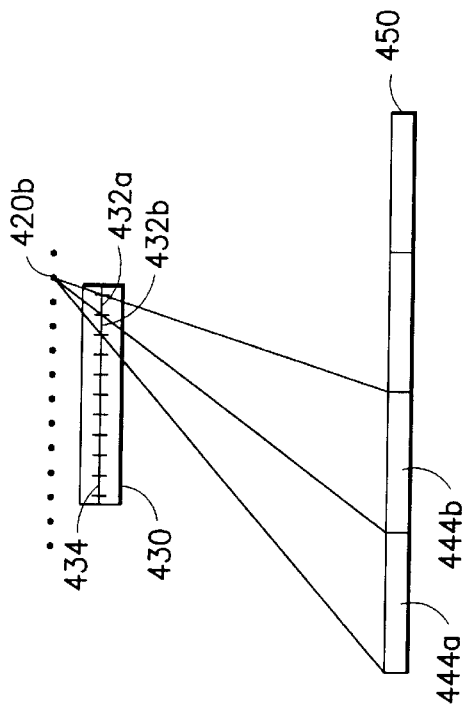

As shown in FIG. 8a, a first angular configuration X-ray image of region 432a (i.e., row of pixels) in the object plane 434 of the object 430 is formed on detector 450 at row 444a when the region 432a is exposed to X-rays from the X-ray source at a position 420a during a first exposure time period $t_{E1}$. The image sensing elements comprising row 444a of the detector 450 convert the detected X-rays representing the first angular configuration X-ray image of region 432a into a set of electrical image signals $X_{a1}$ which are stored in a first set of vertical shift register storage elements. During a first transfer time period $t_{R1}$, the electrical image signals $X_{a1}$ present in the first set of vertical shift register storage elements are shifted into a second set of vertical shift register storage elements (replacing any previous data in the second set of vertical shift register storage elements) and the first set of vertical shift register storage elements are cleared, i.e., set to zero. Additionally, the location of the X-ray source moves from position 420a to position 420b during the first transfer time period $t_{R1}$.

Figure 8B:
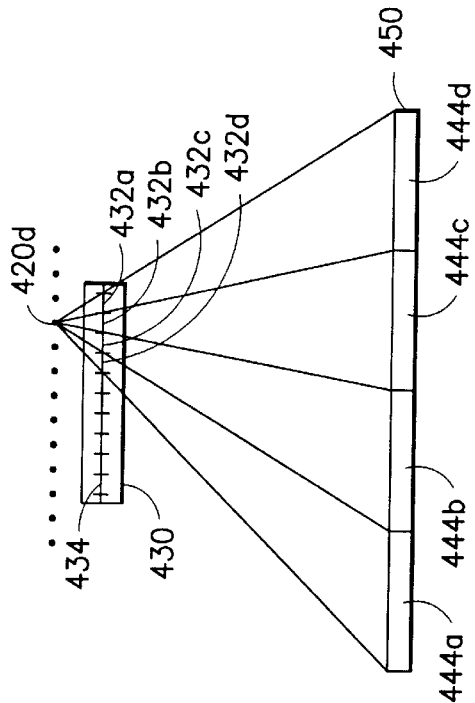

As shown in FIG. 8b, a second angular configuration X-ray image of region 432a (i.e., row of pixels) in the object plane 434 of the object 430 is formed on detector 450 at row 444b when the region 432a is exposed to X-rays from the X-ray source at position 420b during a second exposure time period $t_{E2}$. The image sensing elements comprising row 444b of the detector 450 convert the detected X-rays representing the second angular configuration X-ray image of region 432a into a set of electrical image signals $X_{a2}$ which are added to the set of electrical image signals $X_{a1}$ in the second set of vertical shift register storage elements. A first angular configuration X-ray image of region 432b (i.e., row of pixels) in the object plane 434 of the object 430 is formed on detector 450 at row 444a when the region 432b is exposed to X-rays from the X-ray source at the position 420b during the second exposure time period $t_{E2}$. The image sensing elements comprising row 444a of the detector 450 convert the detected X-rays representing the first angular configuration X-ray image of region 432b into a set of electrical image signals $X_{b1}$ which are stored in the previously cleared first set of vertical shift register storage elements. During a second read time period $t_{R2}$, the electrical image signals $X_{a1}+X_{a2}$ present in the second set of vertical shift register storage elements are shifted into a third set of vertical shift register storage elements (replacing any previous data in the third set of vertical shift register storage elements), the electrical image signals $X_{b1}$ present in the first set of vertical shift register storage elements are shifted into the second set of vertical shift register storage elements (replacing the data previously stored in the second set of vertical shift register storage elements) and the first set of vertical shift register storage elements are again cleared, i.e., set to zero. Additionally, the location of the X-ray source moves from position 420b to position 420c during the second transfer time period $t_{R2}$.

Figure 8C:
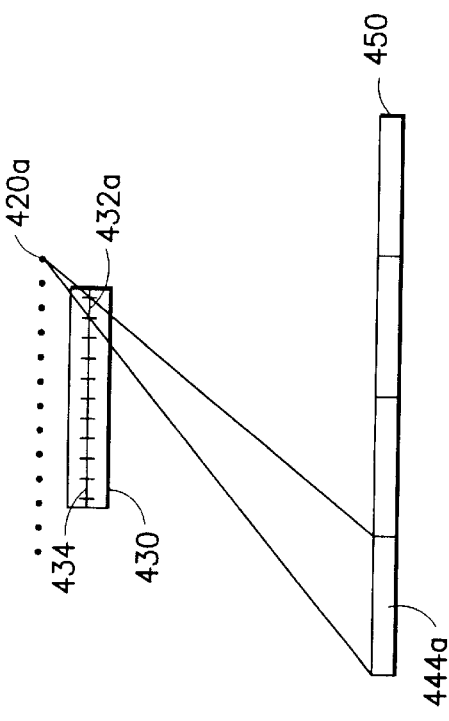

As shown in FIG. 8c, a third angular configuration X-ray image of region 432a (i.e., row of pixels) in the object plane 434 of the object 430 is formed on detector 450 at row 444c when the region 432a is exposed to X-rays from the X-ray source at position 420c during a third exposure time period $t_{E3}$. The image sensing elements comprising row 444c of the detector 450 convert the detected X-rays representing the third angular configuration X-ray image of region 432a into a set of electrical image signals $X_{a3}$ which are added to the first and second sets of electrical image signals $X_{a1}+X_{a2}$ in the third set of vertical shift registers. A second angular configuration X-ray image of region 432b (i.e., row of pixels) in the object plane 434 of the object 430 is formed on detector 450 at row 444b when the region 432b is exposed to X-rays from the X-ray source at position 420c during the third exposure time period $t_{E3}$. The image sensing elements comprising row 444b of the detector 450 convert the detected X-rays representing the second angular configuration X-ray image of region 432b into a set of electrical image signals $X_{b2}$ which are added to the set of electrical image signals $X_{b1}$ in the second set of vertical shift register storage elements. A first angular configuration X-ray image of region 432c (i.e., row of pixels) in the object plane 434 of the object 430 is formed on detector 450 at row 444a when the region 432c is exposed to X-rays from the X-ray source at the position 420c during the third exposure time period $t_{E3}$. The image sensing elements comprising row 444a of the detector 450 convert the detected X-rays representing the first angular configuration X-ray image of region 432c into a set of electrical image signals $X_{c1}$ which are stored in the previously cleared first set of vertical shift register storage elements. During a third read time period $t_{R3}$, the electrical image signals $X_{a1}+X_{a2}+X_{a3}$ present in the third set of vertical shift register storage elements are shifted into a fourth set of vertical shift register storage elements (replacing any previous data in the fourth set of vertical shift register storage elements), the electrical image signals $X_{b1}+X_{b2}$ present in the second set of vertical shift register storage elements are shifted into the third set of vertical shift register storage elements (replacing any previous data in the third set of vertical shift register storage elements), the electrical image signals $X_{c1}$ present in the first set of vertical shift register storage elements are shifted into the second set of vertical shift register storage elements (replacing the data previously stored in the second set of vertical shift register storage elements) and the first set of vertical shift register storage elements are again cleared, i.e., set to zero. Additionally, the location of the X-ray source moves from position 420c to position 420d during the third transfer time period $t_{R3}$.

Figure 8D:
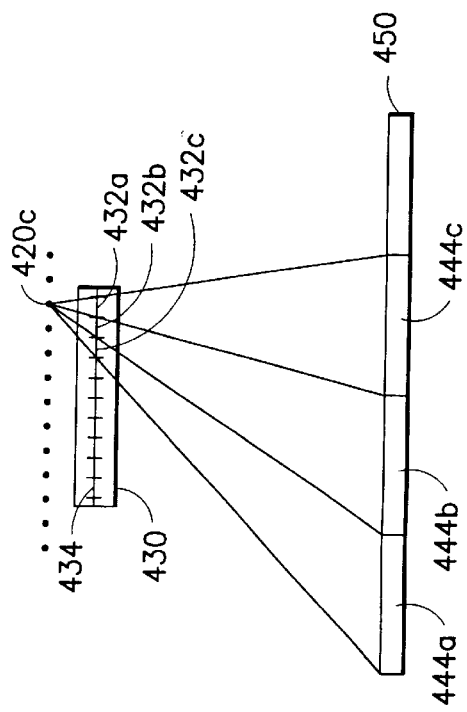
Figure 8E:
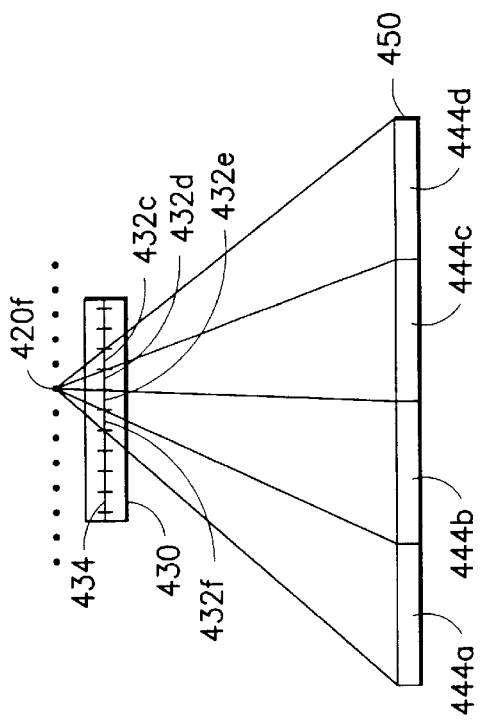
Figure 8F:
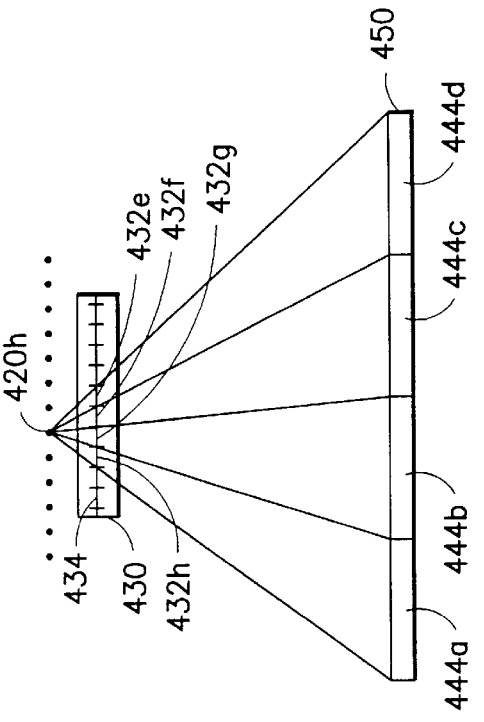
Figure 8G:
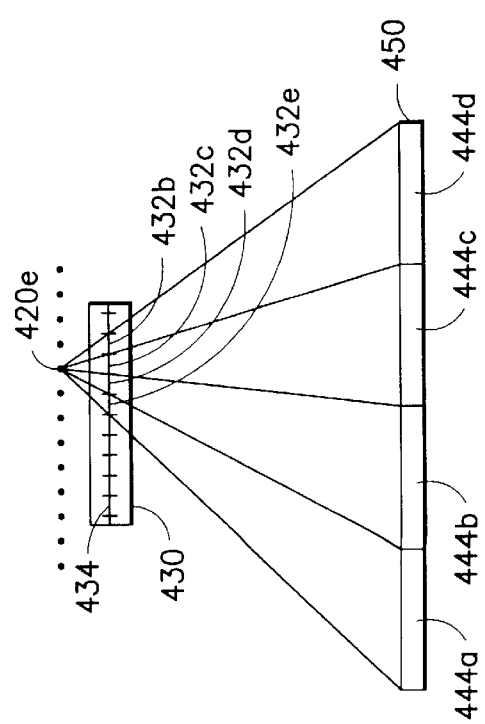
Figure 8H:
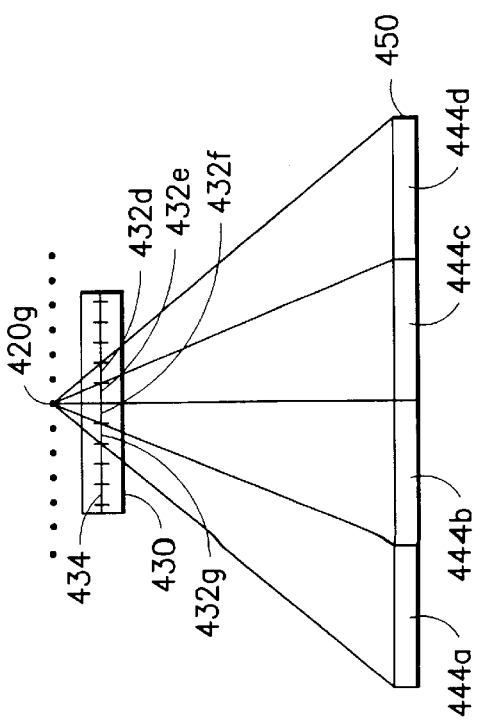

As shown in FIG. 8d, a fourth angular configuration X-ray image of region 432a (i.e., row of pixels) in the object plane 434 of the object 430 is formed on detector 450 at row 444d when the region 432a is exposed to X-rays from the X-ray source at position 420d during a fourth exposure time period $t_{E4}$. The image sensing elements comprising row 444d of the detector 450 convert the detected X-rays representing the fourth angular configuration X-ray image of region 432a into a set of electrical image signals $X_{a4}$ which are added to the first, second and third sets of electrical image signals $X_{a1}+X_{a2}+X_{a3}$ in the fourth set of vertical shift registers. A third angular configuration X-ray image of region 432b (i.e., row of pixels) in the object plane 434 of the object 430 is formed on detector 450 at row 444c when the region 432b is exposed to X-rays from the X-ray source at position 420d during the fourth exposure time period $t_{E4}$. The image sensing elements comprising row 444c of the detector 450 convert the detected X-rays representing the third angular configuration X-ray image of region 432b into a set of electrical image signals $X_{b3}$ which are added to the first and second sets of electrical image signals $X_{b1}+X_{b2}$ in the third set of vertical shift register storage elements. A second angular configuration X-ray image of region 432c (i.e., row of pixels) in the object plane 434 of the object 430 is formed on detector 450 at row 444b when the region 432c is exposed to X-rays from the X-ray source at position 420d during the fourth exposure time period $t_{E4}$. The image sensing elements comprising row 444b of the detector 450 convert the detected X-rays representing the second angular configuration X-ray image of region 432c into a set of electrical image signals $X_{c2}$ which are added to the set of electrical image signals $X_{c1}$ in the second set of vertical shift register storage elements. A first angular configuration X-ray image of region 432d (i.e., row of pixels) in the object plane 434 of the object 430 is formed on detector 450 at row 444a when the region 432d is exposed to X-rays from the X-ray source at the position 420d during the fourth exposure time period $t_{E4}$. The image sensing elements comprising row 444a of the detector 450 convert the detected X-rays representing the first angular configuration X-ray image of region 432d into a set of electrical image signals $X_{d1}$ which are stored in the previously cleared first set of vertical shift register storage elements. During a fourth read time period $t_{R4}$, the electrical image signals $X_{a1}+X_{a2}+X_{a3}+X_{a4}$ present in the fourth set of vertical shift register storage elements are shifted out of the vertical shift registers into a horizontal shift register (see FIG. 7) and/or readout device, the electrical image signals $X_{b1}+X_{b2}+X_{b3}$ present in the third set of vertical shift register storage elements are shifted into the fourth set of vertical shift register storage elements (replacing any previous data in the fourth set of vertical shift register storage elements), the electrical image signals $X_{c1}+X_{c2}$ present in the second set of vertical shift register storage elements are shifted into the third set of vertical shift register storage elements (replacing any previous data in the third set of vertical shift register storage elements), the electrical image signals $X_{d1}$ present in the first set of vertical shift register storage elements are shifted into the second set of vertical shift register storage elements (replacing the data previously stored in the second set of vertical shift register storage elements) and the first set of vertical shift register storage elements are again cleared, i.e., set to zero. Additionally, the location of the X-ray source moves from position 420d to position 420e during the fourth transfer time period $t_{R4}$. Thus, the electrical image signals $X_{a1}+X_{a2}+X_{a3}+X_{a4}$ represent a cross sectional laminographic image of region 432a in cutting plane 434 formed by the four different angular exposures of region 432a.

FIGS. 8e through 8m show the continuation of the sequence of events described in detail with reference to FIGS. 8a, 8b, 8c and 8d. The complete sequence of events shown in FIGS. 8a–8m results in a laminographic cross sectional image of object 430 through the cutting plane 434. The complete laminographic image comprises 10 portions corresponding to each region 432a through 432j where the laminographic image of each region 432 is a combination of four shadow graph images representing four different angular configurations of the X-ray source 420, the locations 432 corresponding to specific rows of object pixels in the object plane 434 within the test object 430, and the rows 444 of image sensing elements 352 of the multi-linear array X-ray detector 450.

The example shown in FIGS. 8a–8m has been simplified for the purposes of illustration. In a typical application, the detector 450 has several hundred or thousand rows 444 of image sensing elements where each row 444 has several hundred or thousand image sensing elements 352. For example, CCD image arrays having 380×488 image sensing elements are readily available. Correspondingly, the number of regions 432 in the image object plane 434 and the number of X-ray source locations 420 are increased as the number of image sensing elements in the detector 450 are increased.

ELECTRONIC LINEAR SCAN LAMINOGRAPHY USING A FIXED X-RAY SOURCE AND A MOVING TEST OBJECT

Figure 9:
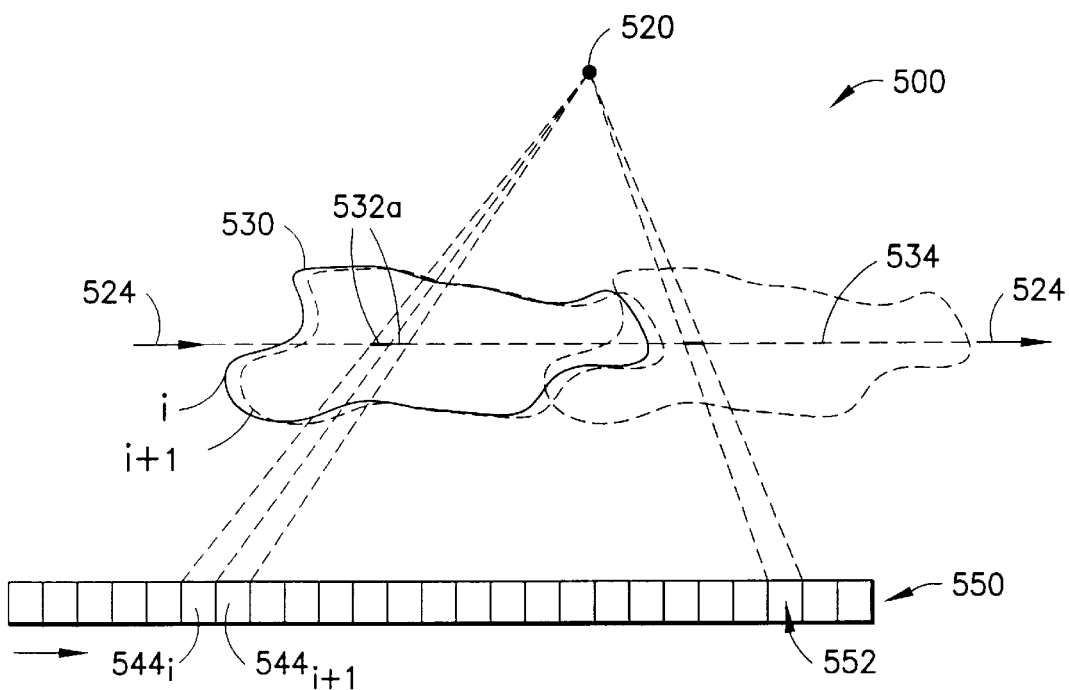
FIG. 9 is a side view illustration of an electronic planar laminography system in a configuration having an X-ray detector which is scanned synchronously with the motion of a test object in accordance with the present invention. In this configuration, the X-ray source is stationary during the scan.
Figure 10:
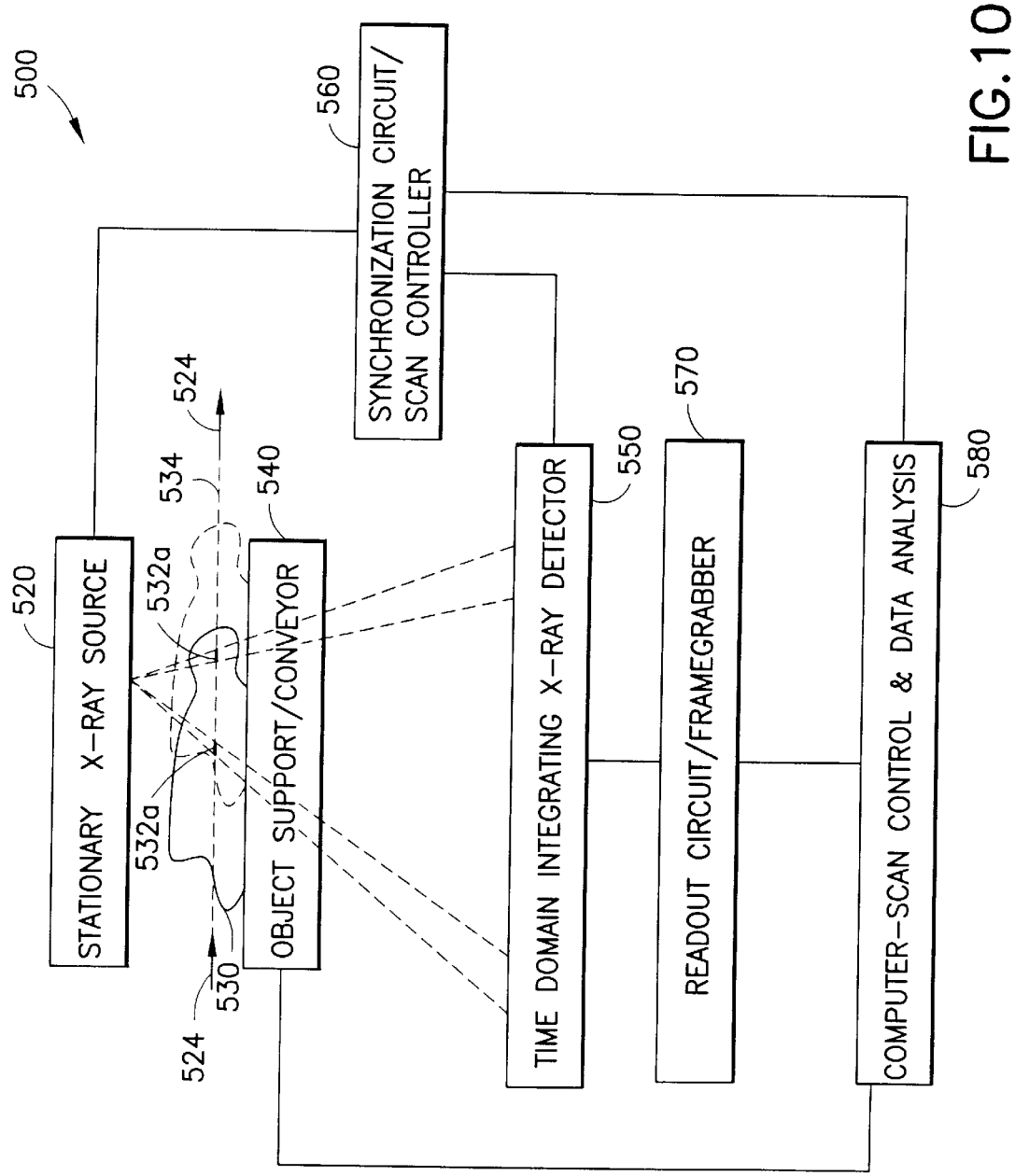
FIG. 10 is a block diagram of the electronic planar laminography system shown in FIG. 9.

A configuration 500 of the present invention for an electronic planar laminography system using a linear scan geometry comprising a fixed/stationary X-ray source 520 and a moving test object 530 is shown in FIGS. 9 and 10. FIG. 9 shows a side view illustration of the electronic planar laminography system 500 in a configuration having a stationary X-ray source 520. FIG. 10 is a block diagram of the electronic planar laminography system 500 shown in FIG. 9. The stationary X-ray source 520 is positioned adjacent a test object 530 being inspected. The test object 530 may be supported by a positioning table/conveyor 540 which is capable of moving the test object 530 along a linear path 524. In addition to the motion along the linear path 524, the positioning table 540 may also be capable of moving the test object 530 to different locations and orientations along two mutually perpendicular axes, X and Y, three mutually perpendicular axes, X, Y and Z, angular motion or a combination of angular and linear motions, depending upon the requirements of a specific inspection. A multi-linear array X-ray detector 550 is positioned adjacent the test object 530 on a side opposite the X-ray source 520. A synchronization circuit/scan controller 560 controls and coordinates the linear motion of the object 530 and the multi-linear array X-ray detector 550. A readout circuit/framegrabber 570 controls the reading of data and image acquisition from the multi-linear array X-ray detector 550. A computer 580 oversees and controls the operation of the entire system including: 1) the linear motion of the object 530; 2) the multi-linear array X-ray detector 550; 3) the synchronization circuit/scan controller 560; 4) the readout circuit/framegrabber 570; and, where appropriate, 5) the positioning table 540. Computer 580 also has the capability to perform high speed image analysis.

CROSS SECTIONAL IMAGE FORMATION WITH A FIXED X-RAY SOURCE AND A MOVING TEST OBJECT

Laminographic cross sectional image formation using the fixed X-ray source 520 with the synchronously scanned X-ray detector 550 and moving test object 530 configuration 500 shown in FIGS. 9 and 10 may be accomplished by the following procedure. In general, as the test object 530 moves along the linear path 524, the X-ray detector 550 clocks synchronously in the same direction such that the projection of a series of adjacent detector image sensing elements 552 to the object plane 534 of the object 530 remains stationery in the object plane 534 as the scan progresses. For example, during the linear motion of the object 530, the detector 550 collects X-ray image data corresponding to a specific region 532a (e.g., a row of object pixels) in the object plane 534 of the object 530 as the region 532a is exposed to X-rays from multiple angles, thus providing the basis for laminographic imaging. This is illustrated in FIG. 9 where a specific row 544$_i$ of image sensing elements 552 form an X-ray image of the row of object pixels 532a created by X-rays emitted through the row of object pixels 532a of object 530 from the X-ray source 520 while the object 530 is located at a first position i. Thus, a first angular configuration is formed by the X-ray source 520, the location 532a corresponding to a specific row of object pixels in the object plane 534 within the test object 530 (at location i), and the row 544i of image sensing elements 552 of the multi-linear array X-ray detector 550. While in this first angular configuration, charge is produced during a first exposure period of time in row 544i of image sensing elements 552 as a result of the radiation received by the image sensing elements 552 during the first exposure period of time. The charge in each image sensing element 552 is placed in a respective storage element of an associated vertical shift register of the X-ray detector 550 and is subsequently shifted up to the next adjacent storage element of the respective vertical shift register during a read or shift period. During the first shift period, an electronic reconfiguration of the relative positions of the X-ray source 520, the location 532a of the row of object pixels and the multi-linear array X-ray detector 550 is effected such that the test object 530 is positioned at a second position i+1, and the same row of object pixels 532a in the object plane 534 within the test object 530 is imaged on the next row of image sensing elements 552, i.e. row 544$_{i+1}$ of detector 550. Similarly, multiple rows of pixels 532 in the object plane 534 within the test object 530 are simultaneously imaged to corresponding rows 544 of the multi-linear array X-ray detector 550 during each exposure and shift period. This process is continued through a complete scan(s) of the moving object 530 and synchronously scanned detector 550 thus forming a laminographic image of the cutting plane 534 of the test object 530. While the above description is in terms of the moving test object 530 having multiple discrete locations along the scan, it may also be implemented with a continuously scanning/moving object 530. It is also noted that the detector 550 may execute partial and/or multiple scans during a single scan of the object 530.

A simplified example further illustrating how a synchronously scanned X-ray detector 650 and a moving test object 630 form a cross sectional laminographic image of a cutting plane of an object is shown in the sequence of FIGS. 11a–11m. In this simplified example, the detector 650 has four rows 644 of image sensing elements for detecting X-rays which pass through the test object 630. The moving test object 630 is divided into 10 rows 632 of pixels which are located in a plane 634 of the object 630. The sequence of FIGS. 11a–11m illustrate the manner in which a synchronized scan of the X-ray detector 650 with the moving test object 630 forms a cross sectional laminographic image of cutting plane 634 of object 630.

Figure 11B:
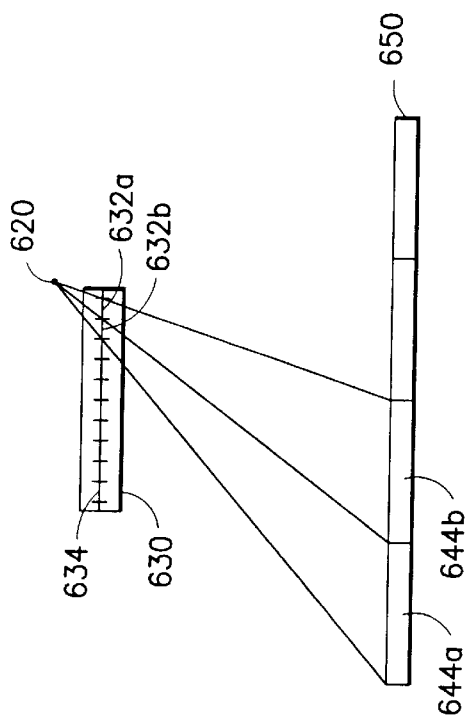
Figure 11D:
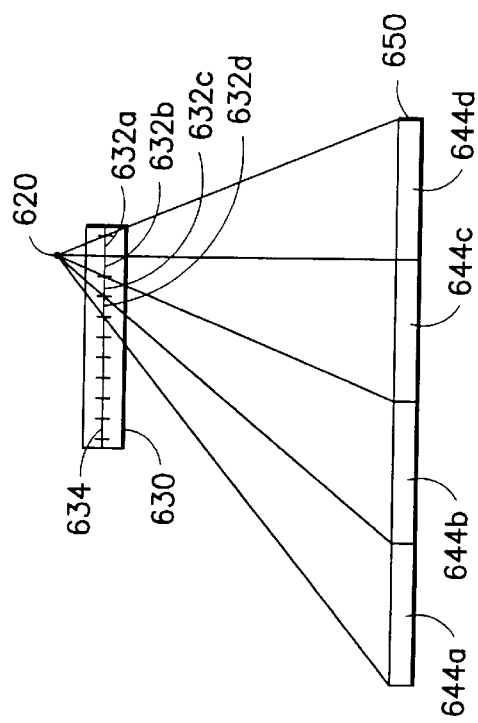
Figure 11A:
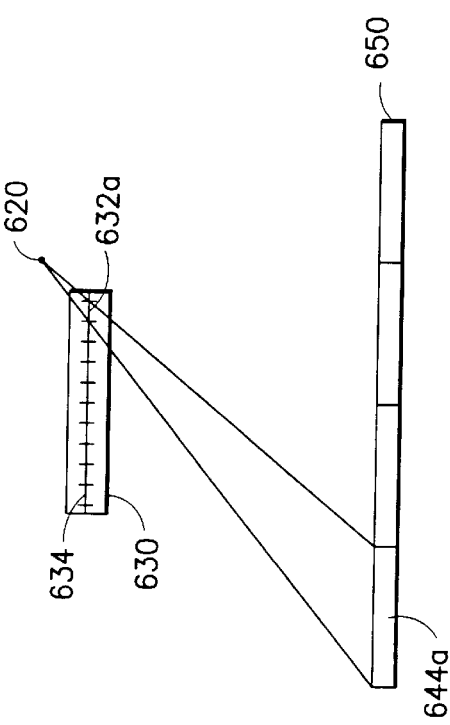
Figure 11C:
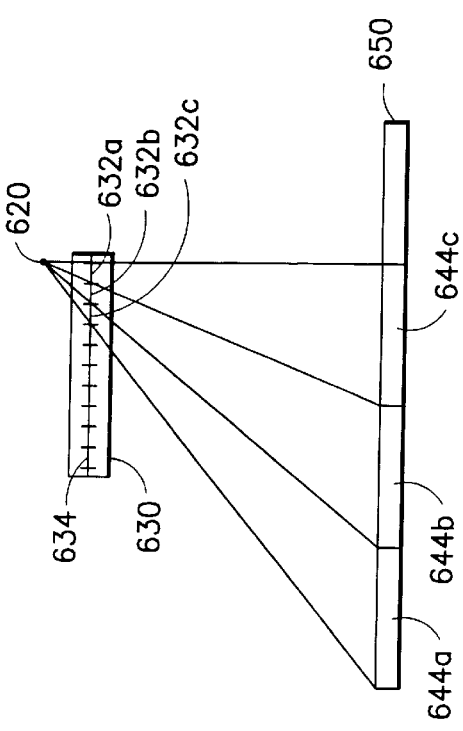
Figure 11F:
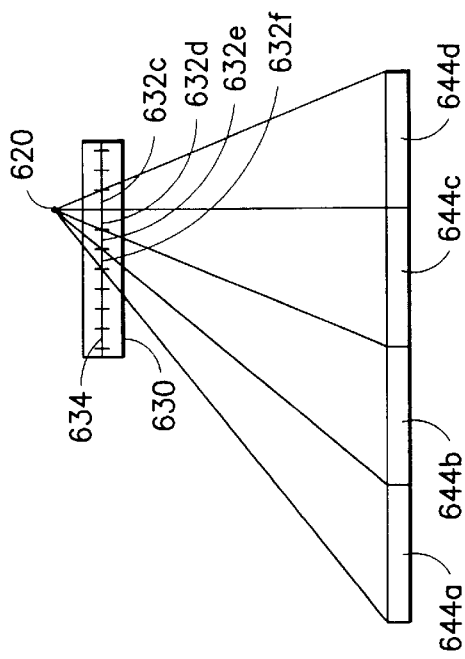
Figure 11H:
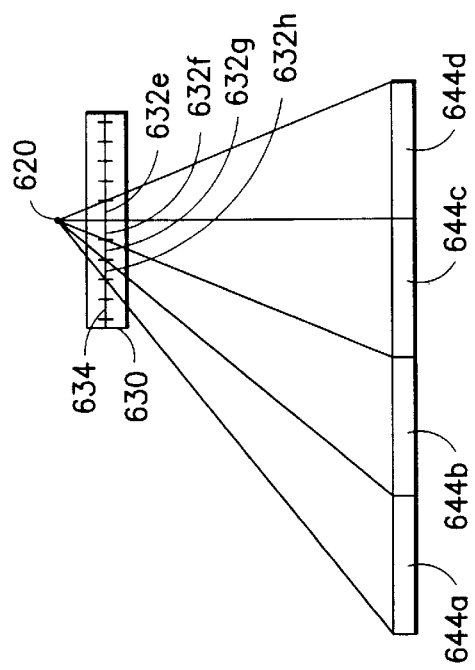
Figure 11E:
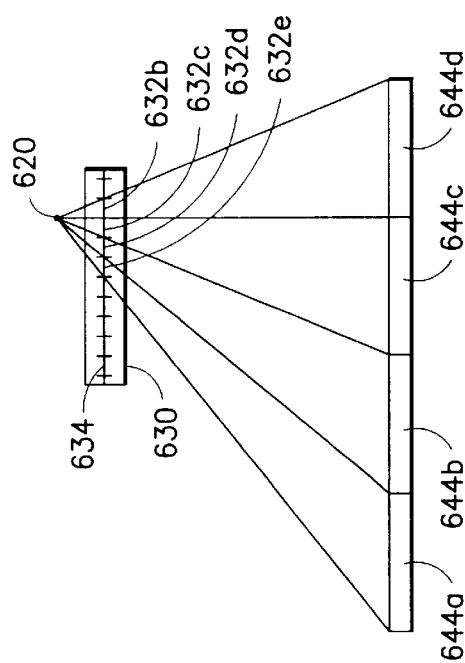
Figure 11G:
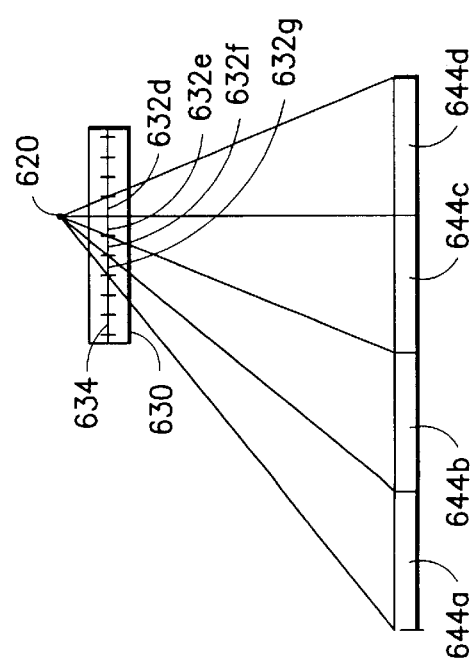
Figure 11M:
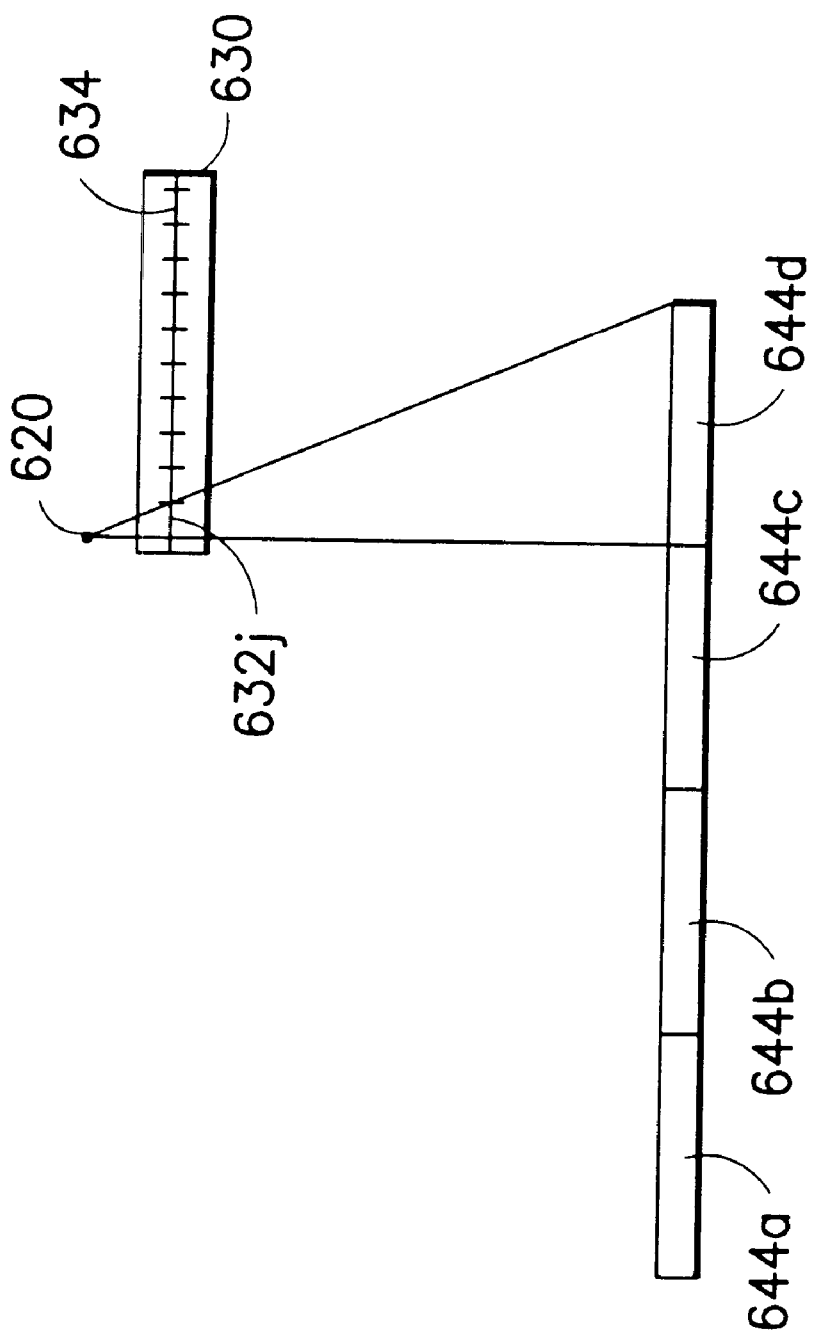

As shown in FIG. 11a, test object 630 is at a first location with respect to the X-ray source 620 and X-ray detector 650. At the first location, a first angular configuration X-ray image of region 632a (i.e., row of pixels) in the object plane 634 of the object 630 is formed on detector 650 at row 644a during a first exposure time period $t_{E1}$. The image sensing elements comprising row 644a of the detector 650 convert X-rays representing the first angular configuration X-ray image of region 632a into a set of electrical image signals $X_{a1}$ which are stored in a first set of vertical shift register storage elements. During a first transfer time period $t_{R1}$, the electrical image signals $X_{a1}$ present in the first set of vertical shift register storage elements are shifted into a second set of vertical shift register storage elements (replacing any previous data in the second set of vertical shift register storage elements) and the first set of vertical shift register storage elements are cleared, i.e., set to zero. Additionally, the test object 630 is moved to the right from the first location with respect to the X-ray source 620 and X-ray detector 650 shown in FIG. 11a to a second location shown in FIG. 11b during the first transfer time period $t_{R1}$.

At the second location (shown in FIG. 11b), a second angular configuration X-ray image of region 632a (i.e., row of pixels) in the object plane 634 of the object 630 is formed on detector 650 at row 644b during a second exposure time period $t_{E2}$. The image sensing elements comprising row 644b of the detector 650 convert the detected X-rays representing the second angular configuration X-ray image of region 632a into a set of electrical image signals $X_{a2}$ which are added to the set of electrical image signals $X_{a1}$ in the second set of vertical shift register storage elements. A first angular configuration X-ray image of region 632b (i.e., row of pixels) in the object plane 634 of the object 630 is formed on detector 650 at row 644a when the region 632b is exposed to X-rays from the X-ray source during the second exposure time period $t_{E2}$. The image sensing elements comprising row 644a of the detector 650 convert the detected X-rays representing the first angular configuration X-ray image of region 632b into a set of electrical image signals $X_{b1}$ which are stored in the previously cleared first set of vertical shift register storage elements. During a second read time period $t_{R2}$, the electrical image signals $X_{a1}+X_{a2}$ present in the second set of vertical shift register storage elements are shifted into a third set of vertical shift register storage elements (replacing any previous data in the third set of vertical shift register storage elements), the electrical image signals $X_{b1}$ present in the first set of vertical shift register storage elements are shifted into the second set of vertical shift register storage elements (replacing the data previously stored in the second set of vertical shift register storage elements) and the first set of vertical shift register storage elements are again cleared, i.e., set to zero. Additionally, the test object 630 is moved to the right from the second location with respect to the X-ray source 620 and X-ray detector 650 shown in FIG. 11b to a third location shown in FIG. 11c during the second transfer time period $t_{R2}$.

At the third location (shown in FIG. 11c), a third angular configuration X-ray image of region 632a (i.e., row of pixels) in the object plane 634 of the object 630 is formed on detector 650 at row 644c during a third exposure time period $t_{E3}$. The image sensing elements comprising row 644c of the detector 650 convert the detected X-rays representing the third angular configuration X-ray image of region 632a into a set of electrical image signals $X_{a3}$ which are added to the first and second sets of electrical image signals $X_{a1}+X_{a2}$ in the third set of vertical shift registers. A second angular configuration X-ray image of region 632b (i.e., row of pixels) in the object plane 634 of the object 630 is formed on detector 650 at row 644b when the region 632b is exposed to X-rays from the X-ray source during the third exposure time period $t_{E3}$. The image sensing elements comprising row 644b of the detector 650 convert the detected X-rays representing the second angular configuration X-ray image of region 632b into a set of electrical image signals $X_{b2}$ which are added to the set of electrical image signals $X_{b1}$ in the second set of vertical shift register storage elements. A first angular configuration X-ray image of region 632c (i.e., row of pixels) in the object plane 634 of the object 630 is formed on detector 650 at row 644a when the region 632c is exposed to X-rays during the third exposure time period $t_{E3}$. The image sensing elements comprising row 644a of the detector 650 convert the detected X-rays representing the first angular configuration X-ray image of region 632c into a set of electrical image signals $X_{c1}$ which are stored in the previously cleared first set of vertical shift register storage elements. During a third read time period $t_{R3}$, the electrical image signals $X_{a1}+X_{a2}+X_{a3}$ present in the third set of vertical shift register storage elements are shifted into a fourth set of vertical shift register storage elements (replacing any previous data in the fourth set of vertical shift register storage elements), the electrical image signals $X_{b1}+X_{b2}$ present in the second set of vertical shift register storage elements are shifted into the third set of vertical shift register storage elements (replacing any previous data in the third set of vertical shift register storage elements), the electrical image signals $X_{c1}$ present in the first set of vertical shift register storage elements are shifted into the second set of vertical shift register storage elements (replacing the data previously stored in the second set of vertical shift register storage elements) and the first set of vertical shift register storage elements are again cleared, i.e., set to zero. Additionally, the test object 630 is moved to the right from the third location with respect to the X-ray source 620 and X-ray detector 650 shown in FIG. 11c to a fourth location shown in FIG. 11d during the third transfer time period $t_{R3}$.

At the fourth location (shown in FIG. 11d), a fourth angular configuration X-ray image of region 632a (i.e., row of pixels) in the object plane 634 of the object 630 is formed on detector 650 at row 644d during a fourth exposure time period $t_{E4}$. The image sensing elements comprising row 644d of the detector 650 convert the detected X-rays representing the fourth angular configuration X-ray image of region 632a into a set of electrical image signals $X_{a4}$ which are added to the first, second and third sets of electrical image signals $X_{a1}+X_{a2}+X_{a3}$ in the fourth set of vertical shift registers. A third angular configuration X-ray image of region 632b (i.e., row of pixels) in the object plane 634 of the object 630 is formed on detector 650 at row 644c during the fourth exposure time period $t_{E4}$. The image sensing elements comprising row 644c of the detector 650 convert the detected X-rays representing the third angular configuration X-ray image of region 632b into a set of electrical image signals $X_{b3}$ which are added to the first and second sets of electrical image signals $X_{b1}+X_{b2}$ in the third set of vertical shift register storage elements. A second angular configuration X-ray image of region 632c (i.e., row of pixels) in the object plane 634 of the object 630 is formed on detector 650 at row 644b during the fourth exposure time period $t_{E4}$. The image sensing elements comprising row 644b of the detector 650 convert the detected X-rays representing the second angular configuration X-ray image of region 632c into a set of electrical image signals $X_{c2}$ which are added to the set of electrical image signals $X_{c1}$ in the second set of vertical shift register storage elements. A first angular configuration X-ray image of region 632d (i.e., row of pixels) in the object plane 634 of the object 630 is formed on detector 650 at row 644a during the fourth exposure time period $t_{E4}$. The image sensing elements comprising row 644a of the detector 650 convert the detected X-rays representing the first angular configuration X-ray image of region 632d into a set of electrical image signals $X_{d1}$ which are stored in the previously cleared first set of vertical shift register storage elements. During a fourth read time period $t_{R4}$, the electrical image signals $X_{a1}+X_{a2}+X_{a3}+X_{a4}$ present in the fourth set of vertical shift register storage elements are shifted out of the vertical shift registers into a horizontal shift register (see FIG. 7) and/or readout device, the electrical image signals $X_{b1}+X_{b2}+X_{b3}$ present in the third set of vertical shift register storage elements are shifted into the fourth set of vertical shift register storage elements (replacing any previous data in the fourth set of vertical shift register storage elements), the electrical image signals $X_{c1}+X_{c2}$ present in the second set of vertical shift register storage elements are shifted into the third set of vertical shift register storage elements (replacing any previous data in the third set of vertical shift register storage elements), the electrical image signals $X_{d1}$ present in the first set of vertical shift register storage elements are shifted into the second set of vertical shift register storage elements (replacing the data previously stored in the second set of vertical shift register storage elements) and the first set of vertical shift register storage elements are again cleared, i.e., set to zero. Additionally, the test object 630 is moved to the right from the fourth location with respect to the X-ray source 620 and X-ray detector 650 shown in FIG. 11d to a fifth location shown in FIG. 11e during the fourth transfer time period $t_{R4}$. Thus, the electrical image signals $X_{a1}+X_{a2}+X_{a3}+X_{a4}$ represent a cross sectional laminographic image of region 632a in cutting plane 634 formed by the four different angular exposures of region 632a.

FIGS. 11e through 11m show the continuation of the sequence of events described in detail with reference to FIGS. 11a, 11b, 11c and 11d. The complete sequence of events shown in FIGS. 11a–11m results in a laminographic cross sectional image of object 630 through the cutting plane 634. The complete laminographic image comprises 10 portions corresponding to each region 632a through 632j where the laminographic image of each region 632 is a combination of four shadow graph images representing four different angular configurations of the X-ray source 620, the locations 632 corresponding to specific rows of object pixels in the object plane 634 within the test object 630, and the rows 644 of image sensing elements 652 of the multi-linear array X-ray detector 650.

The example shown in FIGS. 11a–11m has been simplified for the purposes of illustration. In a typical application, the detector 650 has several hundred or thousand rows 644 of image sensing elements where each row 644 has several hundred or thousand image sensing elements 352. For example, CCD image arrays having 380×488 image sensing elements are readily available. Correspondingly, the number of regions 632 in the image object plane 634 and the number of positions of the object 630 are increased as the number of image sensing elements in the detector 650 are increased. Additionally, the motion of the object 630 may be continuous rather than discrete steps.

ELECTRONIC MOVEMENT OF THE PLANE OF
LAMINOGRAPHIC FOCUS

Figure 12A:
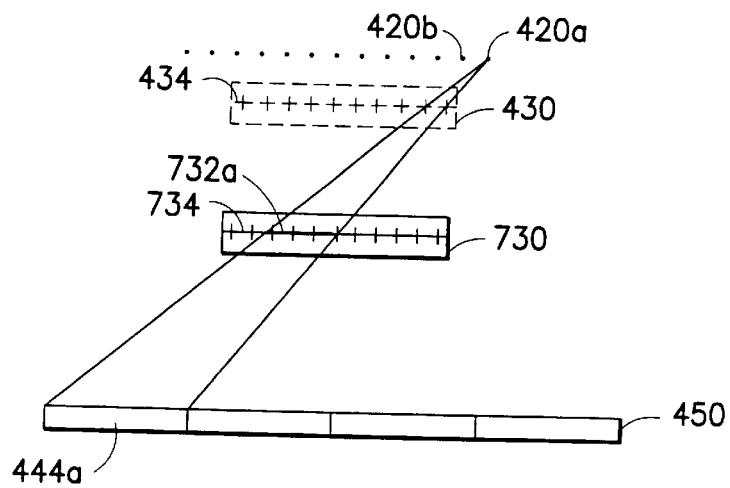
FIGS. 12a–12c illustrate how the location of the object plane (i.e. the plane-of-focus (POF)) of a cross sectional laminographic image of a cutting plane within a test object depends upon the relative scan rates of a scanning X-ray source and a scanning X-ray detector 450.
Figure 12B:
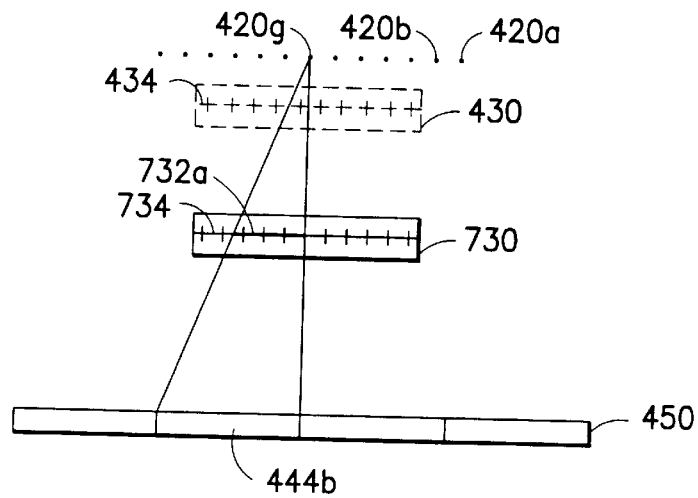
Figure 12C:
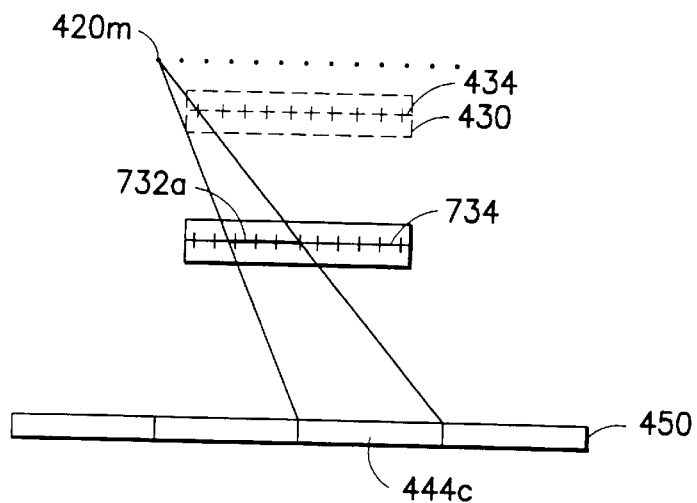

In the configuration of the present invention having a scanning X-ray source and a fixed/stationary test object (see FIGS. 4, 5, 6 and 8), the plane-of-focus (POF), i.e., the location of the object plane 434 within the test object 430, depends upon the relative scan rates of the X-ray source 420 and the detector 450. A simplified example illustrating this feature is shown in the sequence of FIGS. 12a–12c, which represents the same geometrical configuration of the X-ray source 420 and detector 450 as previously discussed in connection with FIGS. 8a–8m. In the sequence of FIGS. 8a–8m, the electronically synchronized scan of the X-ray source 420 and the detector 450 forms a cross sectional laminographic image of cutting plane 434 of object 430 when the scan rate of the X-ray source 420 moves from 420a to 420b in the same time period that the scan rate of the detector 450 moves from row 444a to row 444b, etc. As shown in FIGS. 12a–12c, changing the relative scan rate of the X-ray source 420 and the detector 450 such that the X-ray source 420 moves from 420a to 420g in the same time period that the scan rate of the detector 450 moves from row 444a to row 444b, etc. forms a cross sectional laminographic image of a cutting plane 734 in an object 730. The image resolution and magnification are also changed by the change in relative scan rate.

A simplified example which illustrates how a change in the synchronized scan rate of the X-ray source 420 and the detector 450 results in a change in the plane of focus for formation of a cross sectional laminographic image of a cutting plane of an object is shown in the sequence of FIGS. 12a–12c in conjunction with the sequence of FIGS. 8a–8m. In the sequence of FIGS. 12a–12c, a first relative synchronized scan rate of the X-ray source 420 and the detector 450 summarizes the sequence of FIGS. 8a–8m which results in formation of a laminographic image at the first plane of focus 434. As discussed with reference to FIGS. 8a–8m, when operating at the first scan rate, the X-ray source 420 moves from location 420a to location 420b in the same time period that the synchronized scan of the detector 450 moves from row 444a to row 444b, etc. Similarly, in the sequence of FIGS. 12a–12c, a second relative synchronized scan rate of the X-ray source 420 and the detector 450 results in formation of a laminographic image at a second plane of focus 734. When operating at the second scan rate, the X-ray source 420 moves from location 420a to location 420g (i.e., a distance six times greater than the first scan rate) in the same time period that the synchronized scan of the detector 450 moves from row 444a to row 444b, etc. Thus, if the scan rate of the detector 450 is fixed, the second scan rate of the X-ray source 420 is six times faster than the first scan rate of the X-ray source 420. The same result is achieved if the scan rate of the X-ray source 420 is fixed and the first scan rate of the X-ray detector 450 is six times faster than the second scan rate of the X-ray detector 450. In summary, in the example shown in FIGS. 12a–12c, the plane of focus of the system is located at position 434 when the system scans at the first relative scan rate, while the plane of focus of the system is located at position 734 when the system scans at the second relative scan rate. A detailed discussion of the formation of the laminographic image at the plane of focus at position 734 at the second relative scan rate follows.

As shown in FIG. 12a, when operating at the second synchronized rate, a first angular configuration X-ray image of region 732a (i.e., row of pixels) in the object plane 734 of the object 730 is formed on detector 450 at row 444a when the region 732a is exposed to X-rays from the X-ray source at a position 420a during a first exposure time period $t_{E1}$. The image sensing elements comprising row 444a of the detector 450 convert the detected X-rays representing the first angular configuration X-ray image of region 732a into a set of electrical image signals $X_{a1}$ which are stored in a first set of vertical shift register storage elements. During a first transfer time period $t_{R1}$ the electrical image signals $X_{a1}$ present in the first set of vertical shift register storage elements are shifted into a second set of vertical shift register storage elements (replacing any previous data in the second set of vertical shift register storage elements) and the first set of vertical shift register storage elements are cleared, i.e., set to zero. Additionally, the location of the X-ray source moves from position 420a to position 420g during the first transfer time period $t_{R1}$.

As shown in FIG. 12b, a second angular configuration X-ray image of region 732a (i.e., row of pixels) in the object plane 734 of the object 730 is formed on detector 450 at row 444b when the region 732a is exposed to X-rays from the X-ray source at position 420g during a second exposure time period $t_{E2}$. The image sensing elements comprising row 444b of the detector 450 convert the detected X-rays representing the second angular configuration X-ray image of region 732a into a set of electrical image signals $X_{a2}$ which are added to the set of electrical image signals $X_{a1}$ in the second set of vertical shift register storage elements. During a second read time period $t_{R2}$, the electrical image signals $X_{a1}+X_{a2}$ present in the second set of vertical shift register storage elements are shifted into a third set of vertical shift register storage elements (replacing any previous data in the third set of vertical shift register storage elements) and the first set of vertical shift register storage elements are again cleared, i.e., set to zero. Additionally, the location of the X-ray source moves from position 420g to position 420$_m$ during the second transfer time period $t_{R2}$.

As shown in FIG. 12c, a third angular configuration X-ray image of region 732a (i.e., row of pixels) in the object plane 734 of the object 730 is formed on detector 450 at row 444c when the region 732a is exposed to X-rays from the X-ray source at position 420m during a third exposure time period $t_{E3}$. The image sensing elements comprising row 444c of the detector 450 convert the detected X-rays representing the third angular configuration X-ray image of region 732a into a set of electrical image signals $X_{a3}$ which are added to the first and second sets of electrical image signals $X_{a1}+X_{a2}$ in the third set of vertical shift registers. During a third read time period $t_{R3}$, the electrical image signals $X_{a1}+X_{a2}+X_{a3}$ present in the third set of vertical shift register storage elements are shifted into a fourth set of vertical shift register storage elements (replacing any previous data in the fourth set of vertical shift register storage elements) and the first set of vertical shift register storage elements are again cleared, i.e., set to zero.

In summary, a comparison of the sequence of FIGS. 8a–8m and the sequence of FIGS. 12a–12c illustrates how the location of the object plane changes from location 434 to location 734 as the relative scan rates of the X-ray source 420 and the detector 450 change. In both sequences, if the scan rate of the detector 450 is the same, the X-ray source scans at a rate which is 6 times faster in FIGS. 12a–12c than it does in FIGS. 8a–8m. Alternatively, if the scan rate of the X-ray source 420 is the same, the X-ray detector scans at a rate which is 6 times faster in FIGS. 8a–8m than it does in FIGS. 12a–12c.

X-RAY DETECTOR ALTERNATIVES

It is important to note that the specific shift register architecture of the multi-linear array X-ray detector(s) described herein has been selected primarily for purposes of explaining the fundamental features of time-delay-and-integration and time-domain integration as applied to the present invention. Thus, no presumptions are to be made from this selection or detailed description thereof which would limit the specific type(s) of multi-linear array X-ray detector(s) or details of implementation of these techniques for the present invention. For example, while the present invention may be implemented as described herein, it may also be practiced using different types of detectors including but not limited to detectors wherein: a) the shift registers may be independent of the image sensing elements (as in the case of an interline transfer CCD); or b) the shift registers may coincide with (be the same as) the image sensing elements (as in the case of a full-frame CCD); or c) any other type of detector architecture that performs the same, equivalent or similar functionality to those described herein. The scope of the invention described herein thus encompasses both independent and coincidental shift registers and any other type of shifting architecture that performs the same or similar functionality to those described herein.

THEORETICAL ANALYSIS OF THE TIME-DOMAIN INTEGRATION CROSS-SECTIONAL X-RAY IMAGING ARCHITECTURE

The previous discussion includes two basic approaches for the realization of a Time-Domain Integration (TDI) cross-sectional X-ray imaging architecture. In the first, the object under inspection is held stationary while the X-ray source is moved synchronously with the clocking of the detector. An alternative architecture keeps the source stationary and moves the object. Each approach has its merits and limitations. In the following analysis, it is assumed that the detector is a charge couple device (CCD), since its operation naturally supports TDI imaging. However, before proceeding with the analysis, it is noted that other imaging modalities are also possible with the TDI architecture. As previously shown, the system geometry in both the moving source and moving object cases comprises a source located symmetrically over a scintillator. (However, it is noted that the present invention may also be practiced in non-symmetrical configurations.) One advantage of the symmetric alignment configuration is that it makes acquisition of a direct radiograph trivial, accomplished by using the CCD array in a normal imaging (rather than TDI) mode. Digital tomosynthesis and computed tomography are also possible in the moving source case by taking multiple discrete images at different angular projections (obtained by moving the source and object under inspection). Although doing so may be slow, it nevertheless allows for true three-dimensional imaging where necessary.

Analysis of Moving Source Configuration

An advantage of keeping the object stationary during the X-ray scan is that there is little requirement for good velocity control or exceptional positional stability of the motion platform. If large enough fields-of-view (FOVs) are used, then the object must only be moved a few times to get complete inspection coverage of a circuit board or other object being inspected. Consequently, a lower cost motion platform stage may be employed. Additionally, since the plane-of-focus (POF) depends upon the relative scan rate of the source and detector, it is relatively easy to change focal planes by simply changing the scan rate of the source. (Since a change in the scan rate of the detector requires a different clocking of the detector, this approach is likely to be more difficult to implement than changing the scan rate of the source.) On the other hand, the X-ray source may have a scanning spot which adds to its complexity and cost.

Consider the geometry illustrated in FIG. 13, which shows a linear scan geometry for a moving source configuration of the present invention which produces a cross-sectional image of an object placed in an object plane 834 obtained by clocking a detector array in one direction while moving an X-ray beam in the opposite direction (also see FIGS. 4, 5, 6 and 8). In order to estimate the performance of this architecture, it is advantageous to consider a number of parameters. These include magnification, size of the detector array, length of the X-ray scan, photon flux at the detector, and data rate. In the following analysis, the X-ray scan, FOV, and detector are symmetric with regard to a common bisector. Note that, letting M denote magnification, $$M = \frac{s_1 + s_2}{s_1} \tag{1}$$

where the distance from an X-ray scan plane 824 to the object plane 834 is s, and the distance from the object plane 834 to a detector plane 854 is $s_2$. The total scan distance in the X-ray scan plane 824 is $I_x$, the size of the field of view (FOV) is $I_0$ and the detector size is $I_d$. Additionally, an intersection point 860 is formed by a first line projection 862 from a left end of the X-ray scan plane 824 and a right end of the detector plane 854 and a second line projection 864 from a right end of the X-ray scan plane 824 and a left end of the detector plane 854. Thus, the distance from the object plane 834 to the intersection point 860 is $a_1$ and the distance from the intersection point 860 to the detector plane 854 is $a_2$. By similar triangles $$\frac{s_1 + a_1}{a_1} = \frac{l_x}{l_o} \tag{1a}$$

and $$\frac{a_2}{a_1} = \frac{l_d}{l_o} \tag{1b}$$

Noting that $$a_2 = s_2 - a_1 \quad (1c)$$

elimination of $a_1$ from Equations (1a) and (1b) yields $$l_x = l_o + \frac{l_o + l_d}{M - 1} \quad (2)$$

Equation (2) is useful for determining the total X-ray scan distance $l_x$ corresponding to any specific magnification M, detector size $l_d$ and FOV size $l_o$.

The geometry for computing the sweep angle experienced by any pixel in the object plane 834 is shown in FIG. 14. The sweep angle is the total angular range of X-rays that pass through the pixel for a single X-ray scan. In an ideal case this angle would be 180°. Note that any given pixel in the object plane 834 will not have a contribution to its image from every part of the total X-ray scan. As the X-ray scan proceeds, a given pixel's image will start at one end of the detector pixel, traverse across the detector, and exit the other side of the detector pixel while the X-ray covers only a portion of its total scan distance $l_x$.

As shown in FIG. 14, the scan distance for the pixel is $l_s$, and the distance to the pixel from the edge of the FOV is $p_o$. The scan distance for the pixel is $l_s$ and may be computed by using similar triangles resulting in the following relationship $$\frac{l_s}{s_1} = \frac{l_d}{s_2} \Rightarrow l_s = \frac{l_d}{M - 1} \quad (3)$$

With $\theta$ and $\phi$ as shown in FIG. 14, the total per pixel sweep angle $\beta$ (in radians), is given by $$\beta = \pi - (\theta + \phi) \quad (4a)$$

Since the geometry is symmetric, $$\tan\theta = \frac{s_2}{l_d - (l_d - l_o)/2 - p_o} = \frac{2s_2}{l_d + l_o - 2p_o} \quad (4b)$$

and similarly, $$\tan\phi = \frac{2s_2}{l_d - l_o + 2p_o} \quad (4c)$$

Substituting Eqs. (4b) and (4c) into (4a) yields $$\beta = \pi - \arctan\left(\frac{2s_2}{l_d + l_o - 2p_o}\right) - \arctan\left(\frac{2s_2}{l_d - l_o + 2p_o}\right) \quad (4d)$$

As previously discussed, the location of the POF (i.e., $s_1$ and $s_2$) is determined by the relative scan rate of the X-ray source and detector. Thus, if $t_I$ is the total exposure time, then the scan rate $v_s$ of the X-ray source is $$v_s = \frac{l_d}{t_I(M - 1)} \quad (5)$$

Estimated Signal to Noise Ratio in the Moving Source Configuration

The following discussion includes an estimation of the Signal to Noise Ratio (SNR) for both scintillator/CCD and solid-state detectors. The estimate assumes Poisson statistics and considers the integrated flux over a detector pixel as that pixel clocks across the detector. In the case of a scintillator/CCD type detector, it is further assumed that the scintillator is coupled to the CCD with a lens. The lens coupling portion of the analysis uses a model presented by Liu, Karellas, Harris, and D'Orsi (Liu, Hong; Karellas, Andrew; Harris, Lisa J.; and D'Orsi, Carl J. in "Methods to calculate the lens efficiency in optically coupled CCD x-ray imaging systems," *Medical Physics*, 21 (7), July 1994, pp. 1193–1195).

With reference to FIG. 15, the solid angle $\Omega_p$ subtended by a pixel 952 at an X-ray source 920 may be expressed as $$\Omega_p = \frac{A\cos(\alpha)}{r^2} \quad (6)$$

where r and $\alpha$ are defined as shown in FIG. 15 and A is the area of the pixel 952 at the scintillator. Thus, if the flux emanating from the X-ray source 920 is $\psi_s$ (photons/sr-sec), then the intensity $\psi_p$ incident on the pixel 952 is Since $$\Psi_p = \frac{\Psi_s A \cos\alpha}{r^2} \quad (7a)$$

Since $$r = \frac{y}{\cos\alpha} \quad (7b)$$

and $$y = s_1 + s_2 \quad (7c)$$

$\psi_p$ may be written $$\Psi_p = \frac{\Psi_s A \cos^3\alpha}{(s_1 + s_2)^2} \quad (7d)$$

The total radiation $I_p$ at the scintillator that passes through any particular pixel in the object plane may be found by integrating over the sweep angle and multiplying by the total exposure time $t_I$. Thus, the total incident radiation $I_p$ is given by $$I_p = \frac{\Psi_s A t_I}{(s_1 + s_2)^2} \int_{-(\pi/2 - \theta)}^{(\pi/2 - \phi)} \cos^3\alpha \, d\alpha \quad (8a)$$

Defining $$a = \frac{2s_2}{l_d + l_o - 2p_o} \quad (8b)$$

and $$b = \frac{2s_2}{l_d - l_o + 2p_o} \quad (8c)$$

so that $$\sin\theta = \frac{a}{\sqrt{1 + a^2}}, \cos\theta = \frac{1}{\sqrt{1 + a^2}} \quad (8d)$$

and $$\sin\phi = \frac{b}{\sqrt{1+b^2}}, \cos\phi = \frac{1}{\sqrt{1+b^2}} \quad (8e)$$

evaluation of Equation (8a) yields $$I_p = \frac{\Psi_s A t_I}{(s_1+s_2)^2}\left[\frac{a^2}{3(1+a^2)^{3/2}} + \frac{2}{3(1+a^2)^{1/2}} + \frac{b^2}{3(1+b^2)^{3/2}} + \frac{2}{3(1+b^2)^{1/2}}\right] \quad (8f)$$

Since the scintillator in a typical system is usually much larger than the CCD, fiber coupling of the scintillator to the detector array may be impractical due to the taper of the fiber. Thus, the scintillator is typically coupled to the detector array with a lens. According to the previously referenced analysis by Liu, et. al., the signal-to-noise ratio in a lens coupled X-ray imaging system (with Poisson statistics) is given by $$S/N = \frac{\sqrt{\eta I_p}}{\sqrt{1 + \frac{1}{g_1 g_2 g_3}}} \quad (9)$$

where η represents the quantum efficiency (QE) of the scintillator, $g_1$ is the X-ray to visible photon light yield of the scintillator, $g_2$ is the lens coupling efficiency, and $g_3$ is the QE of the CCD. If T is the lens transmittance, $f^\#$ is the f-number, and m is the minification (inverse of the magnification) between the scintillator and the CCD, then, assuming the scintillator is a Lambertian radiator, $$g_2 = \frac{T}{4(f^\#)^2(1+m)^2+1} \quad (10)$$

Data rates are effectively determined by the total exposure time $t_I$. If the detector array contains N total pixels and there are $b_p$ bits per pixel, then the maximum data rate $d_r$ (in bits/sec) is $$d_r = \frac{Nb_p}{t_I} \quad (11)$$

The average date rate will be lower, since the object under inspection needs to be moved between image scans, during which no data is being read from the CCD.

Analysis of Moving Object Configuration

An alternative to the moving source design keeps the source fixed and synchronizes motion of the object with the scan of the detector. Since the source remains fixed, it can be constructed using a relatively common and low cost design. Furthermore, a section of the entire object can be imaged with one pass, thereby resulting in fewer non-continuous moves of the object. This approach, however, also has its limitations. First, changing the plane-of-focus (POF) requires a complete rescan of a large portion of the object. Second, since the object's motion is synchronized with the scan of the detector, in order to avoid blurring artifacts, the motion platform must have extremely good positional stability and velocity control, which may add significantly to its cost.

Figure 16:
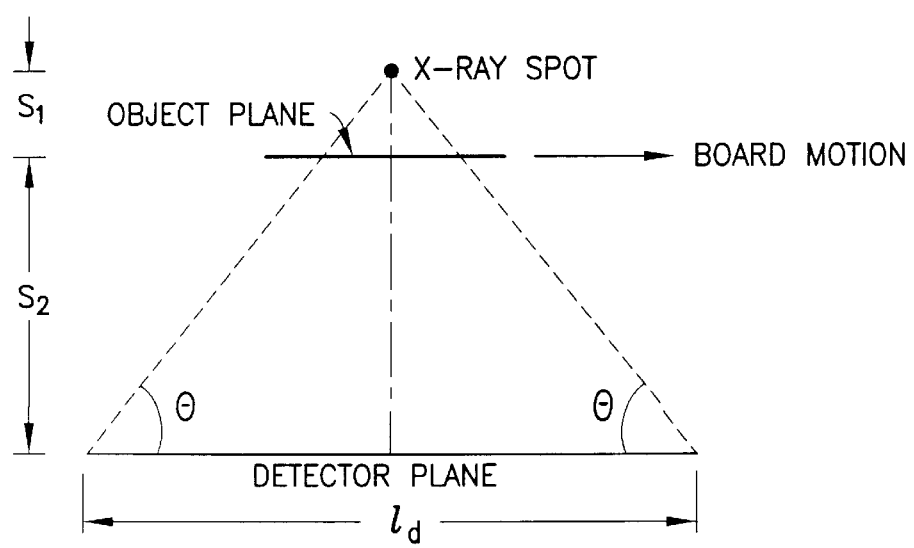
FIG. 16 shows a linear scan geometry for a moving object configuration of the present invention which produces a cross-sectional image of an object placed in the object plane obtained by synchronizing the motion of the object with the clocking of the detector array.

Analysis of the moving object approach is similar to that of the moving source analysis presented above. FIG. 16, which shows the basic time domain integration (TDI) geometry for a moving object and stationary source configuration of the present invention, illustrates the basic geometrical relationships for the moving object case. The magnification factor M is still given by equation (1). The scan rate of the detector is also the same (so that equation (11) still applies for the maximum data rate $d_r$), and the rate of travel of the object $v_o$ is given by $$v_o = \frac{l_d}{Mt_I} \quad (12)$$

As shown in FIG. 16, the X-ray source is located over the center of the detector. Thus, the sweep angle is given by $$\beta = \pi - 2\theta = \pi - 2\arctan\left[\frac{2(s_1+s_2)}{l_d}\right] \quad (13)$$

and subsequently, $$I_p = \frac{\Psi_s A t_I}{3(s_1+s_2)^2}\left\{\frac{l_d(s_1+s_2)^2}{[(s_1+s_2)^2+l_d^2/4]^{3/2}} + \frac{2l_d}{[(s_1+s_2)^2+l_d^2/4]^{1/2}}\right\} \quad (14)$$

Copling from the scintillator to the camera remains the same as in the moving source case. Consequently, equations (9) and (10) still apply for estimation of the S/N ratio.

SPECIFIC DESIGN EXAMPLES OF TIME-DOMAIN INTEGRATION CROSS-SECTIONAL X-RAY IMAGING SYSTEMS

In this section, a number of specific examples of systems which incorporate the features of the present invention illustrate performance trade-offs for different design parameters. All of these examples assume that the object under inspection is a loaded printed circuit board (PCB). The first example design is for a high resolution system, capable of addressing the anticipated inspection needs of the majority of PCB assemblies in the five to ten year out time frame. The second example design is for a standard resolution system aimed at typical assemblies available today. Both examples consider moving source and moving object designs. Additionally, relative system costs are considered. These specific examples are to be considered in all respects only as illustrative of the present invention and not restrictive of the invention.

Both the moving source and moving object designs have their comparative advantages. For example, in the moving object design, motion is more continuous along one axis than in the moving source design. This suggests less throughput degradation due to settling of the PCB after a move is complete. On the other hand, the moving object design requires much better positional stability and velocity control in its motion platform. It will be demonstrated that the moving source design is generally more cost competitive than the moving object design.

General Considerations—High Resolution System Designs

Consider a system with 80 lp/mm resolution. This is about a factor of three higher than the best resolution of the currently available baseline circular scan laminography system previously described (see FIG. 3a). Since the baseline system is capable of limited inspection of solder joints with sizes down to about 4 mils (a 4 mil flip chip, for example, may be inspected for solder bridges and missing balls, but not voiding with the baseline system), a factor of three improvement in resolution implies limited inspection capability for joints down to about 1.3 mils. According to the NEMI technology roadmap previously cited, ball sizes for flip chip devices will reach 50 µm size by the year 2009. Consequently, an 80 lp/mm system should be capable of performing rudimentary inspections of these devices.

Assume that the scintillator has a resolution of 8 lp/mm. (Note: Tacitly assume that the scintillator may be treated as a discrete sampling device and use its resolution to determine an effective pixel size at the scintillator based upon Nyquist limited sampling.) This should be possible for a CsI:TI scintillator of roughly 50 µm thickness. (Note: If an X-ray incident on the scintillator at 45° penetrates the entire scintillator material, its linear spread will be equivalent to the material thickness (to first order). So, for a 50 µm thick scintillator, the lateral spread will also be 50 µm. Since 50 µm corresponds to 10 lp/mm, allowance for some scattering suggests that 50 µm thickness will yield approximately 8 lp/mm.) Thus, to reach a system resolution of 80 lp/mm, will require a magnification of approximately M=10. Allowing for a 1 inch top side board clearance, select $s_1$=1 inch and $s_2$=9 inches. Further select a FOV at the object plane of approximately 2 inches×2 inches (i.e., $I_o$=2).

Example 1A—High Resolution TDI System with Moving Source

This example examines design parameters for a high resolution TDI system with a moving source and a fixed circuit board (FIG. 14). Referring to FIG. 14, shading may become significant if the X-ray beam angle is greater than 45°, i.e., θ>45° and φ>45°. Presuming that greater beam angles lead to no useful added information in the laminograph, take β=90° as the beam sweep angle. Setting $p_o$=1 inch (center of the FOV), inversion of equation (4d) yields a detector size $I_d$=18 inches. At 8 lp/mm resolution, the effective pixel size at the scintillator is A=62.5 µm×62.5 µm which corresponds to a CCD having 7315×7315 pixels. For cost considerations, the following analysis uses a CCD with 10 µm pixels, yielding a CCD having a total size of 2.88 inches×2.88 inches. (Note: Since the contribution of the CCD to the modulation transfer function of the system occurs through a multiplicative factor, ideally the CCD should oversample the scintillator, thereby removing any system resolution degradation due to the CCD. However, for the purposes of this analysis, this fact is ignored and the CCD pixel is matched with the effective pixel required at the scintillator.)

The X-ray source used in the baseline circular scan laminography system previously described (see FIG. 3a) produces approximately $1.2 \times 10^{12}$ photons/sr-sec flux. (Note: This value may be computed using data presented in R. Shane Fazzio, "RADIATION EXPOSURE IN A MODERN, CIRCULARLY SCANNED-BEAM LAMINOGRAPHIC X-RAY INSPECTION SYSTEM," *Journal of X-ray Science and Technology*, Vol. 8, 1998, pp. 117–133.) Power loading in the source target can be increased to about 1 W/µm, across the spot diameter. For a system resolution of 80 lp/mm, the X-ray source will need to have a smaller spot size than the source currently used in the baseline circular scan laminography system (FIG. 3a). Resolution of 100 lp/mm roughly corresponds to a 5 µm spot. Since the existing source in the baseline circular scan laminography system operates at 16 Watts, it may be expected that a flux of approximately ψs=$0.4 \times 10^{12}$ photons/sr-sec may be achieved with a 5 µm spot (best case). Evaluating equation (8f) with these values results in a total radiation $I_p$ at the scintillator of $I_p$=28542 $t_I$.

Based upon the S/N ratio of the baseline circular scan laminography system operating in its highest resolution mode, it is reasonable to select a minimum S/N=35 dB to determine the exposure time $t_I$. According to Rodnyi (Rodnyi, Piotr A., *Physical Processes in Inorganic Scintillators*, CRC Press, Boca Raton, 1997), the light yield of CsI:TI is approximately 56,000 ph/MeV. Furthermore, the light yield scales roughly linearly with energy, down to the energy range in which the baseline circular scan laminography system operates. Since the mean of the baseline circular scan laminography system spectrum is around 60 keV, this results in a value of $g_1$ (the X-ray to visible photon light yield of the scintillator) of $g_1$=3360. Using equation (10) and noting that for a typical camera lens a reasonable value for the lens transmittance T is T=0.9 and a reasonable value for the lens f-number $f^\#$ is $f^\#$=1, the value of $g_2$ (the lens coupling efficiency) becomes $g_2$=0.00426. Given that CsI:TI radiates at approximately 550 nm, an acceptable value for $g_3$ (the QE of the CCD, a "regular" CCD, not back-thinned) is $g_3$=0.3. Finally, integrating the stopping power of CsI:TI over the energy spectrum of the baseline circular scan laminography system, results in a value of η (the quantum efficiency (QE) of the scintillator) of η=0.213. (Note: The energy spectrum of the baseline circular scan laminography system was computed via Monte Carlo simulations using EGS4. More information on the Electron Gamma Shower-EGS Monte Carlo simulation may be found at the EGS Web site, http://ehssun6.lbl.gov/egs/, maintained by Robert D. Stewart at Pacific Northwest National Laboratory and Rick Donahue at Lawrence Berkeley Laboratory.) Stopping powers in CsI:TI came from XOP (European Synchrotron Radiation Facility—http://www.esrf.fr/computing/exrg/subgroups/theory/idi/xop/). Equation (9) may be solved for the exposure time $t_I$ using these values. For example, for a signal to noise ratio of S/N=35 dB, equation (9) yields an exposure time $t_I$ equal to 0.64 sec ($t_I$=0.64 sec).

An actual inspection may require a longer exposure time for the following reason: integration over the source energy spectrum includes low energy photons that will be stopped by the solder joints, thereby providing no useful diagnostic information. Thus, since the effects of solder on the source energy spectrum were not included, the estimation of η may be somewhat optimistic from a "usable information" point of view. For example, at 80 keV, η=0.08, which implies that $t_I$ increases to 1.7 sec. Scaling of throughput may consequently be influenced by the thickness of the solder joints being inspected.

Assuming that the positioning stage can accommodate a move and settle for a 2 inch move in 160 ms (Note: This is reasonable, based upon the actual performance of the positioning stage used in the baseline circular scan laminography system), every FOV requires a total of about 0.8 sec to image. Thus, using a 0.64 sec exposure time, both sides of an 8"×10" board may be inspected in a maximum of 32 sec plus overheads to load and unload the board, align it, and ascertain the proper top and bottom side POF. If the exposure time increases to 1.7 sec, then the overall inspection time increases to 74.4 sec (plus overheads).

The source scan rates and distances for the above example are also achievable. For example, using a 640 ms image acquisition time (i.e., $t_I$=0.64 sec), equation (5) yields a scan rate $v_s$ of the X-ray source of $v_s$=3.125 inches/sec. Similarly, equation (5) yields a scan rate $v_s$ of the X-ray source of $v_s$=1.18 inches/sec for a 1.7 sec image acquisition time (i.e., $t_I$=1.7 sec). From equation (2), it is seen that the total source scan distance $I_x$ for both cases is 4.22 inches.

Example 1B—High Resolution TDI System with Moving Circuit Board

This example examines design parameters for a high resolution TDI system with a moving circuit board and a fixed source (FIG. 16). Many of the parameters remain the same as in the previous example for a high resolution design with a fixed circuit board and a scanning source (FIG. 14), including $s_1$, $s_2$, $g_1$, $g_3$, $f^{\#}$, T, $\psi_s$, A, $\eta$ and the FOV. Again using a sweep angle $\beta=90°$, solution of equation (13) for detector size $I_d$ results in a detector size of $I_d=20$ inches. Then, according to equation (14), the total radiation $I_p$ at the scintillator is $I_p=28542$ $t_f$, which is the same as the previous case. However, if the same camera is used, the minification will be different since the detector size is different, resulting in a decrease in the lens coupling efficiency $g_2$ to $g_2=0.00355$. In order to meet the 35 dB S/N requirement with a value of $\eta=0.213$ for the quantum efficiency (QE) of the scintillator, the exposure time increases slightly to $t_f=0.67$ sec. As before, consideration of the effects of solder on the source energy spectrum may result in a reduced quantum efficiency (QE) of the scintillator $\eta$. For example, at 80 keV, $\eta=0.08$, which implies that $t_f$ increases to 1.77 sec. These increased exposure times add no more than a few seconds to the total inspection time for an 8 inch×10 inch circuit board.

Although the detector reads out continuously in the case of a moving circuit board with a fixed source geometry, its data rates are the same as in the previous case, which again are well within the capabilities of existing detectors. For example, using equation (12), if the exposure time is $t_f=0.67$ sec, then the travel rate $v_o$ of the board is $v_o=3.0$ inches/sec. This travel rate is easily attainable with current moving stage technologies. However, positional stability and velocity control also need to be quite good. Consider that the pixel size at the POF is only 6.25 μm. Consequently, assuming that stability must be no more than one-tenth this to avoid blurring, positional accuracy and velocity control must hold the board, at any one instant in time, to less than about a half-micron of its expected position.

Cost Considerations for High-Resolution TDI Systems

This section provides some qualitative guidelines concerning costs of a high-resolution TDI system. This is acheived by making a number of assumptions regarding cost scaling utilizing known costs of the existing baseline circular scan laminography system (FIG. 3a). Furthermore, the scaling is based upon current dollars only, anticipating that costs of the existing baseline circular scan laminography system will also scale with time.

Consider first the X-ray source. For the moving source case, the source window is roughly comparable in size to that of the source presently used in the baseline circular scan laminography system. Resolution is higher, but falls within existing design capability. Consequently, the source for the TDI system should be roughly the same cost as the baseline system source. In the moving board case, the source is a simpler, fixed beam design. Cost may therefore be reduced, but by no more than a factor of about two.

In the moving source case, the motion platform is functionally equivalent to the motion platform presently used in the baseline circular scan laminography system with the exception of elimination of the Z-axis motion. Further cost savings may be made by improving the design-for-manufacturability of the stage. These adjustments are expected to result in about a 30% cost savings. For the moving object case, only a high-performance air bearing stage with an integrated interferometer is capable of the required positional stability. This in turn implies at least a factor of three or four increase in stage price.

Assuming that scintillator cost is governed by the cost of the CsI:Tl material, a 50 μm scintillator is eight times thinner than the 400 μm CsI:Tl scintillator used in the baseline circular scan laminography system. However, the larger size (18 inches×18 inches), represents an increase in the area of the scintillator by a factor of nearly 14. Thus, it is estimated that the price of the scintillator will double. (Indeed, it will most likely increase by more due to tooling costs required to work with the larger substrate.) For a 20 inches×20 inches scintillator screen, the area increase is a factor of nearly 17. However, increased cost for the scintillator might be offset, since the TDI design does not require a rotational axis to move the scintillator.

The imaging camera for both the moving source and moving object TDI designs includes a CCD with an area of 8.3 sq. inches. This is about a factor of seven larger than the CCD used in the baseline circular scan laminography system. Again, assuming that cost scales with area, it is estimated that the cost of the CCD will be approximately seven times greater than the CCD used in the baseline circular scan laminography system.

In summary, compared to the high resolution TDI system with a moving circuit board, the high resolution TDI system with a moving source evidently has a lower overall cost (primarily due to the trade-off between X-ray source and stage costs). The moving source design also has less stringent mechanical requirements, suggesting that it may be more easily manufacturable, supportable and reliable (with subsequent cost benefits). Nevertheless, even the high resolution TDI system with a moving source will probably be more expensive to manufacture than the existing baseline circular scan laminography system, based upon the increased cost of the CCD. Provided that costs of CCD arrays continue to drop and that CsI:Tl costs drop (as the material becomes more widely used and processes become more efficient), in a few years time, it is expected that the cost of a high-resolution TDI system will become more favorable as compared with the cost of the existing baseline circular scan laminography system.

General Considerations—Standard Resolution Designs

In this section, time-domain-integration (TDI) laminographic systems according to the present invention having resolutions comparable to the highest resolution of the existing baseline circular scan laminography system are discussed. These systems are referred to herein as "standard resolution" systems. It is anticipated that these standard resolution TDI laminographic systems will be capable of inspecting a large fraction of the solder joints used on circuit boards over the next few years. Consequently, these systems offer the industry a mainstream solution that provides significantly higher throughput over the existing baseline circular scan laminography system, with little cost impact. As with the previous discussion of high resolution TDI system designs, both the moving source and moving object standard resolution designs are analyzed below.

As in the high resolution TDI system design examples, the standard resolution TDI system design examples also use a 2 inch×2 inch field-of-view (FOV), i.e. $I_o=2$ inches. Resolution of the current scintillator (400 μm, CsI:Tl) used in the existing baseline circular scan laminography system, is about 3 lp/mm at 30% modulation. Consequently, a magnification of M=7 provides a resolution of 21 lp/mm (at 30% modulation) at the object plane. (Note: A typical baseline circular scan laminography system exhibits up to 25 lp/mm to 30 lp/mm resolution, but at 7.5% modulation.) Allowing for a 1 inch top side board clearance, select $s_1=1$ inch and $s_2=6$ inches. The values for the X-ray to visible photon light yield of the scintillator ($g_1$) and the quantum efficiency (QE) of the CCD ($g_3$) remain unchanged from the high resolution designs previously discussed. Compared to the high resolution design examples, the stopping power of the CsI:Tl scintillator increases to $\eta=0.629$, integrated across the X-ray source spectrum, and it increases to $\eta=0.485$ at 80 keV. As in the high resolution design examples, the standard resolution design examples use a total sweep angle $\beta=90°$. Additionally, the X-ray source continues to operate at 16 Watts, hence, the flux is $\psi_s=1.2\times10^{12}$ photons/sr-sec.

Example 2A—Standard Resolution TDI System with Moving Source

This example examines design parameters for a standard resolution TDI system with a moving source and a fixed circuit board (FIG. 14) having a S/N=35 dB. Inversion of equation (4d) with $s_1=1$ inch, $s_2=6$ inches, $\beta=90°$ (sweep angle) and $p_o=1$ inch (center of the FOV), yields a detector size of $I_d=12$ inches. This results in a total scan distance $I_x$ in the X-ray scan plane of $I_x=4.33$ inches. Note that at 3 lp/mm resolution, the effective pixel size at the scintillator is A=167 $\mu$m×167 $\mu$m. Thus, for a 12"×12" scintillator, the scintillator is effectively covered by 1825×1825 pixels. For cost considerations, the following analysis uses a CCD having a total size no larger than 1 inch×1 inch. As previously discussed, the detector (a scintillator lens coupled to a CCD) used in the following analysis may be replaced with alternative detector technologies with similar results.

Evaluation of equation (8) with these parameters, i.e., $\psi_s=1.2\times10^{12}$ photons/sr-sec, A=167 $\mu$m×167 $\mu$m, $s_1=1$ inch, $s_2=6$ inches, $I_d=12$ inches, $I_o=2$ inches and $p_o=1$ inch, gives the total radiation $I_p$ at the scintillator that passes through any particular pixel in the object plane in terms of the total exposure time $t_I$ as $I_p=1.25\times10^6 t_I$. Again taking T=0.9, and $f^\#=1$, yields $g_2=0.00133$. In order to avoid repeating the analysis at different values of $\eta$, take $\eta=0.56$ (the average of 0.629 and 0.485). Then, solving for $t_I$ with a total radiation $I_p$ at the scintillator which produces a S/N=35 dB, yields an exposure time of $t_I=8$ ms.

This exposure time implies an extremely fast readout rate for the CCD. Typical commercially available CCD's are a factor of two to four slower. Depending upon cost requirements and technological developments, the exposure time might necessarily have to be increased. Even so, with such a low scan time, system performance will be dominated by the motion control platform. As before, assume a 160 ms move and settle time, then the total time required to inspect both sides of an 8"×10" circuit board becomes 6.7 sec (plus load/unload, etc., overheads). (Note: Increasing exposure time by a factor of four results in double the signal-to-noise ratio, while only compromising system throughput by 1 sec for an 8"×10" board.) Note the difference in exposure time $t_I$ between the high resolution and standard resolution cases: the trade-off between resolution and throughput apparently follows a square-law relationship.

Example 2B—Standard Resolution TDI System with Moving Circuit Board

Using the above parameters for the moving board geometry, results in a detector size of $I_d=14$ inches and the same relationship between the total radiation $I_p$ at the scintillator in terms of the total exposure time $t_I$, i.e., $I_p=1.25\times10^6 t_I$. Minification increases to 14, so that $g_2=0.000999$. Therefore, $t_I\approx9$ ms. Throughput is thus effectively the same as in the moving source case. However, in order to meet this exposure rate, the velocity of the stage must be greater than 200 inches/sec. Furthermore, positional stability and velocity control must be accurate to within about 2 $\mu$m at any instant of time. These requirements are exceedingly aggressive and make this choice of geometry practically infeasible.

Cost Considerations for Standard-Resolution TDI Systems

In the moving source case, cost of the X-ray source should be comparable to the source costs for the existing baseline circular scan laminography system. The increase in area over the existing baseline circular scan laminography system suggests about a factor of six cost increase for the scintillator. However, this cost again should be offset by the elimination of the rotational axis in the current baseline circular scan laminography system. Since motion control only requires two axes of motion, there should be up to a 30% cost savings in the motion platform. On the other hand, with motion being the throughput bottleneck, extra investment in stage performance may be desirable from an overall capability perspective. Costs for a 1 inch×1 inch CCD should be comparable with present costs, decreasing accordingly in time. Once again, extra investment may be made to minimize CCD readout rates to help maximize system throughput.

Thus, it is reasonable to conclude that the standard resolution TDI system with a moving source and a fixed circuit board may be constructed for no higher cost (and potentially less cost) than the existing baseline circular scan laminography system and yet offer significantly higher throughput potential. Cost of ownership should also be reduced due to a reduction of mechanical complexity. The moving board TDI geometry is most likely cost prohibitive due to the requirements of the motion platform to meet anticipated exposure times.

CONCLUSIONS

Described herein is a new technique for acquiring a laminographic image using a linear, planar scan geometry. The technique couples a linear X-ray scan with a detector operating in a time-domain integration mode. As previously discussed, the detector (a scintillator lens coupled to a CCD) described herein may be replaced with alternative detector technologies with similar results.

Time-domain integration provides a system architecture capable of either high throughput or high resolution laminography. Although the above discussion uses inspection of solder joints as an application example, the technique is valid for general inspection tasks. The geometries considered are flexible in the sense that they allow direct transmission radiography, digital tomosynthesis, and computed tomography as well.

Two different approaches have been described and characterized, one in which the object under inspection stays stationary, with a scanning X-ray source, and one in which the object moves, using a fixed X-ray source. Both high resolution and high throughput implementations of each design have been described. Naturally, there is a trade-off between resolution and throughput. Thus, performance parameters for both examples were selected to meet the needs of a majority of the developing solder joint inspection market.

Both the high resolution and high throughput geometries of the present invention were compared to an existing baseline circular scan laminography system. It was shown that the system performance of both the high resolution and high throughput geometries of the present invention are better than the baseline circular scan laminography system. Furthermore, in the high throughput case, the performance gain may be achieved at no more (and potentially reduced) cost than the baseline circular scan laminography system.

The baseline circular scan laminography system is not capable of the resolutions considered for the high resolution case, so no comparison can be made.

It will be understood that the apparatus and method of the present invention for electronic planar laminography systems using a linear scan geometry may be embodied in other specific forms without departing from its spirit or essential characteristics. For example, the present invention may also be practiced using multiple detectors, each with possibly different clocking rates or using detectors in other geometrical configurations (e.g., multiple linear detectors arranged in a circular pattern to approximate circular laminography). Additionally, the present invention finds numerous applications outside the field of circuit board inspection. Thus, there are numerous other embodiments of the electronic planar laminography system and method which will be obvious to one skilled in the art. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. An apparatus for producing a laminographic cross sectional image of a cutting plane of an object comprising:
    a scanning X-ray source;
    an X-ray detector positioned to receive X-rays from said scanning X-ray source which have passed through the object, said X-ray detector comprising:
        a plurality of X-ray sensitive elements forming an array wherein each X-ray sensitive element is adapted to sense and generate an X-ray intensity signal value corresponding to the intensity of X-rays received thereon such that said X-ray intensity signal value on any specific X-ray sensitive element is indicative of the total intensity of X-rays received by that specific X-ray sensitive element; and
        connections between said X-ray sensitive elements adapted to allow said X-ray intensity signal values to be shifted from X-ray sensitive element to X-ray sensitive element of said array in response to shift signals corresponding to a first timing pattern such that said X-ray intensity signal values of individual X-ray sensitive elements represent an integration of X-ray intensities received at a plurality of X-ray sensitive element locations as the X-ray intensity signal values shift from X-ray sensitive element to X-ray sensitive element in response to said first timing pattern; and
    a control system which coordinates positioning of said scanning X-ray source with the shifting of said X-ray sensitive element X-ray intensity signal values in accordance with said first timing pattern thereby accumulating data which is representative of a laminographic cross sectional image of a first cutting plane of the object.

2. An apparatus as defined in claim 1 wherein:
    said X-ray detector further responds to a second timing pattern such that said X-ray intensity signal values of individual X-ray sensitive elements represent an integration of X-ray intensities received at said plurality of X-ray sensitive element locations as said X-ray intensity signal values shift from X-ray sensitive element to X-ray sensitive element in response to said second timing pattern; and
    said control system coordinates positioning of said scanning X-ray source with the shifting of said X-ray sensitive element X-ray intensity signal values in accordance with said second timing pattern thereby accumulating data which is representative of a laminographic cross sectional image of a second cutting plane of the object.

3. An apparatus as defined in claim 2 wherein:
    said first timing pattern comprises a first X-ray source scan rate and a first X-ray detector scan rate; and
    said second timing pattern comprises a second X-ray source scan rate and a second X-ray detector scan rate.

4. An apparatus as defined in claim 3 wherein said first X-ray source scan rate and said second X-ray source scan rate are substantially equal.

5. An apparatus as defined in claim 3 wherein said first X-ray detector scan rate and said second X-ray detector scan rate are substantially equal.

6. An apparatus as defined in claim 1 wherein:
    said X-ray detector further responds to a radiographic timing pattern which causes said X-ray intensity signal values of individual X-ray sensitive elements to remain stationary with respect to said array; and
    said control system positions said scanning X-ray source at a stationary location such that said X-ray detector accumulates data which is representative of a conventional X-ray shadowgraph image of the object in accordance with said radiographic timing pattern.

7. An apparatus as defined in claim 1 wherein:
    said X-ray detector further responds to a tomographic timing pattern such that said X-ray intensity signal values of individual X-ray sensitive elements are collected in accordance with a tomographic pattern; and
    said control system coordinates positioning of said scanning X-ray source with the shifting of said X-ray sensitive element X-ray intensity signal values in accordance with said tomographic timing pattern thereby accumulating data from which a digital reconstruction of a tomographic cross sectional image of the object may be reconstructed.

8. An apparatus as defined in claim 1 wherein:
    said X-ray detector further responds to a tomosynthesis timing pattern such that said X-ray intensity signal values of individual X-ray sensitive elements are collected in accordance with a tomosynthesis pattern; and
    said control system coordinates positioning of said scanning X-ray source with the shifting of said X-ray sensitive element X-ray intensity signal values in accordance with said tomosynthesis timing pattern thereby accumulating data from which a digital reconstruction of a tomosynthesis cross sectional image of the object may be reconstructed.

9. An apparatus as defined in claim 1 wherein said scanning X-ray source follows a linear scan direction.

10. An apparatus as defined in claim 1 wherein said scanning X-ray source follows a circular scan direction.

11. An apparatus as defined in claim 1 wherein said scanning X-ray source follows a scan direction determined by a grid.

12. An apparatus as defined in claim 1 wherein said X-ray detector further comprises an X-ray scintillator which converts X-rays to light and a charged coupled device (CCD) which receives and detects said light produced by said X-ray scintillator.

13. An apparatus as defined in claim 1 wherein said X-ray detector further comprises a solid state X-ray detector array which receives X-rays and produces electrical signals in response to receiving X-rays.

14. An apparatus as defined in claim 1 wherein said X-ray detector further comprises a gas detector which receives X-rays and produces electrical signals in response to receiving X-rays.

15. An apparatus for producing a laminographic cross sectional image of a cutting plane of a stationary object comprising:

a scanning X-ray source;

an X-ray detector positioned to receive X-rays from said scanning X-ray source which have passed through the stationary object, said X-ray detector comprising:

a plurality of X-ray sensitive regions forming an array wherein each X-ray sensitive region is adapted to sense X-rays and generate X-ray intensity signal values corresponding to the intensity of X-rays received thereon; and connections between said X-ray sensitive regions adapted to allow said X-ray intensity signal values to be shifted from X-ray sensitive region to X-ray sensitive region of said array in response to shift signals corresponding to a first timing pattern such that said X-ray intensity signal values of individual X-ray sensitive regions represent an integration of X-ray intensities received at a plurality of X-ray sensitive region locations as said X-ray intensity signal values shift from X-ray sensitive region to X-ray sensitive region in response to said first timing pattern; and a control system which coordinates positioning of said scanning X-ray source with said plurality of said X-ray sensitive regions of said X-ray detector such that:

first X-ray image data of the stationary object is collected by a first X-ray sensitive region of said X-ray detector when said X-ray source is located at a first position wherein a first angular relationship is formed between said X-ray source at said first position and said first X-ray sensitive region of said X-ray detector during collection of said first X-ray image data;

second X-ray image data of the stationary object is formed on a second X-ray sensitive region of said X-ray detector when said X-ray source is located at a second position wherein a second angular relationship is formed between said X-ray source at said second position and said second X-ray sensitive region of said X-ray detector during collection of said second X-ray image data; and said first X-ray image data of the stationary object at said first angular configuration and said second X-ray image data of the stationary object at said second angular configuration are combined thereby creating data representative of a laminographic cross sectional image of a first cutting plane of the stationary object.

16. An apparatus as defined in claim 15 wherein:

said X-ray detector further responds to a second timing pattern such that said X-ray intensity signal values of individual X-ray sensitive regions represent an integration of X-ray intensities received at said plurality of X-ray sensitive region locations as said X-ray intensity signal values shift from X-ray sensitive region to X-ray sensitive region in response to said second timing pattern; and said control system coordinates positioning of said scanning X-ray source with said plurality of said X-ray sensitive regions of said X-ray detector in accordance with said second timing pattern such that:

third X-ray image data of the stationary object is formed on said second X-ray sensitive region of said X-ray detector when said X-ray source is located at a third position wherein a third angular relationship is formed between said X-ray source at said third position and said second X-ray sensitive region of said X-ray detector during collection of said third X-ray image data; and said first X-ray image data of the stationary object at said first angular configuration and said third X-ray image data of the stationary object at said third angular configuration are combined thereby creating data which is representative of a laminographic cross sectional image of a second cutting plane of the stationary object.

17. An apparatus as defined in claim 16 wherein:

said first timing pattern comprises a first X-ray source scan rate and a first X-ray detector scan rate; and said second timing pattern comprises a second X-ray source scan rate and a second X-ray detector scan rate.

18. An apparatus as defined in claim 15 wherein:

said X-ray detector further responds to a tomographic timing pattern such that said X-ray intensity signal values of individual X-ray sensitive regions are collected in accordance with a tomographic pattern; and said control system coordinates positioning of said scanning X-ray source with the shifting of said X-ray sensitive region X-ray intensity signal values in accordance with said tomographic pattern thereby accumulating data from which a digital reconstruction of a tomographic cross sectional image of the object may be reconstructed.

19. An apparatus as defined in claim 15 wherein:

said scanning X-ray source follows a linear scan direction;

said X-ray detector further comprises a detector array wherein individual X-ray sensitive elements comprising said detector array are arranged in a plurality of linear rows and linear columns, said linear rows being substantially perpendicular to said X-ray source linear scan direction and said linear columns being substantially parallel to said X-ray source linear scan direction; and regions of the stationary object being imaged are linear regions which are substantially perpendicular to said X-ray source linear scan direction and substantially parallel to said linear rows of said detector array.

20. An apparatus as defined in claim 19 wherein said X-ray detector array further comprises an X-ray scintillator which converts X-rays to light and a charged coupled device (CCD) which receives and detects said light produced by said X-ray scintillator.

21. An apparatus for producing a laminographic cross sectional image of a cutting plane of a stationary object comprising:

a scanning X-ray source which scans along a first linear path;

an X-ray detector array positioned to receive X-rays from said scanning X-ray source which have passed through the object, said X-ray detector array comprising:

a plurality of adjacent X-ray sensitive rows which are substantially perpendicular to said X-ray source first linear path wherein each X-ray sensitive row is adapted to sense X-rays and generate X-ray intensity signal values corresponding to the intensity of X-rays received thereon; and connections between said adjacent X-ray sensitive rows adapted to allow said X-ray intensity signal values to be shifted from X-ray sensitive row to X-ray sensitive row of said X-ray detector array in response to shift signals corresponding to a first timing pattern such that said X-ray intensity signal values of individual X-ray sensitive rows represent multiple angle integrations of X-ray intensities received at a plurality of X-ray sensitive row locations at a plurality of angular orientations of said scanning X-ray source locations and said X-ray detector X-ray sensitive row locations as said X-ray intensity signal values shift from X-ray sensitive row to X-ray sensitive row in response to said first timing pattern; and a control system which coordinates positioning of said scanning X-ray source with the shifting of said X-ray intensity signal values of said X-ray detector in accordance with said first timing pattern thereby creating data representative of a laminographic cross sectional image of a first cutting plane of the stationary object.

22. An apparatus as defined in claim 21 wherein:

said X-ray detector further responds to a second timing pattern such that said X-ray intensity signal values of individual X-ray sensitive rows represent an integration of X-ray intensities received at said plurality of X-ray sensitive row locations as said X-ray intensity signal values shift from X-ray sensitive row to X-ray sensitive row in response to said second timing pattern; and said control system coordinates positioning of said scanning X-ray source with the shifting of said X-ray intensity signal values in accordance with said second timing pattern thereby accumulating data which is representative of a laminographic cross sectional image of a second cutting plane of the object.

23. An apparatus as defined in claim 22 wherein:

said first timing pattern comprises a first X-ray source scan rate and a first X-ray detector scan rate; and said second timing pattern comprises a second X-ray source scan rate and a second X-ray detector scan rate.

24. An apparatus as defined in claim 21 wherein:

said X-ray detector further responds to a tomographic timing pattern such that said X-ray intensity signal values are collected in accordance with a tomographic pattern; and said control system coordinates positioning of said scanning X-ray source with the shifting of said X-ray intensity signal values in accordance with said tomographic pattern thereby accumulating data from which a digital reconstruction of a tomographic cross sectional image of the object may be reconstructed.

25. An apparatus as defined in claim 21 wherein said X-ray detector further comprises an X-ray scintillator which converts X-rays to light and a charged coupled device (CCD) which receives and detects said light produced by said X-ray scintillator.

26. An apparatus for producing a laminographic cross sectional image of a first cutting plane of an object comprising:

a scanning X-ray source;

a scanning X-ray detector array positioned to receive X-rays from said scanning X-ray source which have passed through the object, said scanning X-ray detector comprising:

a plurality of X-ray sensitive elements adapted to sense and generate X-ray intensity signal values corresponding to the intensity of X-rays received thereon, said X-ray intensity signal values thereby representing an X-ray image of a portion of the object; and connections between said X-ray sensitive elements adapted to allow said X-ray intensity signal values representing X-ray images to be shifted from X-ray sensitive element to X-ray sensitive element of said scanning X-ray detector array in response to shift signals corresponding to a first timing pattern such that said X-ray intensity signal values of individual X-ray sensitive elements correspond to an integration of X-ray intensities received at a plurality of X-ray sensitive element locations and a plurality of angular orientations of said X-ray source and said scanning X-ray detector X-ray sensitive element locations as said X-ray intensity signal values representing X-ray images shift from X-ray sensitive element to X-ray sensitive element in response to said first timing pattern; and a control system which coordinates positioning of said scanning X-ray source with the shifting of said X-ray sensitive element X-ray intensity signal values in accordance with said first timing pattern such that multiple angular image projections of the first cutting plane of the object are accumulated by said scanning X-ray detector array wherein any point in the first cutting plane of the object is projected to approximately the same shifted point of the scanning X-ray detector array X-ray sensitive elements and any point outside the first cutting plane is projected to a plurality of shifted points of the scanning X-ray detector array X-ray sensitive elements during a cycle of the first timing pattern thereby accumulating data which is representative of a laminographic cross sectional image of the first cutting plane of the object.

27. An apparatus as defined in claim 26 wherein:

said scanning X-ray detector array further responds to a second timing pattern such that said X-ray intensity signal values of individual X-ray sensitive elements represent an integration of X-ray intensities received at said plurality of X-ray sensitive element locations and said plurality of angular orientations of said X-ray source and said scanning X-ray detector array X-ray sensitive element locations as said X-ray intensity signal values representing X-ray images shift from X-ray sensitive element to X-ray sensitive element in response to said second timing pattern; and said control system coordinates positioning of said scanning X-ray source with the shifting of said X-ray sensitive element X-ray intensity signal values in accordance with said second timing pattern such that multiple angular image projections of a second cutting plane of the object are accumulated by said scanning X-ray detector array wherein any point in the second cutting plane of the object is projected to approximately the same shifted point of the scanning X-ray detector array X-ray sensitive elements and any point outside the second cutting plane is projected to a plurality of shifted points of the scanning X-ray detector array X-ray sensitive elements during a cycle of the second timing pattern thereby accumulating data which is representative of a laminographic cross sectional image of a second cutting plane of the object.

28. An apparatus as defined in claim 27 wherein:

said first timing pattern comprises a first X-ray source scan rate and a first X-ray detector scan rate; and said second timing pattern comprises a second X-ray source scan rate and a second X-ray detector scan rate.

29. An apparatus as defined in claim 26 wherein:

said scanning X-ray detector array further responds to a tomographic timing pattern such that said X-ray intensity signal values of individual X-ray sensitive elements are collected in accordance with a tomographic pattern; and said control system coordinates positioning of said scanning X-ray source with the shifting of said X-ray sensitive element X-ray intensity signal values in accordance with said tomographic pattern thereby accumulating data from which a digital reconstruction of a tomographic cross sectional image of the object may be reconstructed.

30. An apparatus as defined in claim 26 wherein said scanning X-ray source follows a linear scan direction.

31. An apparatus as defined in claim 26 wherein said scanning X-ray detector array further comprises an X-ray scintillator which converts X-rays to light and a charged coupled device (CCD) which receives and detects said light produced by said X-ray scintillator.

32. An apparatus for producing a laminographic cross sectional image of a cutting plane of an object comprising:

a stationary X-ray source;

a moving support for the object;

an X-ray detector positioned to receive X-rays from said stationary X-ray source which have passed through the object, said X-ray detector comprising:

a plurality of X-ray sensitive elements forming an array wherein each X-ray sensitive element is adapted to sense and generate an X-ray intensity signal value corresponding to the intensity of X-rays received thereon such that said X-ray intensity signal value on any specific X-ray sensitive element is indicative of the total intensity of X-rays received by that specific X-ray sensitive element; and connections between said X-ray sensitive elements adapted to allow said X-ray intensity signal values to be shifted from X-ray sensitive element to X-ray sensitive element of said array in response to shift signals corresponding to a first timing pattern such that said X-ray intensity signal values of individual X-ray sensitive elements represent an integration of X-ray intensities received at a plurality of X-ray sensitive element locations as the X-ray intensity signal values shift from X-ray sensitive element to X-ray sensitive element in response to said first timing pattern; and a control system which coordinates positioning of said moving support with the shifting of said X-ray sensitive element X-ray intensity signal values in accordance with said first timing pattern thereby accumulating data which is representative of a laminographic cross sectional image of a first cutting plane of the object.

33. An apparatus as defined in claim 32 wherein:

said X-ray detector further responds to a second timing pattern such that said X-ray intensity signal values of individual X-ray sensitive elements represent an integration of X-ray intensities received at said plurality of X-ray sensitive element locations as said X-ray intensity signal values shift from X-ray sensitive element to X-ray sensitive element in response to said second timing pattern; and said control system coordinates positioning of said moving support with the shifting of said X-ray sensitive element X-ray intensity signal values in accordance with said second timing pattern thereby accumulating data which is representative of a laminographic cross sectional image of a second cutting plane of the object.

34. An apparatus as defined in claim 33 wherein:

said first timing pattern comprises a first moving support scan rate and a first X-ray detector scan rate; and said second timing pattern comprises a second moving support scan rate and a second X-ray detector scan rate.

35. An apparatus as defined in claim 32 wherein:

said X-ray detector further responds to a tomographic timing pattern such that said X-ray intensity signal values of individual X-ray sensitive elements are collected in accordance with a tomographic pattern; and said control system coordinates positioning of said moving support with the shifting of said X-ray sensitive element X-ray intensity signal values in accordance with said tomographic timing pattern thereby accumulating data from which a digital reconstruction of a tomographic cross sectional image of the object may be reconstructed.

36. An apparatus as defined in claim 32 wherein said moving support follows a linear scan direction.

37. An apparatus as defined in claim 32 wherein said X-ray detector further comprises an X-ray scintillator which converts X-rays to light and a charged coupled device (CCD) which receives and detects said light produced by said X-ray scintillator.

38. A method for producing a laminographic cross sectional image of a cutting plane of an object comprising the steps of:

scanning the object with a scanning X-ray source;

detecting X-rays from said scanning X-ray source which have passed through the object with an X-ray detector, said X-ray detector comprising:

a plurality of X-ray sensitive elements forming an array wherein each X-ray sensitive element is adapted to sense and generate an X-ray intensity signal value corresponding to the intensity of X-rays received thereon such that said X-ray intensity signal value on any specific X-ray sensitive element is indicative of the total intensity of X-rays received by that specific X-ray sensitive element; and connections between said X-ray sensitive elements adapted to allow said X-ray intensity signal values to be shifted from X-ray sensitive element to X-ray sensitive element of said array in response to shift signals corresponding to a first timing pattern such that said X-ray intensity signal values of individual X-ray sensitive elements represent an integration of X-ray intensities received at a plurality of X-ray sensitive element locations as the X-ray intensity signal values shift from X-ray sensitive element to X-ray sensitive element in response to said first timing pattern; and coordinating the position of said scanning X-ray source with the shifting of said X-ray sensitive element X-ray intensity signal values with a control system in accordance with said first timing pattern thereby accumulating data which is representative of a laminographic cross sectional image of a first cutting plane of the object.

39. A method as defined in claim 38 wherein:

said X-ray detector further responds to a second timing pattern such that said X-ray intensity signal values of individual X-ray sensitive elements represent an integration of X-ray intensities received at said plurality of X-ray sensitive element locations as said X-ray intensity signal values shift from X-ray sensitive element to X-ray sensitive element in response to said second timing pattern; and said control system coordinates positioning of said scanning X-ray source with the shifting of said X-ray sensitive element X-ray intensity signal values in accordance with said second timing pattern thereby accumulating data which is representative of a laminographic cross sectional image of a second cutting plane of the object.

40. A method as defined in claim 39 wherein:

said first timing pattern comprises a first X-ray source scan rate and a first X-ray detector scan rate; and said second timing pattern comprises a second X-ray source scan rate and a second X-ray detector scan rate.

41. A method as defined in claim 38 wherein:

said X-ray detector further responds to a tomographic timing pattern such that said X-ray intensity signal values of individual X-ray sensitive elements are collected in accordance with a tomographic pattern; and said control system coordinates positioning of said scanning X-ray source with the shifting of said X-ray sensitive element X-ray intensity signal values in accordance with said tomographic timing pattern thereby accumulating data from which a digital reconstruction of a tomographic cross sectional image of the object may be reconstructed.

42. A method as defined in claim 38 wherein said scanning X-ray source follows a linear scan direction.

43. A method as defined in claim 38 wherein said X-ray detector further comprises an X-ray scintillator which converts X-rays to light and a charged coupled device (CCD) which receives and detects said light produced by said X-ray scintillator.

44. A method for producing a laminographic cross sectional image of a cutting plane of an object comprising:

providing a stationary X-ray source;

providing a moving support for the object;

positioning an X-ray detector to receive X-rays from said stationary X-ray source which have passed through the object, said X-ray detector comprising:

a plurality of X-ray sensitive elements forming an array wherein each X-ray sensitive element is adapted to sense and generate an X-ray intensity signal value corresponding to the intensity of X-rays received thereon such that said X-ray intensity signal value on any specific X-ray sensitive element is indicative of the total intensity of X-rays received by that specific X-ray sensitive element; and connections between said X-ray sensitive elements adapted to allow said X-ray intensity signal values to be shifted from X-ray sensitive element to X-ray sensitive element of said array in response to shift signals corresponding to a first timing pattern such that said X-ray intensity signal values of individual X-ray sensitive elements represent an integration of X-ray intensities received at a plurality of X-ray sensitive element locations as the X-ray intensity signal values shift from X-ray sensitive element to X-ray sensitive element in response to said first timing pattern; and providing a control system which coordinates positioning of said moving support with the shifting of said X-ray sensitive element X-ray intensity signal values in accordance with said first timing pattern thereby accumulating data which is representative of a laminographic cross sectional image of a first cutting plane of the object.

45. A method as defined in claim 44 wherein:

said X-ray detector further responds to a second timing pattern such that said X-ray intensity signal values of individual X-ray sensitive elements represent an integration of X-ray intensities received at said plurality of X-ray sensitive element locations as said X-ray intensity signal values shift from X-ray sensitive element to X-ray sensitive element in response to said second timing pattern; and said control system coordinates positioning of said moving support with the shifting of said X-ray sensitive element X-ray intensity signal values in accordance with said second timing pattern thereby accumulating data which is representative of a laminographic cross sectional image of a second cutting plane of the object.

46. A method as defined in claim 45 wherein:

said first timing pattern comprises a first moving support scan rate and a first X-ray detector scan rate; and said second timing pattern comprises a second moving support scan rate and a second X-ray detector scan rate.

47. A method as defined in claim 44 wherein:

said X-ray detector further responds to a tomographic timing pattern such that said X-ray intensity signal values of individual X-ray sensitive elements are collected in accordance with a tomographic pattern; and said control system coordinates positioning of said moving support with the shifting of said X-ray sensitive element X-ray intensity signal values in accordance with said tomographic timing pattern thereby accumulating data from which a digital reconstruction of a tomographic cross sectional image of the object may be reconstructed.

48. A method as defined in claim 44 wherein said moving support follows a linear scan direction.

49. A method as defined in claim 44 wherein said X-ray detector further comprises an X-ray scintillator which converts X-rays to light and a charged coupled device (CCD) which receives and detects said light produced by said X-ray scintillator.

* * * * *